United States Patent
Einav et al.

(10) Patent No.: US 10,322,253 B2
(45) Date of Patent: Jun. 18, 2019

(54) BALLOONED VENTILATION TUBE CLEANING DEVICE

(75) Inventors: Elad Einav, Tel Aviv (IL); Oron Zachar, Tel Aviv (IL)

(73) Assignee: TELEFLEX LIFE SCIENCES UNLIMITED COMPANY, Hamilton (BM)

( * ) Notice: Subject to any disclaimer, the term of this patent is extended or adjusted under 35 U.S.C. 154(b) by 542 days.

(21) Appl. No.: 14/008,558

(22) PCT Filed: Mar. 29, 2012

(86) PCT No.: PCT/IB2012/051532
§ 371 (c)(1),
(2), (4) Date: Nov. 29, 2013

(87) PCT Pub. No.: WO2012/131626
PCT Pub. Date: Oct. 4, 2012

(65) Prior Publication Data
US 2014/0246015 A1 Sep. 4, 2014

Related U.S. Application Data

(60) Provisional application No. 61/539,998, filed on Sep. 28, 2011, provisional application No. 61/560,385, (Continued)

(30) Foreign Application Priority Data
Sep. 26, 2011 (PL) .......................................... 396436

(51) Int. Cl.
*A61M 1/00* (2006.01)
*A61M 16/00* (2006.01)
(Continued)

(52) U.S. Cl.
CPC .... *A61M 16/0463* (2013.01); *A61M 16/0057* (2013.01); *A61M 16/0438* (2014.02);
(Continued)

(58) Field of Classification Search
CPC ...... A61M 2025/0019; A61M 16/0463; A61M 16/0459; A61M 16/0456; A61M 16/0438;
(Continued)

(56) References Cited

U.S. PATENT DOCUMENTS 3,211,150 A 10/1965 Foderick
3,502,069 A 3/1970 Silverman
(Continued)

FOREIGN PATENT DOCUMENTS

EP 0692273 A1 1/1996
EP 1239907 A1 9/2002
(Continued)

OTHER PUBLICATIONS

U.S. Appl. No. 61/468,990, filed Mar. 29, 2011.
(Continued)

*Primary Examiner* — Lauren P Farrar
(74) *Attorney, Agent, or Firm* — Baker & Hostetler LLP

(57) ABSTRACT

A cleaning device, system and method for use with an ETT or tracheostomy ventilation tube 60, a ventilator machine 900, a source(s) 602 of fluid (for example, pressurized or unpressurized) and a source(s) of suctioning 603 is disclosed. In some embodiments, the cleaning device is useful for cleaning an inner surface of the ventilation tube 60 and/or for preventing or hindering the accumulation of biofilm thereon. In some embodiments, it is possible to clean biofilm or any other material on the inner surface 201 by delivering fluid into an interior of the ventilation tube, wiping the tube interior with a width-expanded wiping element (e.g. an inflated balloon) by longitudinal motion of
(Continued)

the wiping element, and suctioning material out of the ventilation tube ventilation tube.

12 Claims, 60 Drawing Sheets

Related U.S. Application Data filed on Nov. 16, 2011, provisional application No. 61/468,990, filed on Mar. 29, 2011, provisional application No. 61/473,790, filed on Apr. 10, 2011, provisional application No. 61/483,699, filed on May 8, 2011, provisional application No. 61/496,019, filed on Jun. 12, 2011, provisional application No. 61/527,658, filed on Aug. 26, 2011, provisional application No. 61/603,340, filed on Feb. 26, 2012, provisional application No. 61/603,344, filed on Feb. 26, 2012, provisional application No. 61/609,763, filed on Mar. 12, 2012, provisional application No. 61/613,408, filed on Mar. 20, 2012.

(51) Int. Cl.
*A61M 16/04* (2006.01)
*A61M 16/08* (2006.01)
*A61M 25/00* (2006.01)

(52) U.S. Cl.
CPC .... *A61M 16/0456* (2014.02); *A61M 16/0459* (2014.02); *A61M 16/0465* (2013.01); *A61M 1/0058* (2013.01); *A61M 16/0858* (2014.02); *A61M 2025/0019* (2013.01); *A61M 2209/10* (2013.01)

(58) Field of Classification Search
CPC .......... A61M 16/0057; A61M 16/0465; A61M 16/0858; A61M 1/0058; A61M 2209/10; B08B 9/027; B08B 9/032
See application file for complete search history.

(56) References Cited

U.S. PATENT DOCUMENTS

| | | |
|---|---|---|
| 3,671,979 A | 6/1972 | Moulopoulos |
| 3,780,736 A | 12/1973 | Chen |
| 3,985,141 A | 10/1976 | Stanley et al. |
| 4,016,885 A | 4/1977 | Bruner |
| 4,064,882 A | 12/1977 | Johnson et al. |
| 4,134,407 A | 1/1979 | Elam |
| 4,159,722 A | 7/1979 | Walker |
| 4,166,468 A | 9/1979 | Haynie |
| 4,182,344 A | 1/1980 | Benson |
| 4,240,433 A | 12/1980 | Bordow |
| 4,245,639 A | 1/1981 | La Rosa |
| 4,324,262 A | 4/1982 | Hall |
| 4,351,328 A | 9/1982 | Bodai |
| 4,469,100 A | 9/1984 | Hardwick |
| 4,501,273 A | 2/1985 | McGinnis |
| 4,510,933 A | 4/1985 | Wendt et al. |
| 4,555,242 A | 11/1985 | Saudagar |
| 4,569,344 A | 2/1986 | Palmer |
| 4,583,917 A | 4/1986 | Shah |
| 4,606,347 A | 8/1986 | Fogarty et al. |
| 4,607,635 A | 8/1986 | Heyden |
| 4,630,606 A | 12/1986 | Weerda et al. |
| 4,638,539 A | 1/1987 | Palmer |
| 4,649,914 A | 3/1987 | Kowalewski |
| 4,691,702 A | 9/1987 | Chantzis |
| 4,758,223 A | 7/1988 | Rydell |
| 4,762,125 A | 8/1988 | Leiman et al. |
| 4,805,611 A | 2/1989 | Hodgkins |
| 4,813,935 A | 3/1989 | Haber et al. |
| 4,850,982 A | 7/1989 | Erlich et al. |
| 4,886,496 A | 12/1989 | Conoscenti et al. |
| 4,932,959 A | 6/1990 | Horzewski et al. |
| 4,946,440 A | 8/1990 | Hall |
| 4,961,738 A | 10/1990 | MacKin |
| 5,003,657 A | 4/1991 | Boiteau et al. |
| 5,029,580 A | 7/1991 | Radford et al. |
| 5,067,497 A | 11/1991 | Greear et al. |
| 5,073,164 A | 12/1991 | Hollister et al. |
| 5,098,384 A | 3/1992 | Abrams |
| 5,101,817 A | 4/1992 | Etter |
| 5,125,893 A * | 6/1992 | Dryden .............. A61M 16/0463 604/500 |
| 5,134,996 A | 8/1992 | Bell |
| 5,139,018 A | 8/1992 | Brodsky et al. |
| 5,181,908 A | 1/1993 | Bell |
| 5,188,618 A | 2/1993 | Thomas |
| 5,215,522 A | 6/1993 | Page et al. |
| 5,218,970 A | 6/1993 | Turnbull et al. |
| 5,254,098 A | 10/1993 | Ulrich et al. |
| 5,269,756 A | 12/1993 | Dryden |
| 5,277,177 A | 1/1994 | Page et al. |
| 5,279,549 A | 1/1994 | Ranford |
| 5,309,902 A | 5/1994 | Kee et al. |
| 5,325,851 A | 7/1994 | Reynolds et al. |
| 5,336,172 A | 8/1994 | Bales et al. |
| 5,337,730 A * | 8/1994 | Maguire ............ A61B 1/00091 600/157 |
| 5,349,950 A | 9/1994 | Ulrich et al. |
| 5,360,403 A | 11/1994 | Mische |
| 5,361,753 A | 11/1994 | Pothmann et al. |
| 5,364,345 A | 11/1994 | Lowery et al. |
| 5,364,358 A | 11/1994 | Hewitt et al. |
| 5,460,613 A | 10/1995 | Ulrich et al. |
| 5,487,383 A | 1/1996 | Levinson |
| 5,490,503 A | 2/1996 | Hollister |
| 5,545,179 A | 8/1996 | Williamson, IV |
| 5,582,161 A | 12/1996 | Kee |
| 5,611,336 A | 3/1997 | Page et al. |
| 5,634,937 A | 6/1997 | Mollenauer et al. |
| 5,694,922 A | 12/1997 | Palmer |
| 5,709,691 A * | 1/1998 | Morejon ............. A61M 1/0078 128/207.14 |
| 5,715,815 A | 2/1998 | Lorenzen et al. |
| 5,730,123 A | 3/1998 | Lorenzen et al. |
| 5,738,091 A | 4/1998 | Kee et al. |
| 5,743,258 A | 4/1998 | Sato et al. |
| 5,775,325 A | 7/1998 | Russo |
| 5,779,687 A | 7/1998 | Bell et al. |
| 5,832,920 A | 11/1998 | Field |
| 6,045,531 A | 4/2000 | Davis |
| 6,082,361 A | 7/2000 | Morejon |
| 6,227,200 B1 | 5/2001 | Crump et al. |
| 6,270,489 B1 | 8/2001 | Wise et al. |
| 6,318,368 B1 | 11/2001 | Morejon |
| 6,494,208 B1 | 12/2002 | Morejon |
| 6,602,219 B2 | 8/2003 | Madsen et al. |
| 6,612,304 B1 | 9/2003 | Cise et al. |
| 6,647,984 B1 | 11/2003 | O'Dea |
| 6,679,262 B1 | 1/2004 | Morejon |
| 6,805,125 B1 | 10/2004 | Crump et al. |
| 6,918,893 B2 | 7/2005 | Houde et al. |
| 6,923,184 B2 | 8/2005 | Russo |
| 6,932,788 B2 | 8/2005 | Kamiyama et al. |
| 6,935,339 B2 | 8/2005 | Mattar Neto et al. |
| 6,976,974 B2 | 12/2005 | Houde et al. |
| 7,021,313 B1 | 4/2006 | Crump et al. |
| 7,051,737 B2 | 5/2006 | Kolobow et al. |
| 7,060,135 B2 | 6/2006 | Morejon |
| 7,156,827 B2 | 1/2007 | McNary et al. |
| 7,172,572 B2 | 2/2007 | Diamond et al. |
| 7,179,272 B2 | 2/2007 | Kieturakis et al. |
| 7,188,623 B2 | 3/2007 | Anderson et al. |
| 7,191,782 B2 | 3/2007 | Madsen |
| 7,204,252 B2 | 4/2007 | Johnson |
| 7,273,473 B2 | 9/2007 | Owens et al. |
| 7,278,429 B2 | 10/2007 | Johnson |
| 7,383,736 B2 | 6/2008 | Esnouf |
| 7,478,636 B2 | 1/2009 | Madsen et al. |

(56) References Cited

U.S. PATENT DOCUMENTS

| | | |
|---|---|---|
| 7,556,041 B2 | 7/2009 | Madsen |
| 7,625,207 B2 | 12/2009 | Hershey et al. |
| 7,669,600 B2 | 3/2010 | Morejon |
| 7,717,116 B2 | 5/2010 | Mijers |
| 7,726,315 B2 | 6/2010 | Field |
| 7,775,206 B2 | 8/2010 | Anderson et al. |
| 7,789,893 B2 | 9/2010 | Drasler et al. |
| 7,819,890 B2 | 10/2010 | Russo et al. |
| 7,854,728 B2 | 12/2010 | Boyle, Jr. |
| 7,878,202 B2 | 2/2011 | Anderson et al. |
| 7,967,811 B2 | 6/2011 | Kumar |
| 8,002,732 B2 | 8/2011 | Visconti |
| 8,133,326 B2 | 3/2012 | Bracken |
| 8,157,919 B2 | 4/2012 | Vazales et al. |
| 8,210,168 B2 | 7/2012 | Swisher |
| 8,215,306 B2 | 7/2012 | Brewer et al. |
| RE43,886 E | 1/2013 | Mijers |
| 8,381,345 B2 | 2/2013 | Vazales et al. |
| 8,382,908 B2 | 2/2013 | Vazales et al. |
| 8,397,577 B2 | 3/2013 | Slocum, Sr. et al. |
| 8,414,544 B2 | 4/2013 | Resca |
| 8,434,488 B2 | 5/2013 | Li et al. |
| 8,458,844 B2 | 6/2013 | Vazales et al. |
| 8,468,637 B2 | 6/2013 | Vazales et al. |
| 8,486,100 B2 | 7/2013 | Oishi et al. |
| 8,534,287 B2 | 9/2013 | Vazales et al. |
| 8,556,851 B2 | 10/2013 | Hirszowicz et al. |
| 8,557,054 B2 | 10/2013 | Morejon |
| 8,601,633 B2 | 12/2013 | Vazales et al. |
| 8,631,798 B2 | 1/2014 | Varga et al. |
| 8,783,255 B2 | 7/2014 | Maguire et al. |
| 8,999,074 B2 | 4/2015 | Zachar et al. |
| 9,010,322 B2 | 4/2015 | Swisher |
| 9,095,286 B2 | 8/2015 | Vazales et al. |
| 9,119,926 B2 | 9/2015 | Cuevas et al. |
| 9,131,988 B2 | 9/2015 | Bagwell et al. |
| 9,220,859 B2 | 12/2015 | Li et al. |
| 9,248,249 B2 | 2/2016 | Li et al. |
| 9,332,891 B2 | 5/2016 | Vazales et al. |
| 9,352,112 B2 | 5/2016 | Sederstrom et al. |
| 9,386,907 B2 | 7/2016 | Vazales et al. |
| 9,398,837 B2 | 7/2016 | Vazales et al. |
| 9,480,537 B2 | 11/2016 | Stadelman et al. |
| 2003/0145860 A1 | 8/2003 | Johnson |
| 2003/0188749 A1 | 10/2003 | Nichols et al. |
| 2003/0209258 A1 | 11/2003 | Morejon |
| 2003/0216698 A1 | 11/2003 | McNary et al. |
| 2004/0082923 A1 | 4/2004 | Field |
| 2004/0221851 A1 | 11/2004 | Madsen |
| 2004/0221852 A1 | 11/2004 | Madsen |
| 2005/0172971 A1 | 8/2005 | Kolobow et al. |
| 2005/0279359 A1 | 12/2005 | LeBlanc et al. |
| 2006/0005841 A1 | 1/2006 | Anderson et al. |
| 2006/0099434 A1 | 5/2006 | Hoetger |
| 2006/0130847 A1 | 6/2006 | Morejon |
| 2006/0150981 A1 | 7/2006 | Johnson |
| 2006/0207605 A1 | 9/2006 | Anderson et al. |
| 2006/0278235 A1 | 12/2006 | White et al. |
| 2007/0021651 A1 | 1/2007 | Gobel |
| 2007/0028924 A1 | 2/2007 | Madsen et al. |
| 2007/0038226 A1 | 2/2007 | Galdonik et al. |
| 2007/0089748 A1 | 4/2007 | Madsen et al. |
| 2007/0163599 A1 | 7/2007 | Mijers |
| 2007/0282250 A1 | 12/2007 | Anderson et al. |
| 2008/0011304 A1 | 1/2008 | Stewart |
| 2008/0035154 A1 | 2/2008 | Johnson |
| 2008/0047562 A1 | 2/2008 | Colburn et al. |
| 2008/0066746 A1 | 3/2008 | Nelson et al. |
| 2008/0114338 A1 | 5/2008 | Kumar |
| 2008/0121236 A1 | 5/2008 | Field |
| 2008/0167606 A1 | 7/2008 | Dann et al. |
| 2008/0210235 A1 | 9/2008 | Field et al. |
| 2009/0178681 A1 | 7/2009 | Bracken |
| 2009/0260632 A1 | 10/2009 | Abnousi et al. |
| 2009/0281483 A1 | 11/2009 | Baker et al. |
| 2009/0287151 A1 | 11/2009 | Resca |
| 2010/0010431 A1 | 1/2010 | Tulley |
| 2010/0036410 A1 | 2/2010 | Krolik et al. |
| 2010/0081896 A1 | 4/2010 | Swisher |
| 2010/0106102 A1 | 4/2010 | Ziebol et al. |
| 2010/0113916 A1 | 5/2010 | Kumar |
| 2010/0137899 A1 | 6/2010 | Razack |
| 2010/0147309 A1 | 6/2010 | Cuevas et al. |
| 2010/0147310 A1 | 6/2010 | Brewer et al. |
| 2010/0147312 A1 | 6/2010 | Brewer et al. |
| 2010/0170517 A1 | 7/2010 | Hackner |
| 2010/0186748 A1 | 7/2010 | Morejon |
| 2010/0199448 A1 | 8/2010 | Vazales et al. |
| 2010/0199999 A1* | 8/2010 | Vazales ............... A61B 1/126 128/207.14 |
| 2010/0307507 A1 | 12/2010 | Li et al. |
| 2010/0307508 A1 | 12/2010 | Li et al. |
| 2011/0023884 A1 | 2/2011 | Cuevas et al. |
| 2011/0023885 A1 | 2/2011 | Vazales et al. |
| 2011/0023886 A1 | 2/2011 | Vazales et al. |
| 2011/0023887 A1 | 2/2011 | Vazales et al. |
| 2011/0023888 A1 | 2/2011 | Vazales et al. |
| 2011/0180072 A1 | 7/2011 | Morejon |
| 2011/0186052 A1 | 8/2011 | Morejon |
| 2011/0197894 A1 | 8/2011 | Morejon |
| 2011/0247412 A1 | 10/2011 | Scott |
| 2011/0253145 A1 | 10/2011 | Calderoni et al. |
| 2012/0024293 A1 | 2/2012 | Maguire et al. |
| 2012/0090619 A1 | 4/2012 | Levine |
| 2012/0180791 A1 | 7/2012 | Ciccone |
| 2012/0204884 A1 | 8/2012 | Howard |
| 2012/0247479 A1 | 10/2012 | Varga et al. |
| 2012/0289893 A1 | 11/2012 | Chung |
| 2012/0296283 A1 | 11/2012 | Swisher |
| 2013/0014756 A1 | 1/2013 | Young et al. |
| 2013/0023729 A1 | 1/2013 | Vazales et al. |
| 2013/0030249 A1 | 1/2013 | Vazales et al. |
| 2013/0035628 A1 | 2/2013 | Garrison et al. |
| 2013/0046332 A1 | 2/2013 | Jones et al. |
| 2013/0112207 A1 | 5/2013 | Roth |
| 2013/0146063 A1 | 6/2013 | Sederstrom et al. |
| 2013/0218071 A1 | 8/2013 | Resca |
| 2013/0228196 A1 | 9/2013 | Vazales et al. |
| 2014/0012074 A1 | 1/2014 | Vazales et al. |
| 2014/0020682 A1 | 1/2014 | Li et al. |
| 2014/0033455 A1 | 2/2014 | Vazales et al. |
| 2014/0090194 A1 | 4/2014 | Stadelman et al. |
| 2014/0090195 A1 | 4/2014 | Stadelman et al. |
| 2014/0090642 A1 | 4/2014 | Bagwell et al. |
| 2014/0142496 A1 | 5/2014 | Zachar et al. |
| 2014/0150782 A1 | 6/2014 | Vazales et al. |
| 2014/0196721 A1 | 7/2014 | Gilhuly |
| 2014/0246015 A1 | 9/2014 | Einav et al. |
| 2014/0283875 A1 | 9/2014 | Vazales et al. |
| 2014/0290649 A1 | 10/2014 | Maguire et al. |
| 2015/0133864 A1 | 5/2015 | Zachar et al. |
| 2015/0190597 A1 | 7/2015 | Zachar et al. |
| 2015/0209536 A1 | 7/2015 | Roth |
| 2015/0335842 A1 | 11/2015 | Cuevas et al. |
| 2015/0343182 A1 | 12/2015 | Vazales et al. |
| 2016/0082212 A1 | 3/2016 | Li et al. |
| 2016/0121066 A1 | 5/2016 | Zachar et al. |
| 2016/0193011 A1 | 7/2016 | Vazales et al. |
| 2016/0193439 A1 | 7/2016 | Zachar et al. |
| 2016/0199608 A1 | 7/2016 | Morejon |
| 2016/0250431 A1 | 9/2016 | Sederstrom et al. |
| 2016/0287834 A1 | 10/2016 | Bennett |
| 2017/0106160 A1 | 4/2017 | Zachar |
| 2017/0189589 A1 | 7/2017 | Zachar et al. |
| 2017/0326317 A1 | 11/2017 | Zachar |

FOREIGN PATENT DOCUMENTS

| | | |
|---|---|---|
| EP | 2928517 A1 | 10/2015 |
| GB | 2482618 A | 2/2012 |
| JP | 2009504240 A | 2/2009 |
| WO | WO8907466 A1 | 8/1989 |
| WO | WO9403226 A1 | 2/1994 |
| WO | WO9938548 A2 | 8/1999 |

(56) References Cited

FOREIGN PATENT DOCUMENTS

| WO | WO03101516 | A1 | 12/2003 |
|---|---|---|---|
| WO | WO2006099434 | A1 | 9/2006 |
| WO | WO2007024288 | A1 | 3/2007 |
| WO | 2007/141787 | A1 | 12/2007 |
| WO | WO2007146613 | A2 | 12/2007 |
| WO | WO2010091309 | A1 | 8/2010 |
| WO | WO2011020985 | A1 | 2/2011 |
| WO | WO2011094517 | A1 | 8/2011 |
| WO | WO2011126812 | A1 | 10/2011 |
| WO | 2012087837 | A1 | 6/2012 |
| WO | WO2012131626 | A2 | 10/2012 |
| WO | WO2013030821 | A1 | 3/2013 |
| WO | WO2014089028 | A1 | 6/2014 |
| WO | WO2015187583 | A1 | 12/2015 |
| WO | 2017118970 | A1 | 7/2017 |
| WO | 2017199248 | A1 | 11/2017 |

OTHER PUBLICATIONS

U.S. Appl. No. 61/473,790, filed Apr. 10, 2011.
U.S. Appl. No. 61/483,699, filed May 8, 2011.
U.S. Appl. No. 61/496,019, filed Jun. 12, 2011.
U.S. Appl. No. 61/527,658, filed Aug. 26, 2011.
U.S. Appl. No. 61/539,998, filed Sep. 28, 2011.
U.S. Appl. No. 61/560,385, filed Nov. 16, 2011.
U.S. Appl. No. 61/603,340, filed Feb. 26, 2012.
U.S. Appl. No. 61/603,344, filed Feb. 26, 2012.
U.S. Appl. No. 61/609,763, filed Mar. 12, 2012.
U.S. Appl. No. 61/613,408, filed Mar. 20, 2012.
U.S. Appl. No. 61/635,360, filed Apr. 19, 2012.
U.S. Appl. No. 61/655,801, filed Jun. 5, 2012.
U.S. Appl. No. 61/660,832, filed Jun. 18, 2012.
U.S. Appl. No. 61/673,744, filed Jul. 20, 2012.
Search Report dated Nov. 2, 2011 which issued during the prosecution of GB Patent Application No. 2482618.
Machine Translation JP 2009504240 (by EPO and Google)—published Feb. 5, 2009; Kimberly-Clark Worldwide Inc.
Duguet A et al., "Control of tracheal cuff pressure: a pilot study using a pneumatic device," Intensive Care Med. Jan. 2007;33(1):128-32.
Maggiore SM et al., "Closed versus open suctioning techniques," Minerva Anestesiol. May 2002;68(5):360-4.
International Search Report for PCT/IL2012/000320, dated Nov. 15, 2012.
Written Opinion for PCT/IL2012/000320, dated Nov. 15, 2012.
International Search Report for PCT/IB2012/051532, dated Oct. 16, 2012.
Office Action for U.S. Appl. No. 14/596,905, dated Jul. 21, 2015.
Office Action for U.S. Appl. No. 13/806,958, dated Jun. 11, 2014.
Office Action for U.S. Appl. No. 13/806,958, dated Nov. 10, 2014.
Office Action together with the English translation dated Jan. 26, 2016, which issued during the prosecution Japanese Patent Application No. 2014-501798.
Office Action together with the English translation dated May 24, 2016, which issued during the prosecution of Japanese Patent Application No. 2014-526598.
European Search Report dated Jan. 14, 2016, which issued during the prosecution of Applicant's European App No. 12828334.
Examination Report dated Nov. 3, 2011 which issued during the prosecution of GB Patent Application No. 1116735.0.
Notice of Allowance Action dated Dec. 2, 2014, which issued during the prosecution of U.S. Appl. No. 13/806,958.
Novelty Search Report dated Sep. 16, 2011 which issued during the prosecution of Swedish Patent Application No. 179871.
Search Report dated Jun. 6, 2016, which issued during the prosecution of GB Patent Application No. 1600233.9.
Dwyer Instruments; Gage Fluid web page; https://web-beta.archive.org/web/20160306163019/http://www.dwyer-inst.com/Product/Miscella neous/Accessories/GageFluids/GageFluids; Mar. 6, 2016 [downloaded from world wide web May 27, 2017].
International Search Report and Written Opinion for PCT/IL2017/50284 dated Jun. 9, 2017.
International Search Report and Written Opinion for PCT/IL2016/51367 dated May 26, 2017.

\* cited by examiner

Prior Art - Cleaning Chamber
US patent 662219

Prior Art - US 7273474

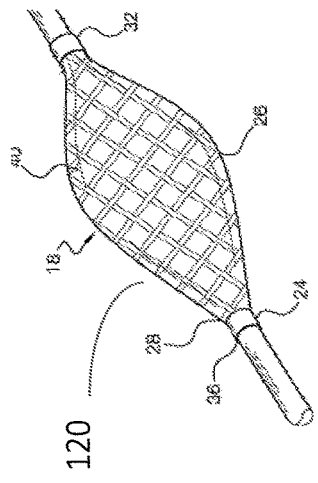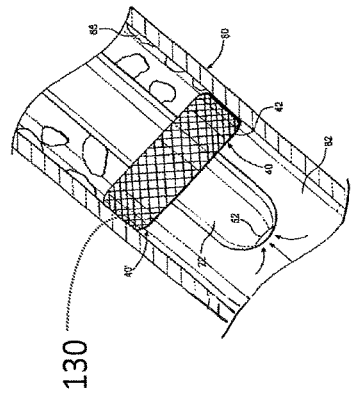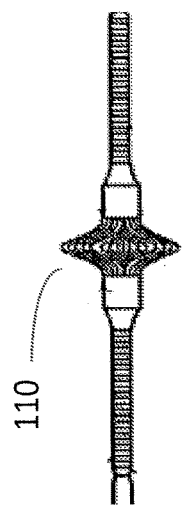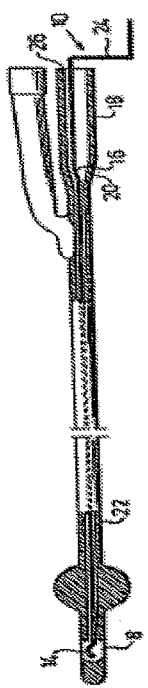
Fig. 2 (prior art)

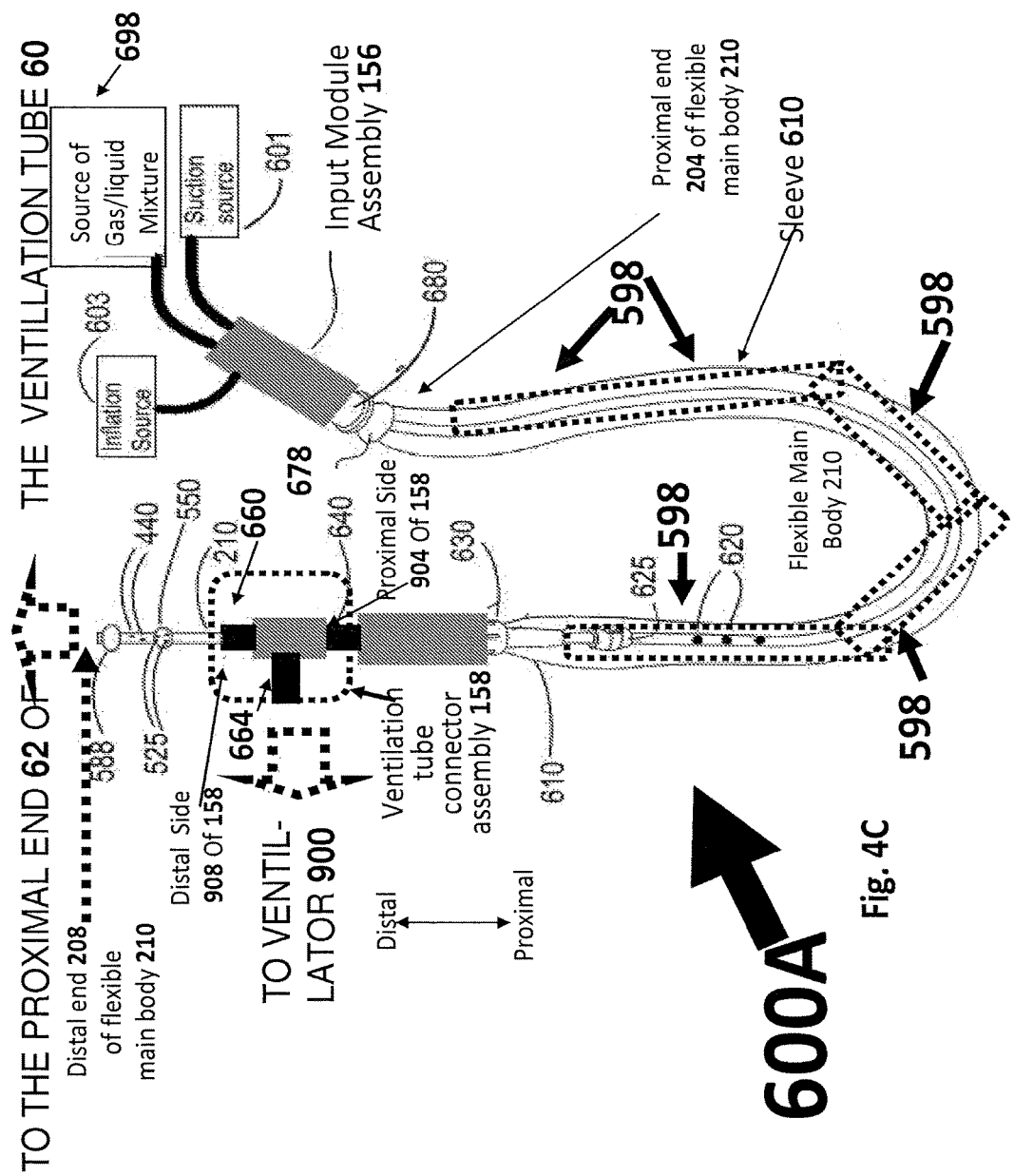

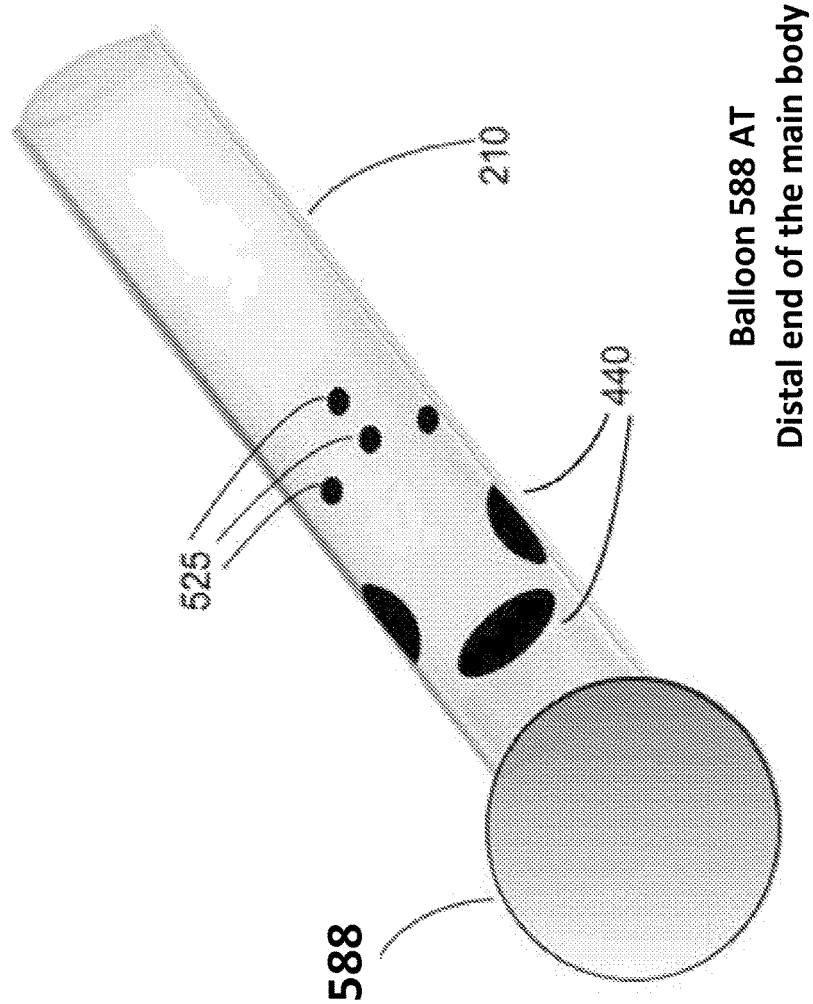

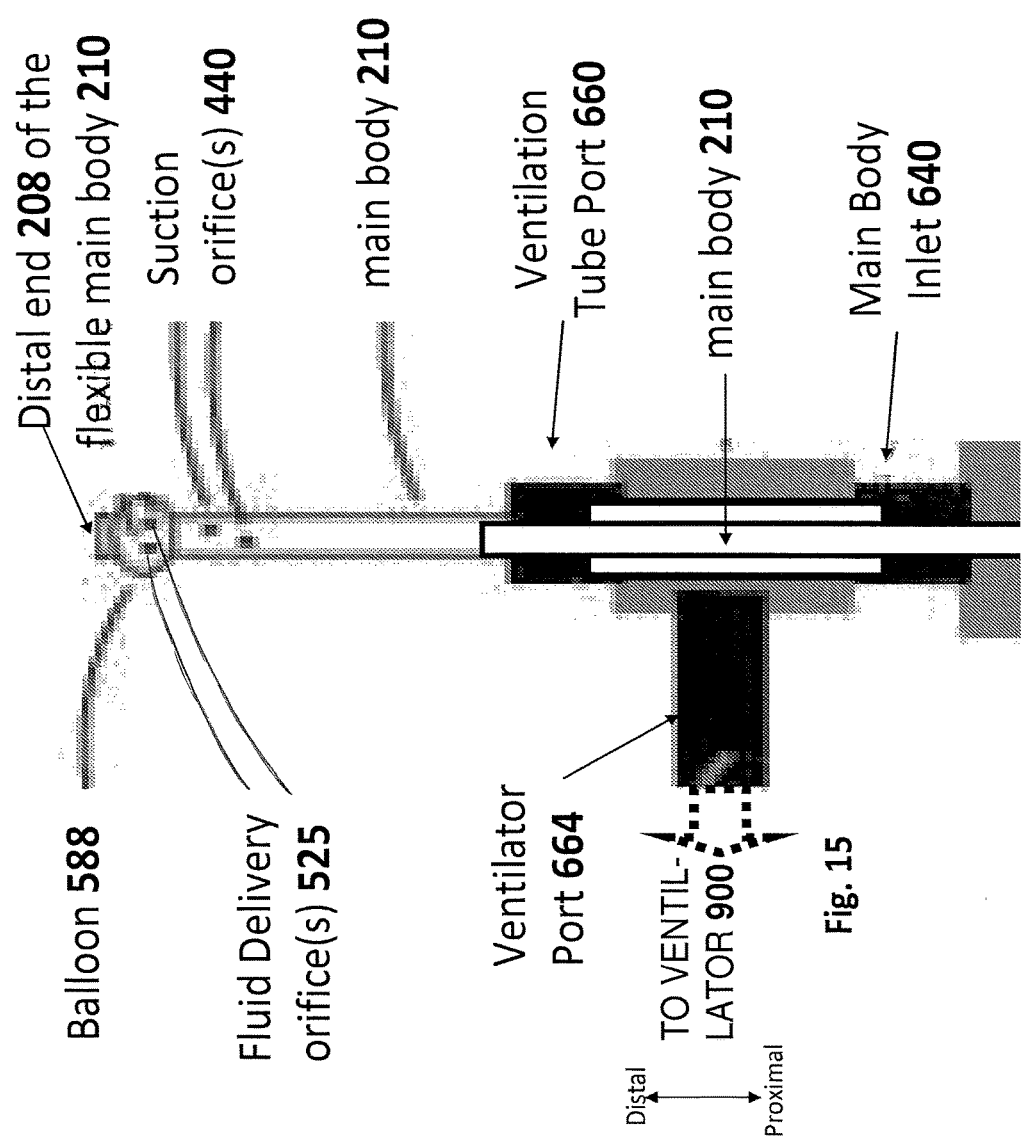

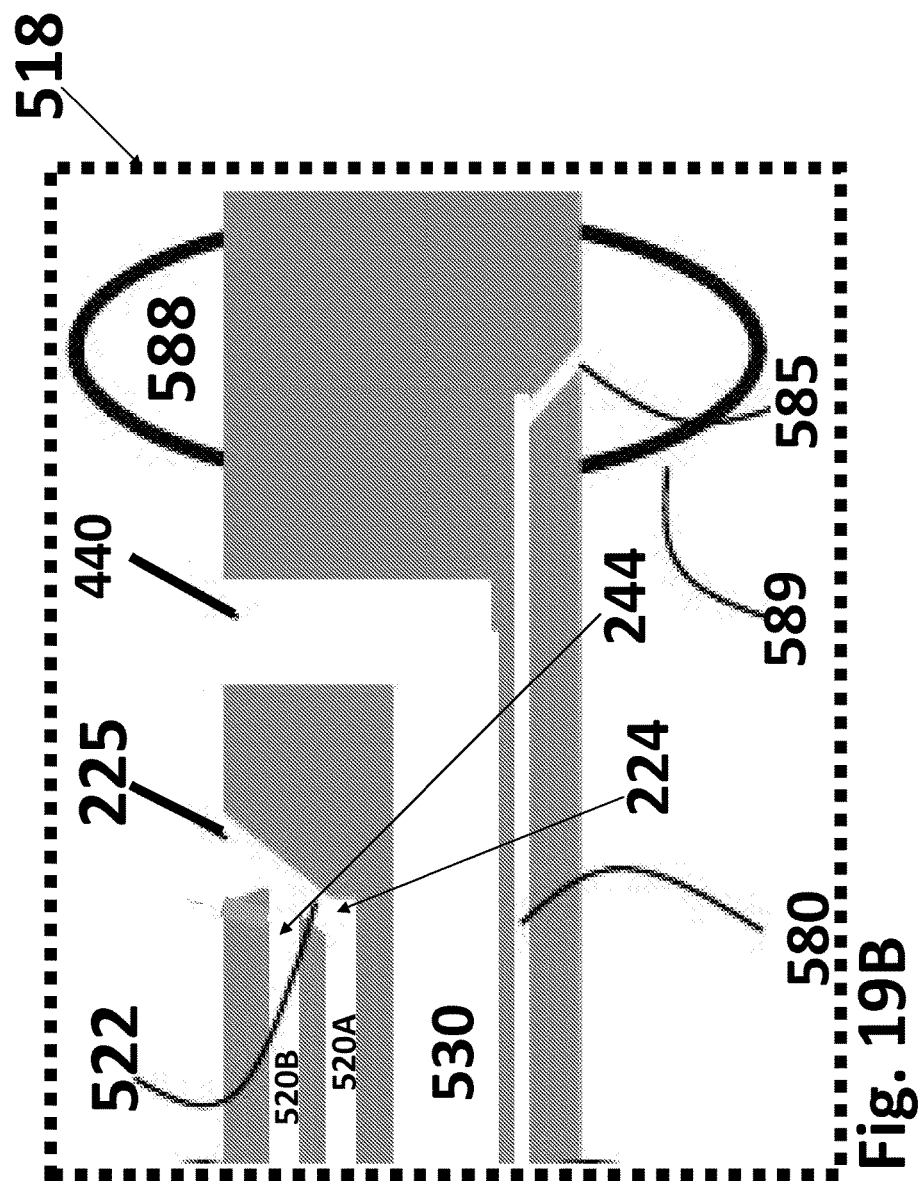

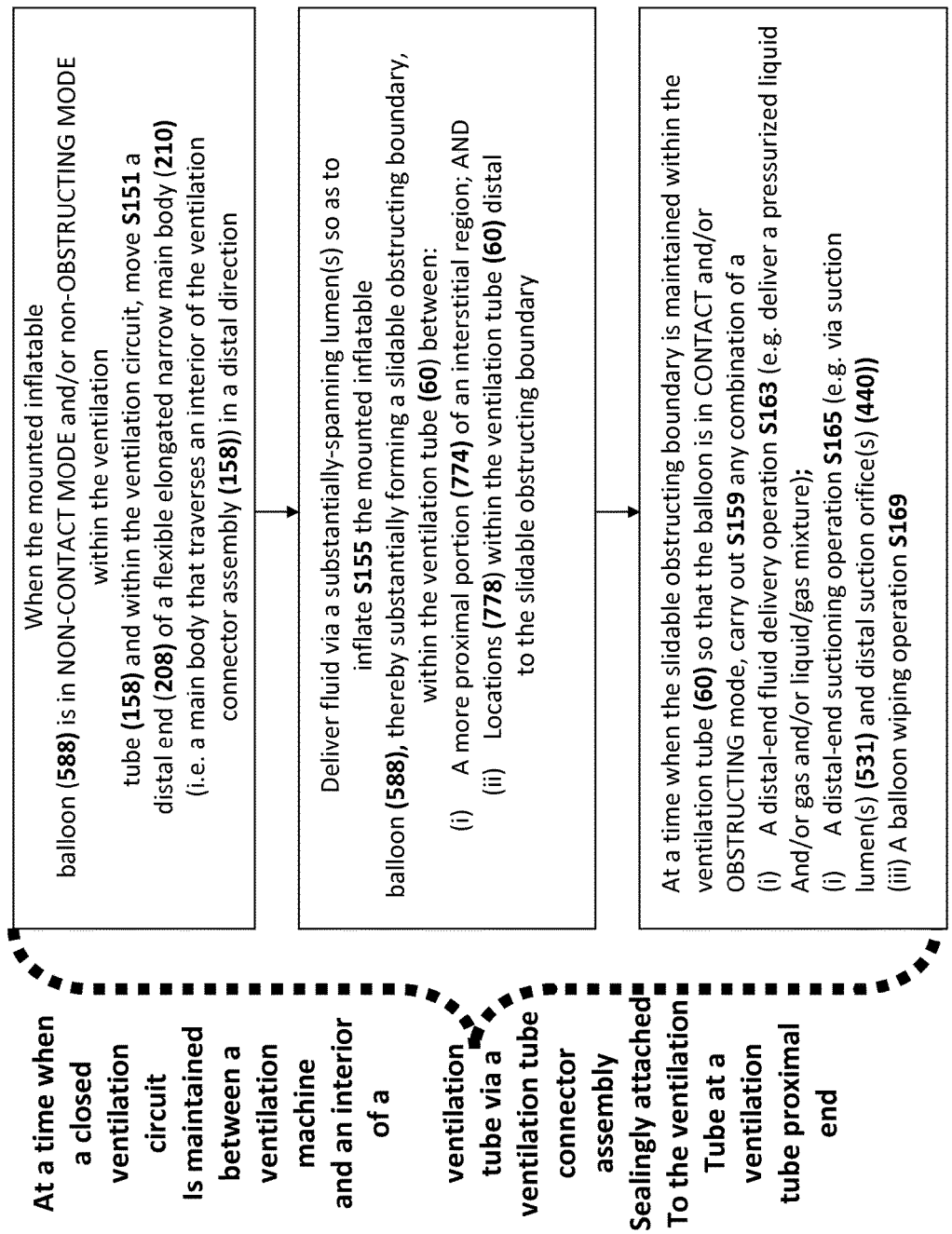

Cause PRESSURIZED FLUID (e.g. liquid and/or gas and/or liquid-gas mixture) (e.g. from a ventilation tube-external source (e.g. a continuous source) that is located outside of the ventilation tube)) to:

Enter S171, at a location outside of ventilation tube (60), into a substantially-spanning fluid-delivery lumen (520) that substantially spans a length of the elongated main body (210)

→

Travel S175 through the fluid-delivery lumen(s) (520) towards a distally-located orifice(s) (525) that is located near the distal end (208) of the elongated main body (210) but proximal to the inflatable balloon (588)

→

Exit S179 the fluid-delivery lumen (525) via distally-located orifice(s) (525) so as to deliver pressurized fluid (e.g. pressurized liquid and/or gas and/or liquid-gas mixture into the more proximal portion (774) of the interstitial region (e.g. so as to create a fluid stream 556 (e.g. liquid stream Or gas stream or stream of a liquid-gas mixture) within the more proximal portion (774)) – for example, to delivery a stream 556 of fluid incident upon an inner wall (201) of the ventilation tube (60) in the more proximal portion (774) near inflatable Balloon 588 and proximal to the sliding obstructing boundary

Fig. 28

BALLOONED VENTILATION TUBE CLEANING DEVICE

This application is a national phase of, and claims priority from, PCT Application No. PCT/IB12/51532, filed on Mar. 29, 2012, which is hereby incorporated by reference as if fully set forth herein

FIELD

Embodiments of present invention relates to devices, systems and methods of cleaning an interior of a ventilation tube and/or hindering the build-up of biofilm therein.

BACKGROUND AND RELATED ART

References Cited

US patent publication no. 2007/0038226;
US patent publication no. 2010/0137899;
US patent publication no. 2010/0186748 titled "Endotracheal Tube Cleaning Apparatus";
US patent publication no. 2010/023885;
U.S. Pat. No. 6,082,361;
U.S. Pat. No. 6,318,368;
U.S. Pat. No. 5,709,691;
WO 2011/094517;
US 2011/180072;
WO 2010/091309;
US 2006/099434;
US 2007/089748;
US 2007/024288;
U.S. Pat. No. 5,067,497;
PCT patent publication WO 89/07466;
PCT patent publication WO 2007/146613;
U.S. Pat. No. 5,125,893 titled "Suction catheter with wall lumen for irrigation";
U.S. Pat. No. 6,923,184 titled "Suction system with high efficiency suction control valve";
U.S. Pat. No. 7,051,737 titled "Mucus Shaving Apparatus for Endotracheal Tubes";
U.S. Pat. No. 7,669,600 titled "Endotracheal Tube Cleaning Apparatus";
U.S. Pat. No. 4,762,125 titles "Balloon-tipped suction catheter";
U.S. Pat. No. 4,351,328;
U.S. Pat. No. 5,738,091;
U.S. Pat. No. 6,602,219;
U.S. Pat. No. 6,612,304;
U.S. Pat. No. 6,805,125;
U.S. Pat. No. 6,935,339;
U.S. Pat. No. 7,273,473;
US patent application 20090178681

Suction catheters are commonly used to aspirate tracheabronchial fluids in patients ventilated with endo-tracheal tube (ETT) devices. A problematic aspect of the use of suction catheters is the presence of bacterial biofilm within the ETT lumen through which the suction catheter passes. Consequently, as the suction catheter is inserted, there is high risk of it carrying bacterial biofilm from the ETT lumen deeper into the bronchial tree where the suction catheter reaches, and thereby increasing the risk of lung infection. Moreover, buildup of substantial biofilm thickness reduces the effective free lumen of the ETT for air passage. Therefore, there is a need for maintaining cleaner ETT lumen between suction operations, and preventing buildup of significant biofilm thickness.

Another application is the use of cleaning catheters to clean the lumen of other catheters. An example of such cleaning catheter device is illustrated in FIG. 1c adapted from PCT patent publication WO 89/07466. These devices are mostly intended for the removal of substantial local clogging of the tube lumen. Yet such devices would be inefficient for cleaning of thin biofilm buildup on the lumen surface of medical device catheters such as endo tracheal tubes.

Prior art of ETT lumen cleaning devices include U.S. Pat. No. 7,051,737 titled "Mucus Shaving Apparatus for Endotracheal Tubes", and U.S. Pat. No. 7,669,600 titled "Endotracheal Tube Cleaning Apparatus", US patent publication no. 2010/0186748 titled "Endotracheal Tube Cleaning Apparatus", and references therein. Examples of prior art devices are provided in FIGS. 2a-2d.

The art of suction catheters is exemplified in U.S. Pat. No. 5,125,893 titled "Suction catheter with wall lumen for irrigation", U.S. Pat. No. 6,923,184 titled "Suction system with high efficiency suction control valve", and U.S. Pat. No. 4,762,125 titles "Balloon-tipped suction catheter".

The type of "closed suction systems" are where the suction catheter can be used repeatedly without being detached from the tube system including the ventilation air supply. Such types of systems are known in the art of suction catheters, as exemplified in the discussion of U.S. Pat. No. 6,923,184 and PCT patent publication WO 2007/146613, as well as U.S. Pat. Nos. 5,738,091, 6,602,219, 6,612,304, 6,805,125, 6,935,339, 7,273,473, US patent application 20090178681, and references therein (together "closed system art"). Representative prior art devices are illustrated in FIG. 1a and FIG. 1b. Such systems employ a tubing connector with at least two ports—one for air delivery and one for catheter delivery. U.S. Pat. No. 6,923,184 further discloses the option for cleaning the external surface of the catheter flexible shaft in a chamber located in front of the isolator seal of the multi-port tubing connector. The discussion of the closed system art patents is in the context of suction catheters.

Several problems plague present art devices: (a) The suction flexible shaft is coming up from the ETT with significant amount of bacterial rich slime drawn up bronchi; (b) the closed suction system needs to be replaced every about 48 h due to risk of bacterial proliferation on the flexible shaft exterior surface wall; (c) the ETT lumen cleaning operation is performed by a distinct catheter which requires disconnection of ventilation process and/or tube connection; (d) the ETT lumen cleaning sweeps up biofilm which itself require removal from the cleaning catheter, and this removal is done in a manual open way and not within a closed system.

SUMMARY OF EMBODIMENTS

Some embodiments of the present invention relate to a wiping device for cleaning an inner surface of a ventilation tube in a closed ventilation system where air is mechanically forced into the ventilation tube by an external ventilator. The wiping device includes an elongate flexible main body, an width-expandable wiping element (e.g. an inflatable balloon), one or more suction orifice(s) and one or more fluid delivery orifice(s).

In order to clean an inside surface of a ventilation tube, it is possible to carry out (e.g. simultaneously or in any order) a wiping operation, a fluid delivery operation and a suction operation. In some embodiments, during the wiping operation the width-expanded wiping element (e.g. the inflated balloon) moves longitudinally within the ventilation tube when in contact with an inner surface thereof—e.g. to wipe material located on the ventilation tube inner surface (e.g. biofilm). In some embodiments, during the fluid delivery operation, stream(s) of fluid (e.g. liquid stream(s) and/or gas stream(s) and/or stream(s) of a gas/liquid mixture for example a mist stream or a stream(s) of liquid including bubbles within) are sent, via the fluid delivery orifice(s), into the ventilation tube (e.g. incident upon an inner surface of the ventilation tube). In some embodiments, during the suction operation, material in the 'interstitial region' outside of the main body and within the ventilation tube is suctioned out of the ventilation tube.

Examples of suctioned material that may be suctioned out of the interstitial region include (i) derivatives of biofilm that has been wiped away from an inner surface, (ii) derivatives of fluid delivered into the interstitial region, and (iii) mixtures thereof.

Examples of ventilation tubes which may be cleaned include an endo-tracheal tubes (ETT) and tracheostomy ventilation tubes.

In some embodiments, a distal end of the flexible main body (i.e. of the 'closed system device') may be inserted into the ventilation tube via the ventilation tube proximal end at a time that a patient is being ventilated. In some embodiments, the flexible main body distal snuggly and slidably traverses an interior region of a ventilation tube assembly, which is mechanically coupled to a proximal end of the ventilation tube to form a substantially air-tight connection.

After insertion of a distal end of the elongate flexible main body into the ventilation tube (i.e. at a time that the main body traverses the interior of the ventilation tube assembly), an expandable wiping element (e.g. inflatable balloon) mounted to the elongate flexible main body (e.g. at or near a distal end thereof) is then caused to width-expand (e.g. by inflation with a liquid or gas or any combination thereof). In some embodiments, the width-expandable wiping element is expanded (e.g. by inflation) so as that a surface of the wiping element (e.g. balloon wall) is brought into contact with the ventilation tube inner surface.

As noted above, when the wiping element is in contact with the inner surface of the ventilation tube, it is possible to wipe away material located on the inner surface.

In some embodiments, width expansion of the width-expandable wiping element may be useful for creating a 'slidable boundary' which at least partially obstructs fluid communication between (i) a 'more proximal portion of the interstitial region' outside of the main body within the ventilation tube from (ii) more distal locations within the ventilation tube—i.e. a more distal portion of the interstitial region and/or locations in the ventilation tube that are distal of the balloon position. As will be discussed below, by at least partially obstructing fluid communication between the proximal and distal portions of the interstitial region (e.g. by balloon inflation) so as to 'significantly hinder' (but not necessarily completely prevent) this fluid communication, it is possible to introduce negative pressure (i.e. via suction orifice(s)) predominantly into the proximal portion of the interstitial region.

In this sense, even if the wiping element (e.g. balloon) does not completely prevent fluid communication between the more proximal and more distal portions of the tube interior, the expanded wiping element (e.g. inflated balloon) may hinder and/or at least partially obstructs such communications. Thus, in some embodiments, the width-expanded wiping element (e.g. inflated balloon) is 'boundary-forming' so as to form a boundary between the two regions (i.e. more proximal and more distal to the wiping element) of the interstitial region outside of the main body and within the ventilation tube. The 'boundary-forming' wiping element (e.g. balloon) which may or may not form a complete seal between the two regions.

Mechanical motion in a longitudinal direction (e.g. in a proximal direction) of the ventilation-tube-inner-surface-contacting width-expanded wiping element (e.g. inflated balloon) may wipe biofilm from the ventilation tube inner surface. The fluid delivery and the suction orifice(s) may respectively stream fluid into and suction material out of the more proximal portion of the interstitial region.

Outside of the ventilation tube and proximal to the ventilation tube connector assembly, a pliable and/or impermeable sleeve around at least a portion of the main body in location proximal to the tube connector assembly inhibits contamination (e.g. inhibits the transport of microbes from within the ventilation tube to an ambient environment or in the opposite direction). In some embodiments, the sleeve may be deployed around at least 5 cm or least 10 cm of the elongate flexible main body in locations proximal to the tube connector assembly. In some embodiments, the sleeve may be around at least a majority or at least a substantial majority that is at least 75%, or substantially an entirety of that is at least 90%, or an entirety of) the portion of the flexible main body that is proximal to the tube connector assembly and distal to a suction port in fluid communication with a suction orifice(s) (e.g. via a suction lumen(s)).

In some embodiments, the fluid delivery operation includes streaming fluid (e.g. including some sort of cleaning fluid such as water or saline solution or disinfectant solutions or mists thereof. The term 'fluid' broadly includes any combination of liquid and/or gas—in some embodiments, the fluid preferably includes at least some liquid for wetting) into the 'more proximal portion' of the interstitial region (e.g. so that fluid is incident upon the inner surface of the ventilation tube—for example, to wet the interior surface of the ventilation tube) via the fluid delivery port(s)—for example, located near the distal end of the main body and proximal to the inflatable balloon inflated in contact with the inner surface of the ventilation tube. A 'strength' or intensity or velocity of delivered fluid may depend on the degree to which the fluid is pressurized before delivery and/or on the size of the aperture through which the fluid is delivered and/or on other factors. In some embodiments, a jet of fluid (e.g. liquid and/or a liquid-gas mixture such as a mist or liquid containing bubbles) is incident upon an inner surface of the ventilation tube.

The delivered or streamed fluid may have sufficient linear momentum to be incident upon an inner surface of the ventilation tube. Material proximal to the balloon within the ventilation tube (e.g. including materials that was formerly biofilm and/or dirt and/or the delivered fluid) may, after being suctioned through the suction orifice, be proximally transported out of the ventilation tube within suction lumen(s) using negative pressure from the suction source.

A number of additional features are described herein.

According to a first example, the ballooned catheter device includes at least two balloons mounted and/or attached to the flexible main body (e.g. at or near the distal end of flexible main body): (i) the aforementioned inflatable 'wiping' and/or 'boundary forming' balloon which is inflated into contact with an inner surface of the ventilation tube (i.e. inflated by a liquid or gas) and/or is inflated to 'concentrate' suction into the proximal portion of the interstitial region; and (ii) a second balloon (referred to as the 'more proximal balloon') which may or may not be inflatable, is located proximal to the inflatable 'boundary-forming' or 'wiping' balloon, and which includes one or more of the fluid delivery ports.

In some embodiments, the inflatable 'boundary-forming' balloon is completely fluid-tight and substantially does not leak.

Alternatively, in a second example, the inflatable 'boundary-forming' balloon is not completely fluid-tight. According to this 'second' example, the balloon is inflated into contact with an inner surface 201 of ventilation tube 60 by liquid so to maintain balloon shape to contact the ventilation tube (i.e. for wiping) and/or so as to at least partially obstruct fluid communication within the tube. However, for the example where the 'boundary-forming balloon' is not fluid tight, some of the liquid within the balloon leaks into the 'more proximal portion' of the interstitial liquid via one or more relatively small holes in the surface of the inflatable 'boundary-forming' balloon. Although these hole(s) are small enough so as to allow the 'boundary-forming' balloon to maintain its shape and slidable contact with the ventilation tube inner surface (i.e. when receiving a relatively steady supply of pressurized liquid via the lumen(s)), the holes are large enough to allow liquid within the 'boundary-forming' inflatable balloon to stream into the more proximal section of the interstitial region—for example, so that a stream of fluid is incident upon the ventilation tube inner surface.

In this second example, the hole(s) function as the aforementioned 'fluid delivery ports' discussed herein. As will be discussed below, this embodiment may provide a number of safety features discussed below.

In some embodiments, the one or more 'fluid delivery ports' include a plurality of fluid delivery ports, and a 'multiple direction' feature is provided whereby fluid (e.g. liquid and/or gas and/or a liquid-gas mixture such as a mist or a bubble-containing-liquid) is simultaneously streamed into the 'more proximal' portion of the interstitial region in multiple directions. Towards this end, the catheter device may include (i) a first fluid delivery port disposed at a first location on a first side of the flexible main body; and (ii) a second fluid delivery port disposed at a second location substantially (e.g. within a tolerance of 75 degrees or more) on a second side of the flexible main body. Not wishing to be bound by any theory, it is noted that the streaming of fluid in substantially opposite directions may facilitate the cleaning of the ventilation tube inner surface.

A number of implementations of this 'multi-direction' feature are described herein. In a first implementation, the 'more proximal balloon' may include fluid delivery ports that face in different directions relative to an elongate or 'central' axis of the flexible main body. In a second implementation, the liquid-filled boundary-forming balloon that includes multiple 'small' holes. For example, it is possible to provide first and second holes that both face in a proximal direction but which face in substantially the opposite direction relative to the flexible main body central axis.

In a third implementation, the device includes a plurality of fluid delivery ports located substantially on a surface of the flexible main body. In some embodiments, a first of the fluid delivery ports faces in a first direction while a second of fluid delivery ports faces substantially in the opposite directions.

Some embodiments of the present invention relate to a multi-mode technique for operating the aforementioned ballooned catheter device in a closed system. In both modes of operation, the flexible main body is inserted into the ventilation tube via the proximal end of the ventilation tube and via an inner channel of a ventilation tube connector assembly that is sealingly connected to a proximal end of the ventilator tube.

In the first operating mode, a balloon-inner wall contact within the interstitial region is maintained by the inflatable balloon (e.g. so as to obstruct—i.e. significantly hinder—longitudinal flow between locations proximal and distal to the balloon), and the suction and fluid delivery orifice(s) are operated as described above. The suction and fluid delivery orifice(s) are operated as described in one or more of the previous paragraphs so as to deliver fluid (e.g. a stream of liquid or a stream of a mist) into the 'more proximal portion' of the interstitial region while the slidable 'boundary' is maintained. A wiping operation caused by sliding the inflated balloon (i.e. inflated into contact with the ventilation tube inner surface) may be carried out simultaneous with or not simultaneous with the suction and fluid delivery operations.

In the second operating mode, the 'boundary-forming' balloon is deflated and/or not sufficiently inflated to contact the ventilation tube inner surface and/or not sufficiently inflated to at least partially obstruct (i.e. and 'significantly inhibit') fluid communication interstitial region into 'more proximal' and 'more distal' regions.

In the second mode of operation, suction provided by the suctioning port(s) may be used primarily to remove material from locations distal of the balloon (e.g. in the 'more distal' portion of the interstitial region or even from locations that are distal to the distal end of the ETT) and to transport this 'distally-located' material in a proximal direction out of the ETT. One example of such 'distally-located' material is tracheo-bronchial fluid or mucus located in the subject's trachea.

Some embodiments relate to a method of cleaning a main lumen of an ETT or tracheostomy ventilation tube 60 comprising: at a time when: (i) a ventilation tube connector assembly 158 mediates a substantially air-tight connection between a ventilator machine and an interior of a main lumen of the ventilation tube 60 (e.g. such that air is forced from the ventilator machine through the ventilation tube connector assembly 158 into the main lumen of the ventilation tube 60); and/or (ii) an elongate, narrow, flexible, main body 210 (e.g. of a length that is at least 15 cm) slidably and internally traverses the ventilation tube connector assembly 158 without substantially breaking the substantially air-tight breathing circuit such that: A. a proximal end 204 of the main body 210 is located outside of the ventilation tube 60 proximal to the ventilation tube connector assembly 158; and B. a boundary-forming balloon 588 mounted to the elongate, flexible main body 210 is located within the ventilation tube 60, and/or (iii) at least a portion of the main body is a connection-assembly-proximal-portion 598 that is located proximal to the ventilation tube connector assembly 158; and/or (iv) at least 5 cm of the connection-assembly-proximal-portion 598 is covered and/or enveloped by a substantially impermeable pliable sleeve; carrying out the following steps: A. effecting a balloon-inflation operation by forcing a fluid from outside of the ventilation tube 60 into the boundary-forming balloon 588 so that inflation of the boundary-forming balloon 588 obstructs (i.e. significantly hinders) fluid flow to forms a slidable boundary 770 between: I. a more proximal portion 774 of an interstitial region outside of the flexible main body and within the ventilation tube; and II. locations 778 within the ventilation tube 60 that are distal to slidable boundary 770, the slidable boundary 770 being located in a distal half of the ventilation tube 60; A. concurrent with a maintaining of the slidable boundary 770, effecting a fluid delivery operation by forcing a pressurized fluid from outside of the ventilation tube 60 into the more proximal portion 774 of the interstitial region through one or more fluid delivery orifice(s) 525 that is: I. mechanically coupled to the flexible main body 210; II. located proximal of the slidable boundary 770 and longitudinally closer to the slidable boundary 770 location than to a proximal opening of the ventilation tube; C. concurrent with the maintaining of the slidable boundary 770, proximally suctioning, out of the ventilation tube 60, material located: I. within the more proximal portion 774 of the ventilation tube 60; II. in the distal half of the ventilation tube, via one or more suction orifice(s) 440 that is: I. mechanically coupled to the flexible main body 210; and II. located proximal of the slidable boundary and longitudinally closer to the slidable boundary 770 location than to a proximal opening of the ventilation tube.

In some embodiments, the one or more suction orifice(s) is(are) longitudinally displaced from the slidable boundary 770 and/or to a midpoint of the boundary-forming balloon 588 by at most a suction-orifice-displacement-value that is at most 3 cm.

In some embodiments, i. the pressurized fluid (e.g. pressurized liquid or a pressurized mist or a pressurized bubble-containing liquid) is simultaneously forced through first 525A and second 525B fluid delivery orifices to respectively produce first 556A and second 556B fluid streams that are respectively and simultaneously incident upon an inner surface 201 of the ventilation tube 60 at first 552A and second 552B locations; and ii. the first 552A and second 552B locations are substantially on opposite sides of the ventilation tube 60 inner surface 201 within a tolerance that is at most 75 degrees.

In some embodiments, each fluid-delivery-orifice is proximally displaced from the slidable boundary 770 and/or from a midpoint of the boundary-forming balloon 588 by at most a fluid-orifice-displacement-value that is at most 3 cm, or at most 2 cm.

In some embodiments, the fluid-orifice-displacement-value that is at most 2 cm.

In some embodiments, the tolerance is at most 45 degrees or at most 25 degrees.

In some embodiments, the first 525A and second 525B fluid delivery orifices are respectively supplied via first 520A and second 520B fluid-delivery lumens.

In some embodiments, the first 520A and second 520B second fluid delivery lumens are simultaneously supplied by a common pressurized fluid chamber (e.g. containing pressurized liquid or another pressurized fluid such as a pressurized mist or bubbled liquid).

In some embodiments, immediately before exiting each fluid delivery orifice, the delivered fluid is pressurized to at least 1.5 atmospheres or at least 2 atmospheres or at least 3 atmospheres.

In some embodiments, each fluid delivery orifice 525 has a width of at most 3 mm or at most 2 mm or at most 1 mm, or at most 0.5 mm, at most 0.3 mm, at most 0.2 mm.

In some embodiments, each fluid delivery orifice 525 has width that is at most 50% of an average width of the 440 suction orifice(s).

In some embodiments, each fluid delivery orifice 525 has width that is at most 25% of an average width of the 440 suction orifice(s).

In some embodiments, each fluid delivery orifice 525 has width that is at most 10%, or at most 5%, of an average width of the 440 suction orifice(s).

In some embodiments, at a time that the slidable boundary is maintained, substantially no suction or suction at a significantly lower proximal air flow rate than the suction of step C is applied to locations distal of the slidable boundary.

In some embodiments, the suction-orifice-displacement-value is at most 2 cm or at most 1 cm or at most 0.5 cm.

In some embodiments, the ventilation tube 60 is an ETT. In some embodiments, the ventilation tube 60 is a tracheostomy tube.

In some embodiments, the fluid delivery operation and the suctioning are carried out simultaneously.

In some embodiments, the fluid delivery operation and the suctioning are carried out sequentially.

In some embodiments, the method further comprises: concurrent to the maintaining of the slidable boundary, longitudinally moving the boundary-forming balloon 588 so as to mechanically dislodge and/or loosen biofilm material located on the inner surface 201 of the ventilation tube 60.

In some embodiments, the longitudinal moving is carried out simultaneously with the fluid delivery operation and/or the suctioning.

In some embodiments, at least one of the fluid delivery orifice(s) 525 are deployed to and/or voids within a second balloon 586 deployed distal to the boundary-forming balloon 588.

In some embodiments, the second balloon 586 is inflatable.

In some embodiments, the second balloon 586 is not inflatable.

In some embodiments, at least one of the at least one of the fluid delivery orifice(s) 525 is an inner-surface-facing void in the main body 210 facing towards the inner surface 201 of the ventilation tube 60 or a inner-surface-facing-void in a fluid-delivery lumen 520 that at least spans a longitudinal range between the fluid delivery orifice(s) 525 and a location on or within the main body 210 that is proximal to the ventilation tube connector assembly 158.

In some embodiments,
i. at least one of the at least one of the fluid delivery orifice(s) 525 is a void in the boundary-forming balloon 588 so that the boundary-forming balloon 588 is leaky;
ii. forcing of pressurized liquid into the boundary-forming balloon 588 is operative to carry out at least some of both of the balloon-inflation operation and the fluid-delivery of the fluid-delivery operation.

In some embodiments, a surface of the boundary-forming balloon 588 is at least 90% or at least 95% and/or at most 99% by surface area, substantially impermeable.

In some embodiments, the boundary-forming 588 balloon is substantially sealed and is not leaky.

In some embodiments, the method further comprises carrying out the additional step of: D. concurrent with the maintaining of the ventilation circuit, and at a time that the boundary-forming balloon 588 mounted to the elongate, flexible main body 210 is located within the ventilation tube 60 and in a non-obstructing or so that the slidable boundary (i.e. for significantly hindering fluid flow within the ventilation tube 60) with the inner surface 201 of the ventilation tube 60 is not maintained and/or non-contact mode so that balloon 588 is not inflated into contact with the inner surface 201 of ventilation tube 60, proximally suctioning into the suction orifice(s) 440 material that is located: I. within the ventilation tube 60 and distal to the boundary-forming balloon 588; and/or II. distal to the ventilation tube distal end 60 so that the material located distal to the ventilation tube distal end 60 enters an interior region of ventilation tube 60 en route to the suction orifice(s), wherein the suctioning step when the boundary-forming balloon 588 is in non-obstructing and/or non-contact mode is carried out to proximally transport material suctioned in step D proximally out of ventilation tube 60 via a proximal opening of the ventilation tube 60.

Some embodiments relate to a—system ballooned cleaning system comprising: a. an ETT or tracheostomy ventilation tube 60; b. a ventilator machine; c. ventilation tube connector assembly 158 directly or indirectly connected to both the ventilation tube 60 and the a ventilator machine so as to mediate a substantially air-tight connection between the ventilator machine and an interior of the ventilation tube; d. an elongate, narrow, flexible, main body 210 of a length that is at least 15 cm (or at least 20 cm or at least 25 cm or at least 30 cm); e. a boundary-forming balloon 588 mounted to the elongate, flexible main body 210, the main body configured to slidably and internally traverse the ventilation tube connector assembly 158 without substantially breaking the air-tight connection between the ventilator machine and an interior of the ventilation tube such that: I. a proximal end 204 of the main body 210 is located outside of the ventilation tube 60 proximal to the ventilation tube connector assembly 158; and II. the mounted boundary-forming balloon 588 is located in the ventilation tube 60; the boundary-forming balloon 588 being configured so that, when the mounted boundary-forming balloon 588 is located in the ventilation tube 60, inflation of the boundary-forming balloon 588 forms a slidable boundary between: I. a more proximal portion 774 of an interstitial region outside of the flexible main body and within the ventilation tube; and II, locations 778 within the ventilation tube 60 that are distal to slidable boundary, f. a plurality of fluid-communication lumens located within and/or along the elongate, flexible main body 210 including one or more suction lumen(s) 530 and one or more fluid delivery lumen(s) 520; g. one or more fluid delivery orifice(s) 525 that: I. is(are) mechanically coupled to flexible main body 210 so that longitudinal motion of the flexible main body 210 induces longitudinal motion of the fluid delivery orifice(s) (e.g. so the orifice(s) move closer towards a; II. is located proximal to the slidable boundary when the boundary-forming balloon 558 is inflated into contact with an inner surface of tube 60 to form a slidable 'boundary'; h. one or more suction orifice(s) 440 that: I. is(are) mechanically coupled to flexible main body 210 so that longitudinal motion of the flexible main body 210 induces longitudinal motion of the fluid delivery orifice(s); II. is located proximal to the slidable boundary when the boundary forming balloon 558 is inflated to form the slidable boundary; i. a source of pressurized fluid (e.g. located outside of the ventilation tube 60) and operative, at least some of the time and concurrent with the maintaining of the slidable boundary, to deliver pressurized fluid into more proximal portion 774 of the interstitial region such that the pressurized fluid travels to the fluid delivery orifice(s) 525 via the fluid delivery lumen(s) 520 and enters into the more proximal portion 774 of the interstitial region via the fluid delivery orifice(s) 525; and j. a suction source 603 located outside of the ventilation tube 60, and operative, at least some of the time and concurrent with the maintaining of the slidable boundary, to proximally transport material located within the more proximal portion 774 of the interstitial region out of the ventilation tube 60 such that the transported material exits the more proximal portion 774 of the interstitial region via the suction orifice(s) 440, enters into suction lumen(s) 530 and proximally exits the ventilation tube within suction lumen(s) 530.

In some embodiments, boundary-forming balloon 588 is mounted to the main body 210 at a location in a distal half (or third or quarter or fifth or tenth) of the main body 210.

In some embodiments, the fluid source (e.g. 602 and/or other examples) and the suction source 603 are respectively operative, in combination with the lumens and the orifices, to effect the fluid delivery and the suctioning when the boundary-forming balloon 588 is located in a distal half of the ventilation tube 60.

Some embodiments closed-system ballooned cleaning system for use with an ETT or tracheostomy ventilation tube 60, a ventilator machine, a source of pressurized fluid and a source of suctioning 603, the cleaning system comprising: a. a ventilation tube connector assembly 158 operative, when directly or indirectly connected to both the ventilation tube 60 and the ventilator machine, to mediate a substantially air-tight mediating connection between the ventilator machine and an interior of the ventilation tube via an interior of the ventilation tube connector assembly 158; b. an elongate, narrow, flexible, main body 210 of a length that is at least 15 cm (or at least 20 cm or at least 25 cm or at least 30 cm); c. a boundary-forming balloon 588 mounted to the elongate, flexible main body 210, the flexible main body operative to slidably and internally traverse the ventilation tube connector assembly 158 without substantially breaking the air-tight connection between the ventilator machine and an interior of the ventilation tube such that: I. a proximal end 204 of the main body 210 is located outside of the ventilation tube 60 proximal to the ventilation tube connector assembly 158; and II. the mounted boundary-forming balloon 588 is located in the ventilation tube 60; the boundary-forming balloon 588 being configured so that, when the mounted boundary-forming balloon 588 is located in the ventilation tube 60, inflation of the boundary-forming balloon 588 forms a slidable boundary between: I. a more proximal portion 774 of an interstitial region outside of the flexible main body and within the ventilation tube; and II. locations 778 within the ventilation tube 60 that are distal to slidable boundary, f. a plurality of fluid-communication lumens located within and/or along the elongate, flexible main body 210 including one or more suction lumen(s) 530 and one or more fluid delivery lumen(s) 520; g. one or more distal fluid delivery orifice(s) 525 that: I. is(are) mechanically coupled to flexible main body 210 so that longitudinal motion of the flexible main body 210 induces longitudinal motion of the fluid delivery orifice(s); II. is located proximal to the slidable boundary when the boundary-forming balloon 558 is inflated to form the slidable boundary; h. one or more distal suction orifice(s) 440 that: I. is(are) mechanically coupled to flexible main body 210 so that longitudinal motion of the flexible main body 210 induces longitudinal motion of the fluid delivery orifice(s); II. is located proximal to the slidable boundary when the boundary forming balloon 558 is inflated to form the slidable bonudary; i. a rigid or resilient proximal fluid delivery port 827 in fluid communication with proximal interior location 829 within fluid delivery lumen(s) 520 that is proximal to the connector assembly 158, the proximal fluid delivery port 827 being configured, when directly or indirectly connected to the source of pressurized fluid (e.g. 602 or other example(s)), to mediate a substantially fluid-tight (e.g. liquid-tight) coupling between the source of pressurized fluid and the fluid delivery lumen proximal interior location 829 via an interior of the proximal fluid delivery port 827, the proximal fluid delivery port 827, the fluid delivery lumen(s) 520 and the fluid delivery orifice(s) 525 being operative so that pressurized fluid distally delivered from the source of pressurized fluid into the fluid delivery lumen(s) 520 via the proximal fluid delivery port 827 distally flows through the fluid delivery lumen(s) 520 to fluid delivery orifice(s) 525 and enters into the more proximal portion 774 of the interstitial region via the fluid delivery orifice(s) 525; and j. a proximal rigid or resilient suction port 830 in fluid (e.g. liquid) communication with proximal interior location 531 within suction lumen(s) 530 that is proximal to the connector assembly 158, the proximal suction port 830 being configured, when directly or indirectly connected to the suction source 603, to mediate a substantially air-tight coupling between the suction source 603 and the suction lumen proximal interior location 531 via an interior of the proximal suction port 830, the proximal suction port 830, the suction lumen(s) 530 and the suction orifice(s) 440 being operative so that negative pressure applied via the proximal suction port 830 causes material to exit the more proximal portion 774 of the interstitial region via the suction orifice(s) 440 and travel proximally to the suction lumen proximal interior location 531.

Some embodiments relate to a ballooned cleaning apparatus comprising: a. an elongate, narrow, flexible, main body 210 having length of at least 15 cm (or at least 20 cm or at least 25 cm or at least 30 cm); and a width of between 1 mm and 1 cm (for example, at least 3 mm and/or at most 6 mm—for example, between 3 and 6 mm); b. a boundary-forming balloon 588 mounted to the main body 210 in a distal half of the main body 210, the boundary-forming balloon 588 being inflatable so that when the balloon 588 is inserted into an enclosing tube having a diameter between 4 and 11 mm so that the balloon 588, inflation of the balloon 588 causes the balloon outer surface to contact an inner surface of the enclosing tube forms a slidable boundary between: I. a more proximal portion 774 of an interstitial region outside of the flexible main body and within the enclosing tube; and locations 778 within the ventilation tube 60 that are distal to the enclosing tube, c. a plurality of lumens located within and/or along the main body 210 including one or more suction lumen(s) 530 and one or more fluid delivery lumen(s) 520, each lumen of the plurality of lumens substantially spanning a length of the main body 210 between the proximal end 204 of main body 210 and boundary-forming balloon 588, each fluid delivery lumen(s) having an inner width of at most 3 mm (for example, at most 2 mm or at most 1 mm and/or at least 0.1 mm or at least 0.2 mm or at least 0.5 mm) each suction lumen(s) having an inner width of between 1 and 5 mm (for example, at least 2 mm and/or at least 5 mm) (for example, a ratio between an inner width of the suction lumen and an inner width of the fluid delivery lumen). at least one of the plurality of lumens in fluid communication with the inner surface of the balloon; d. one or more distal suction orifice(s) 440 that: i. have an inner width of between 1 and 5 mm; ii. is(are) mechanically coupled to flexible main body 210 so that longitudinal motion of the flexible main body 210 induces longitudinal motion of the fluid delivery orifice(s); iii. is located proximal to the slidable boundary when the boundary-forming balloon 558 is inflated to form the slidable boundary longitudinally displaced from the slidable boundary by at most 2 cm; e. one or more distal fluid delivery orifice(s) 525 that: i. have an inner width of at most 3 mm and at most 30% of the inner width of the distal suction orifice(s) 440; ii. is(are) mechanically coupled to flexible main body 210 so that longitudinal motion of the flexible main body 210 induces longitudinal motion of the fluid delivery orifice(s) 525; iii. is located proximal to the slidable boundary when the boundary-forming balloon 558 is inflated to form the slidable boundary and is longitudinally displaced from the slidable boundary by at most 2 cm.

In some embodiments, the flexible main body 210 includes a connection-assembly-proximal portion 598, at least 5 cm of which is covered and/or enveloped by a substantially impermeable pliable sleeve 610.

In some embodiments, a distal end of sleeve 610 is directly or indirectly attached to ventilation tube connector assembly 158—for example, so that the main body 210 may slide through the sleeve. In contrast, in some embodiments, a proximal end of sleeve 610 is configured to have a substantially fixed longitudinal position relative to a proximal end of elongate flexible main body 210.

BRIEF DESCRIPTION OF THE DRAWINGS

FIGS. 1-3 describe prior-art devices.
FIGS. 4-25 illustrate systems, apparatus and portions thereof for cleaning an inner surface of a ventilation tube and/or hindering accumulation of biofilm thereon according to some embodiments.
FIGS. 26-29 are flowcharts of methods for cleaning an inner surface of a ventilation tube according to some embodiments.

BRIEF DESCRIPTION OF EMBODIMENTS

Figure 1B:
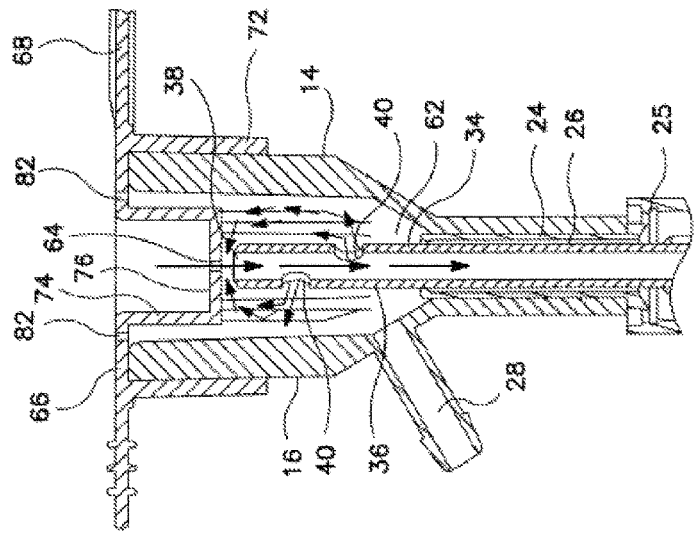

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only and are presented in the cause of providing what is believed to be a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

For brevity, some explicit combinations of various features are not explicitly illustrated in the figures and/or described. It is now disclosed that any combination of the method or device features disclosed herein can be combined in any manner—including any combination of features— any combination of features can be included in any embodiment and/or omitted from any embodiments.

Definitions

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

Some embodiments relate to a 'width' of an objection— for example, a 'width' of an elongate flexible main body 210 or a width of an orifice(s) or a width of a lumen. A 'width' is defined as the square root of the cross section.

A 'fluid' (e.g. a cleaning fluid) may refer to flowable liquid or liquid-gas mixture such as: (i) a liquid; (ii) a mist (e.g. droplets of liquid suspended within a gas such as air) or (iii) any other mixture of liquid and gas (for example, having a significant liquid content—e.g. a mist or bubbled liquid including gas bubbles). Some embodiments refer to delivering of a 'cleaning liquid 'or a 'source of pressurized liquid'—this is only one example. Any reference to a liquid (e.g. pressurized liquid, a liquid stream, a liquid lumen, a fluid delivery orifice, or other reference or combination thereof) may either refer to an actual liquid or to a gas-liquid mixture (e.g. a mist or any other gas-liquid mixture). 'Fluid communication' or 'liquid communication' refers to the ability of a liquid or a gas-liquid mixture to flow between two locations, and are used interchangeably. Throughout the present disclosure, a 'source of liquid' (e.g. pressurized liquid) and a 'source of fluid' (e.g. liquid or a liquid-gas mixture such as a mist) may be used interchangeably.

'Negative pressure' is suction—'negative pressure' and 'suction' are used interchangeably in the present disclosure.

A 'wiping element' is a 'wiper' and is used to wipe away material located on an inner surface 201 of ventilation tube 60. Examples of wiping elements include but are not limited to inflatable balloons, stents, and any other width-expandable object configured to wipe away material on the inner surface 201 of ventilation tube 60.

Some embodiments of the present invention relate to a wiping device for cleaning an inner surface of a ventilation tube in a closed ventilation system where an oxygen-including gas (e.g. air) is mechanically forced into the ventilation tube by an external ventilator. The wiping device includes an elongate flexible main body, an width-expandable wiping element (e.g. an inflatable balloon), one or more suction orifice(s) and one or more fluid delivery orifice(s).

In order to clean an inside surface of a ventilation tube, it is possible to carry out (e.g. simultaneously or in any order) a wiping operation, a fluid delivery operation and a suction operation. In some embodiments, during the wiping operation the width-expanded wiping element (e.g. the inflated balloon) moves longitudinally within the ventilation tube when in contact with an inner surface thereof—e.g. to wipe material located on the ventilation tube inner surface (e.g. biofilm). In some embodiments, during the fluid delivery operation, stream(s) of fluid (e.g. liquid stream(s) and/or gas stream(s) and/or stream(s) of a gas/liquid mixture for example a mist stream or a stream(s) of liquid including bubbles within) are sent, via the fluid delivery orifice(s), into the ventilation tube (e.g. incident upon an inner surface of the ventilation tube). In some embodiments, during the suction operation, material in the 'interstitial region' outside of the main body and within the ventilation tube is suctioned out of the ventilation tube.

FIGS. 4-6 and 8-22 relate to 'balloon embodiments' where the wiping element is an inflatable balloon 588. FIG. 23A-23B illustrate a non-balloon embodiment where the width-expanding wiping element is other than a balloon. Unless specified otherwise, it is possible to substitute an inflatable balloon with any other width-expandable wiping element.

Figure 4A:
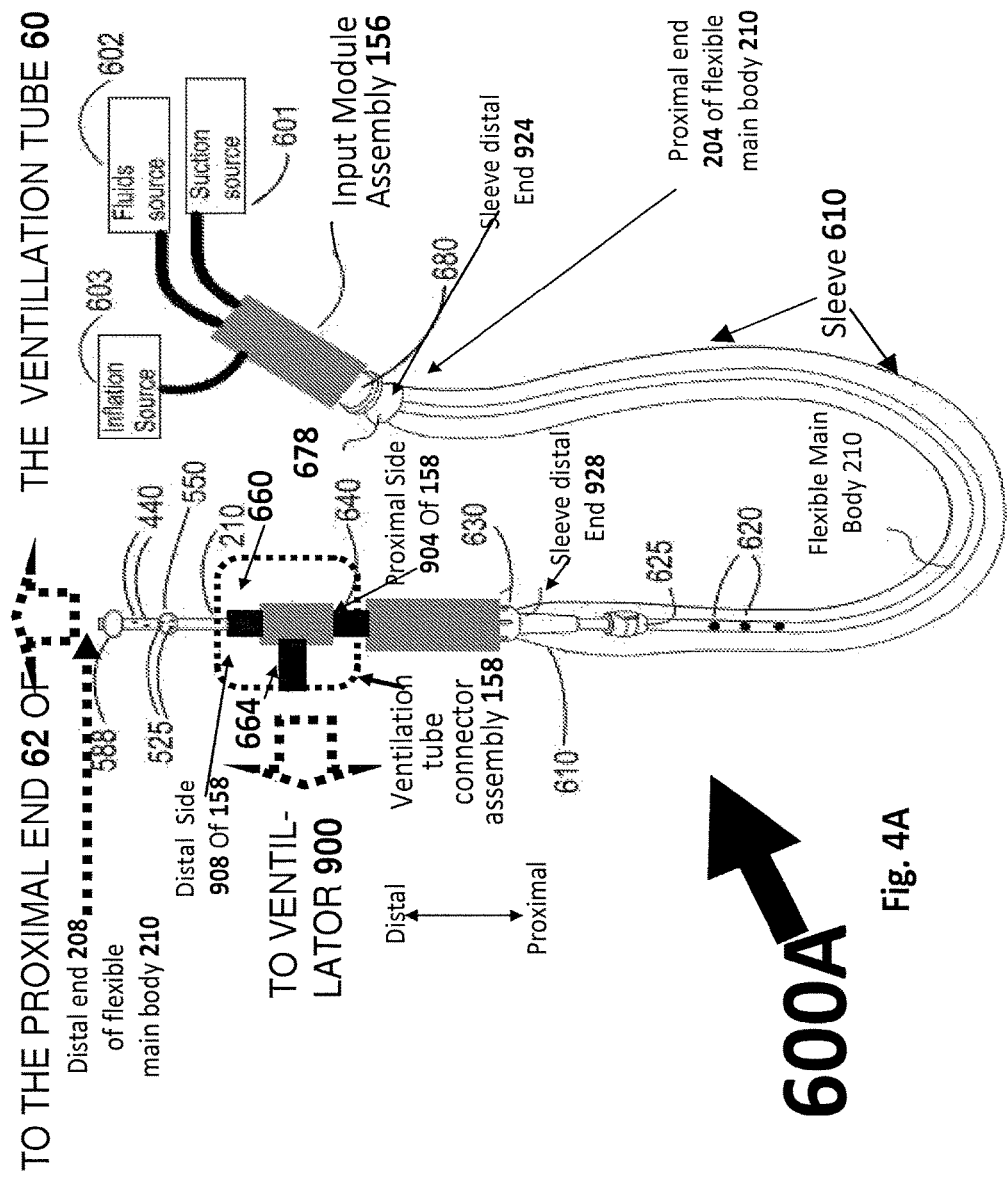

FIG. 4A illustrates a closed system cleaning system comprising: (i) an ETT or tracheostomy ventilation tube 60; (ii) a ventilator machine 900; (iii) a ventilation tube connector assembly 158 including a ventilator port 664, a ventilation tube port 660, and a main body inlet 640; and (iv) a flexible, elongate main body 210 having proximal 204 and distal 208 ends.

In some embodiments, the cleaning system is operative to clean an interior 201 of the ventilation tube 60 at a time when ventilation tube connector assembly 158 is directly or indirectly connected to both the ventilation tube 60 and the ventilator machine 900 so as to mediate a substantially air-tight connection (e.g. via an interior chamber(s) and/or conduit(s) of ventilation tube connector assembly 158) the between the ventilator machine and an interior of the ventilation tube. In one non-limiting example, an interior region and/or outer shape of ventilation tube port 660 matches a proximal end 62 of the ventilation tube 60 to create a substantial air-tight seal. In one non-limiting example, a tube or other conduit of a tube assembly (NOT SHOWN) may be connected to ventilator port 664 so that an interior of ventilator port 664 receives air from the ventilator machine and is in fluid communication with the ventilator machine 900 in a substantially air-tight manner.

In some embodiments, flexible, elongate main body 210 slidably and snugly passes through an interior of ventilation tube connector assembly 158 so that a proximal-distal direction of the main body 210 is aligned with a proximal-distal direction of the ventilation tube connector assembly 158—i.e. distal end 208 of flexible main body 208 is on a distal side 908 of ventilation tube connector assembly 158 and proximal end 208 of flexible main body 208 is on a proximal side 908 of ventilation tube connector assembly 158.

It is appreciated that when elongate main body 210 "snugly" passes through an interior of ventilation tube connector assembly 158 that there is no requirement for the fit between an outer surface of main body 210 and an interior of connector assembly 158 to be 'snug' in every location within connector assembly 158. In some embodiments, a 'snug fit' in one or more locations is sufficient to provide the 'snugly passing through' feature.

In some embodiments, flexible, elongate main body 210 slidably and snugly passes through the interior of ventilation tube connector assembly 158 in a manner that does not substantially break the substantially air-tight connection between the ventilator machine 900 and the interior of the ventilation tube 60.

The systems 600A-C of FIGS. 4-16 all include an inflatable 'boundary-forming balloon' 588, mounted to the flexible main body 200. When inflated, the boundary forming balloon, in some embodiments, may provide two types of functionality: (i) an 'flow obstruction functionality' to significantly hinder fluid flow between locations on opposite longitudinal sides of the boundary-forming balloon (as discussed below, this may be useful for 'concentrating' suction so that the suction is predominantly in a proximal portion 774); and (ii) a wiping functionality useful for cleaning the inner surface 201 of ventilator tube 60.

One salient feature of the ballooned cleaning apparatus provided by some embodiments is that the cleaning apparatus operates in a 'closed system' environment. During operation, it is possible to clean the inner surface 201 of ventilator tube 60 when the ventilation tube connector assembly 158-mediated substantially air-tight seal between (i) ventilator machine 900 and/or an interior of ventilator port 664 and (ii) an interior of ventilation tube 60 and/or an interior of ventilation tube port 660 is maintained—this substantially air-tight seal is referred to as the 'ventilation machine-ventilator tube' seal.

As will be discussed below, concurrent with a maintaining of this 'ventilation machine-ventilator tube' seal, it is possible to position the mounted balloon 588 within the ventilation tube 60 (e.g. in a distal half of ventilation tube 60) for example, by moving a distal end 208 of the main body 210 in a distal direction towards a distal end 64 of ventilation tube 60. For example, it is possible to distally move the mounted balloon 588 at a time when the mounted balloon 588 is in a 'non-contact state' (i.e. not in contact with an inner surface 201 of ventilation tube 60). After the boundary-forming balloon 588 is thus positioned, inflation of the balloon induces contact between an outer surface of the balloon 588 and an inner surface 201 of ventilation tube 60 and/or 'obstructs' (i.e. significant hinders) longitudinal flow between proximal 774 and distal 778 portions of the interior of ventilation tube 60. As will be disused below, this slidable 'boundary' between proximal 774 and distal 778 portions is useful for facilitating the cleaning of the inner surface 201—for example, for substantially confining locations of negative pressure and/or fluid (e.g. pressurized fluid such as pressurized liquid or pressurized fluid) introduced into an interstitial region outside of main body 210 and within ventilation tube 60 so that the suction or pressurized fluid is introduced 'predominantly' in a proximal portion 774.

In some embodiments, as illustrated in various figures (e.g. FIGS. 4A, 8, 14), inflatable "boundary forming" or 'inflated-into-contact-with-an-inner-surface-of-ventilation-tube' balloon 588 is mounted to flexible main body 210 at a location that is or near a distal end 208 or flexible main body 210.

In different embodiments, a location 'near a distal end' 208 of main body 210 may refer to: (i) in a distal half of flexible main body 210; or (ii) in a distal third of flexible main body 210, or (iii) in a distal fifth of flexible main body 210, or in (iv) a distal tenth of flexible main body 210.

Also shown in FIG. 4A is a second balloon 550 (which may or may not be inflatable) which is mounted to flexible main body 210 at a 'second balloon mounting location' that is proximal to a 'boundary-forming balloon mounting location' of the main body 210 to which "boundary forming" and/or 'inner surface-contacting' balloon 588 is mounted. In some embodiments, the 'second balloon mounting location' is 'near a distal end' 208 of main body 210—for example, in a distal half or third or fifth or tenth of flexible main body.

In the non-limiting example of FIG. 4A, second balloon 550 includes one or more fluid delivery orifice(s) 525 located on the surface of the second balloon 550. In other embodiments, the fluid delivery orifice(s) 525 may be located in other locations. (e.g. see FIG. 8 or 14). In various embodiments, fluid (e.g. liquid or mist or any gas/liquid mixture) delivered from source of pressurized liquid 602 into an interior of the ventilation tube 60 via fluid delivery orifice(s) 525 may be used to clean an inner surface 201 of ventilation tube 60. In the non-limiting example of FIG. 4A, fluid delivery orifice(s) 525 located on the surface of the second balloon 550—for example, as voids or holes in the surface of the second balloon 550. This is not a limitation, and in the examples of FIGS. 8 and 16 alternative configurations are illustrated.

Also illustrated in FIG. 4A are suction orifice(s) 440, which, in some embodiments, are supplied with negative pressure by suction source 601 and facilitate cleaning of the inner surface 201 of ventilation tube 60. In some embodiments, material within the interior of ventilation tube 60 may be suctioned into suction orifice(s) 440 and proximally transported out of ventilation tube 60—e.g. to a location that is proximal of ventilation tube connector assembly 158.

Figure 4B:
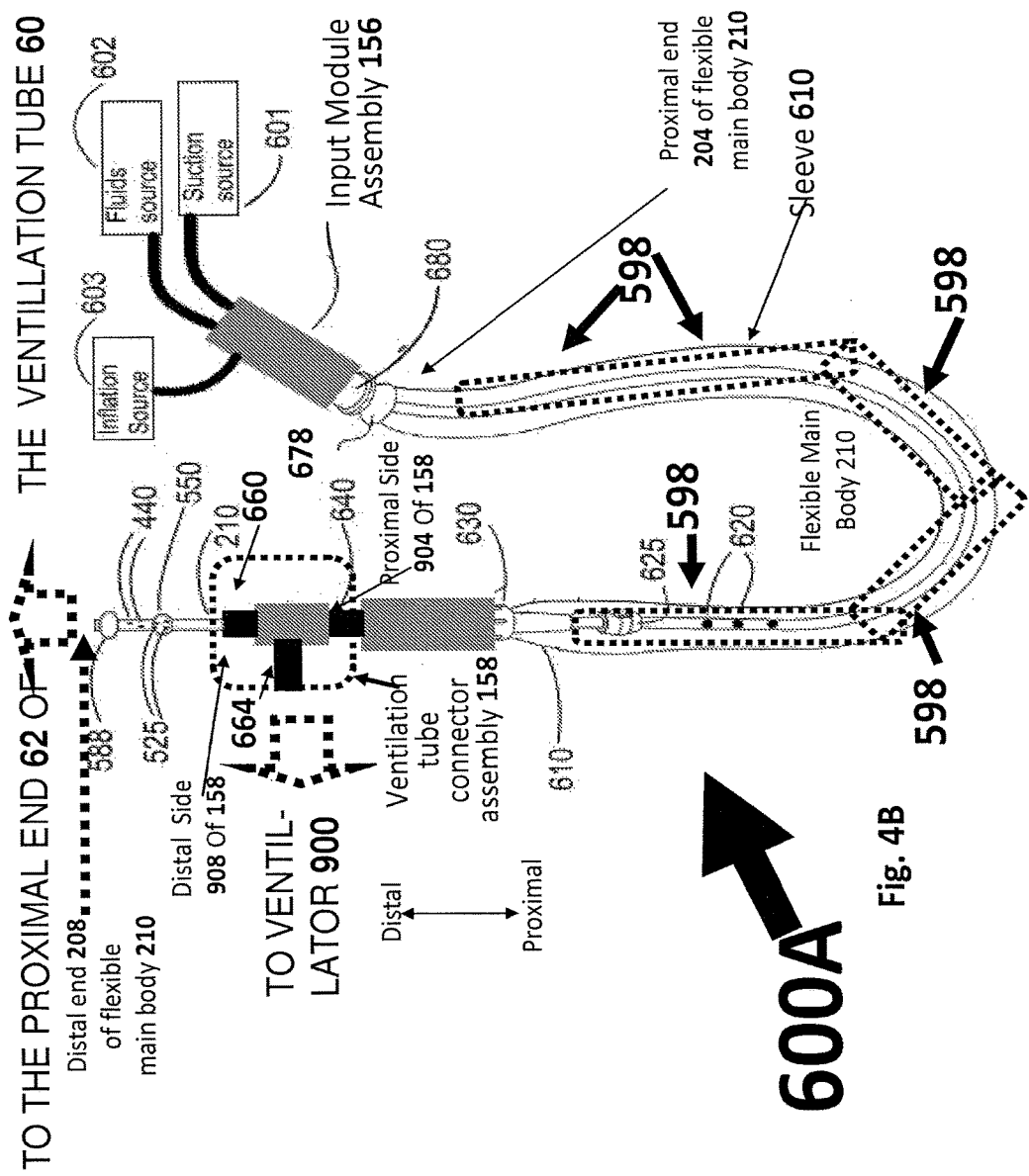

As will be discussed below, fluid communication between the suction source 601 and/or pressurized fluid source 602 and the suction 440 or fluid delivery 525 orifice(s) may be provided by one or more connecting lumen(s) within or along the main body 210/As As illustrated in FIGS. 4A-4B, at least a portion 598 of elongate main body 210 is located proximal to ventilation tube connector assembly 158. The magnitude of this 'portion' may depend on an extent to which distal end 208 and/or balloon 588 is deployed within ventilation tube 60 and/or an extent to which distal end 208 and/or balloon 588 is longitudinally displaced from ventilation tube connector assembly 158—for example, an extent to which the main body 210 slides through ventilation tube connector assembly 158 in a distal direction.

Because The system or method of FIGS. 4A-4B is a 'closed system,' in some embodiments, the system may include a substantially impermeable and/or pliable sleeve 610 for protecting an outer surface of main body 210. In some embodiments, sleeve 610 envelops and/or protects at least some (e.g. at least a majority or at least a substantial majority of at least 75% or substantially all of (i.e. at least 90%)) of an outer surface of the ventilation-tube-connector-assembly-proximal portion 598 of elongate main body 210. In some embodiments, sleeve 610 may provide this enveloping and/or protection functionality when a length of the ventilation-tube-connector-assembly-proximal portion 598 of main body 210 is at least 3 cm or at least 5 cm or at least 7 cm or at least 10 cm. As noted above, in some embodiments, a length of this proximal portion 598 may be modified by sliding, in a proximal or distal end, main body 210 through ventilation tube connector assembly 158.

In some embodiments, a distal end 908 of sleeve 610 is (i) directly or indirectly attached to and/or (ii) has a location that is fixed and/or longitudinally fixed relative to ventilation tube connector assembly 158. In some embodiments, a longitudinal position of a location of a distal end 908 of sleeve 610 corresponds to a location on ventilation tube connector assembly 158 (e.g. at or near main body inlet 640) and/or is longitudinally displaced from a proximal end (e.g. corresponding to main body inlet 640) of ventilation tube connector assembly 158 by at most 5 cm or at most 3 cm or at most 2 cm or at most 1 cm and/or at most 50% or at most 30% or at most 20% or at most 10% of a length of ventilation-tube-connector-assembly-proximal portion 598 of main body 210.

In some embodiments, a location of distal end 908 of sleeve 610 is not fixed relative to main body 210. For example, main body 210 may be longitudinally slidable within the sleeve 610 at or near a location of the distal end 908.

In some embodiments, a location of proximal end 904 of sleeve 610 is fixed and/or longitudinally fixed relative to a proximal end 204 of main body 210.

In some embodiments, sleeve 610 forms a substantially air-tight seal between the external environment and an outer surface of ventilation-tube-connector-assembly-proximal portion 598 of main body 210 and/or between the external environment and region of space outside of an outer surface of ventilation-tube-connector-assembly-proximal portion 598 of main body 210 and within sleeve 610.

Figure 1A:
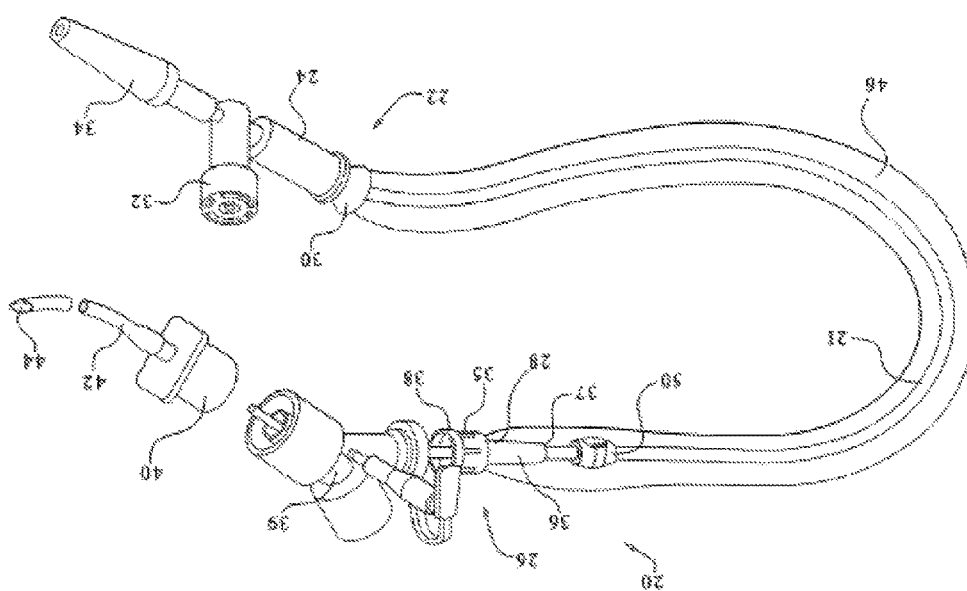
Figure 1C:
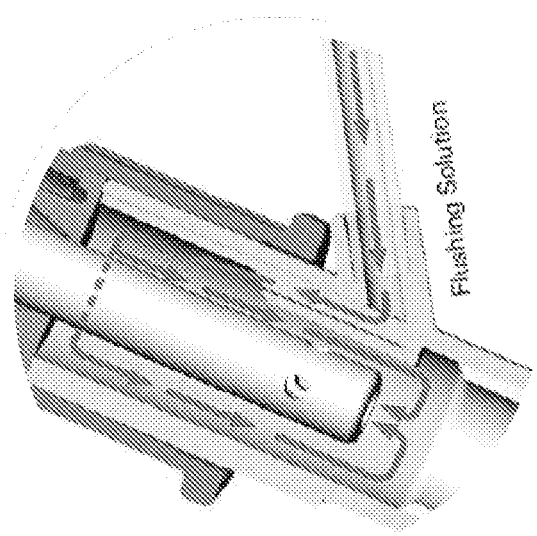
Figure 1D:
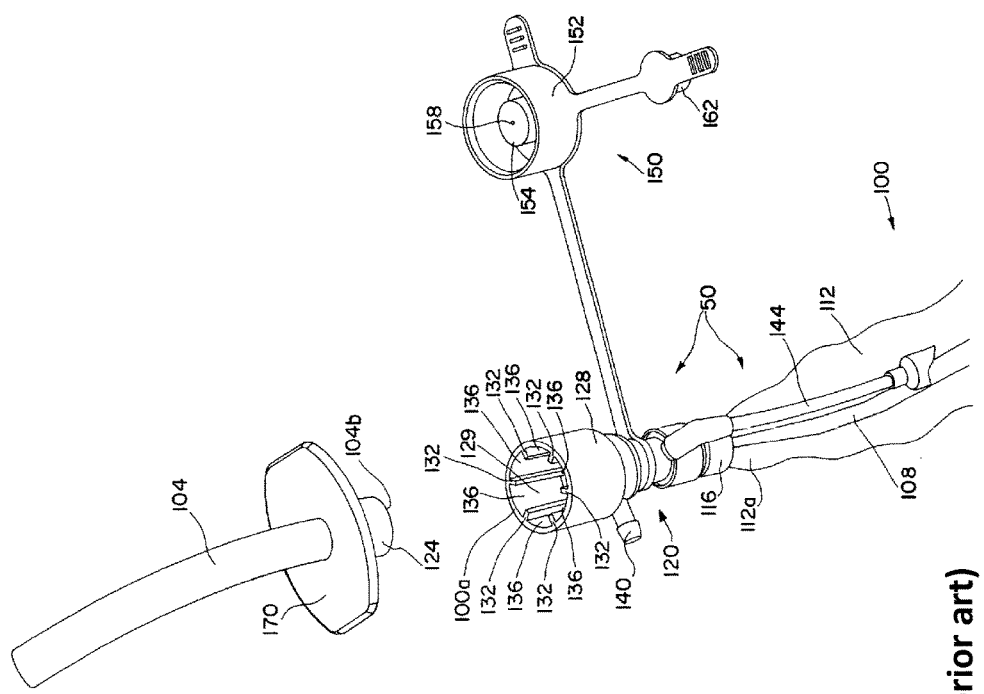
Figure 3A:
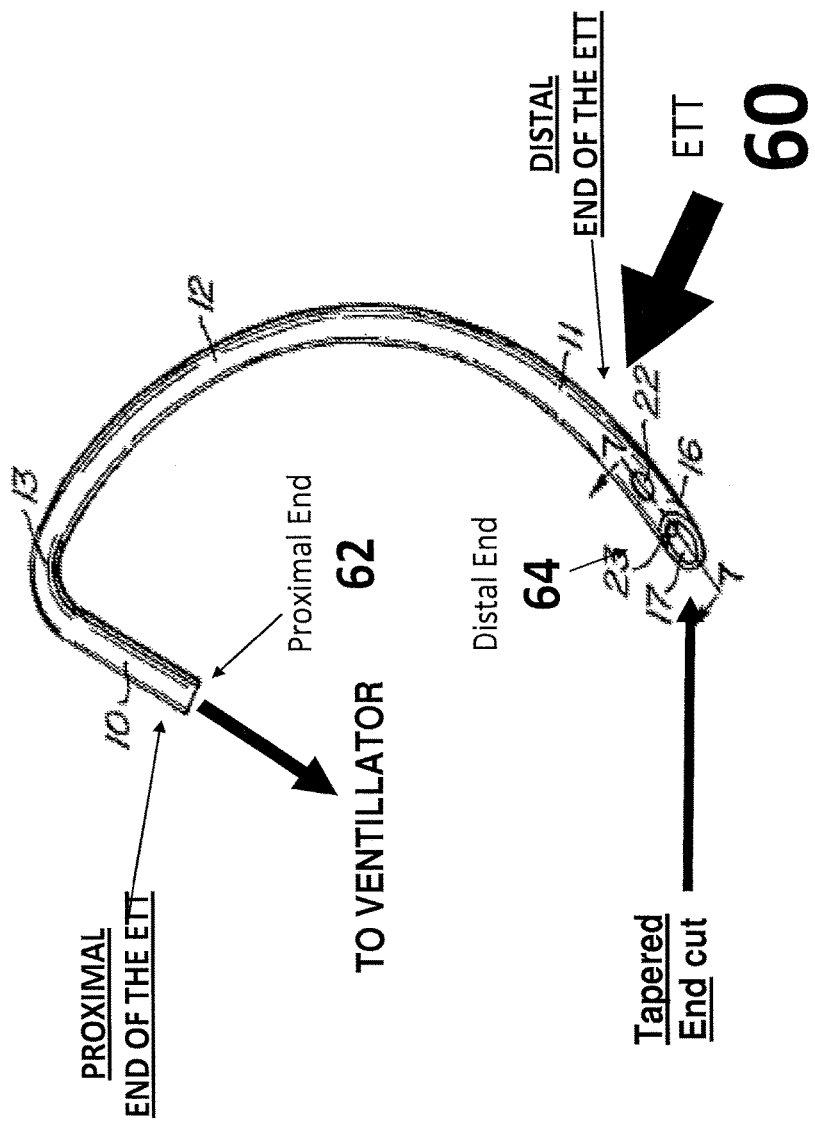
Figure 3B:
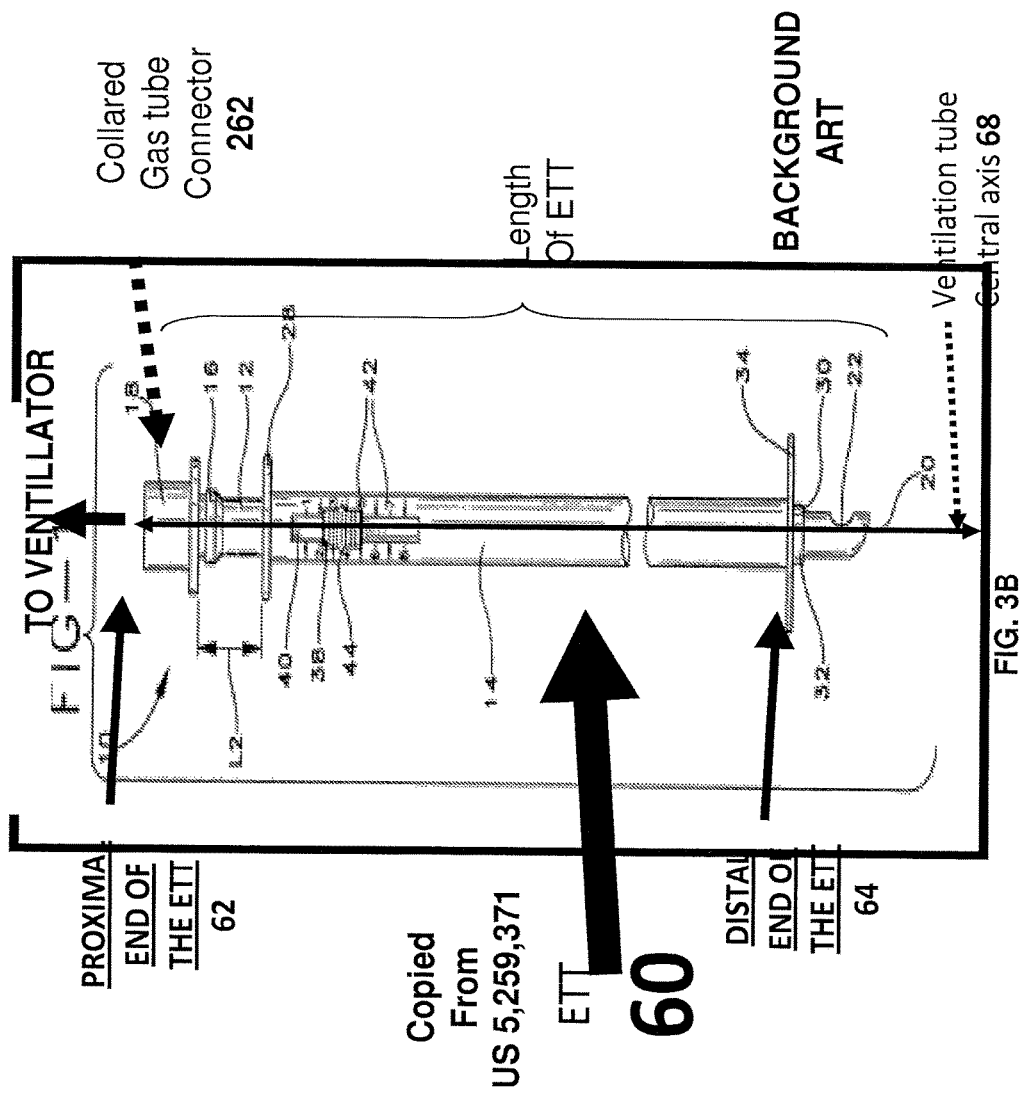

In the non-limiting example of FIG. 4A, an input module assembly 156 includes respective ports for interfacing: (i) with suction source 601 (i.e. suction port 820—for example, shaped as in element 34 of FIG. 1A or any other shape appropriate to function as a suction port), (ii) a source of pressurized fluid such as liquid or mist or any gas-liquid mixture under pressure (i.e. a port for receiving pressurized fluid from 602), and (iii) inflation source 603 (i.e. a port for receiving a gas flow or liquid flow from 603—for balloon inflation). Suction source 601 provides negative pressure for suctioning material out of an interior of ventilation tube 60 (e.g. material formerly attached to an interior surface 201 of ventilation tube 60—e.g. as biofilm)—e.g. via suction orifice(s) 440.

In some embodiments, pressurized fluid from source 602 forced, via a fluid delivery lumen 520 (not shown in FIGS. 4A-4B) may enter, via fluid delivery orifice(s) 525, into an interstitial region inside of the ventilation tube 60 and outside of the main body 210. In some embodiments, a stream of the delivered fluid passes through an interstitial region en route to the inner surface 201 of ventilation tube 60, and is incident upon the ventilation tube inner surface 201. Delivery of the fluid (e.g. liquid or mist or any liquid-gas mixture) into the interstitial region and/or to the inner surface 201 may be useful for cleaning the ventilation tube inner surface 201.

In some embodiments, pressurized liquid or gas delivered from inflation source 603 is delivered to boundary-forming inflatable balloon 588 inflate boundary-forming balloon 588 (e.g. to form a slidable boundary as will be discussed below).

In the non-limiting example of FIGS. 4A-4B, the fluids source 602 (e.g. source of pressurized liquid or mist or any gas/liquid mixture) and the inflation source 603 are illustrated as two separate elements. This is not a limitation. In other embodiments (see, for example, FIG. 14) the source of pressurized liquid 602 may be used to both inflate boundary-forming balloon 588 and to delivery fluid via fluid delivery orifice(s) 525.

FIGS. 4A-4B refer to the example where a source of fluids (e.g. liquid or any other liquid-gas mixture) is 'external' and may either be a source of liquids or a source of other fluids such as gas-liquid mixtures (e.g. mist). In the example of FIG. 4C, a gas/liquid mixture source (e.g. a pressurized gas/liquid mixture) 698 is explicitly illustrated and may be external to device 600.

In the example of FIGS. 4A-4B the source of liquid 602 and/or source of a gas/liquid mixture (i.e. 602 or 698) are 'external' to the device—the cleaning device receives either liquid or a mixture of liquid and gas (e.g. via one or more ports). In some embodiments, the received fluid (e.g. liquid and/or gas) is pressurized.

Figure 4D:
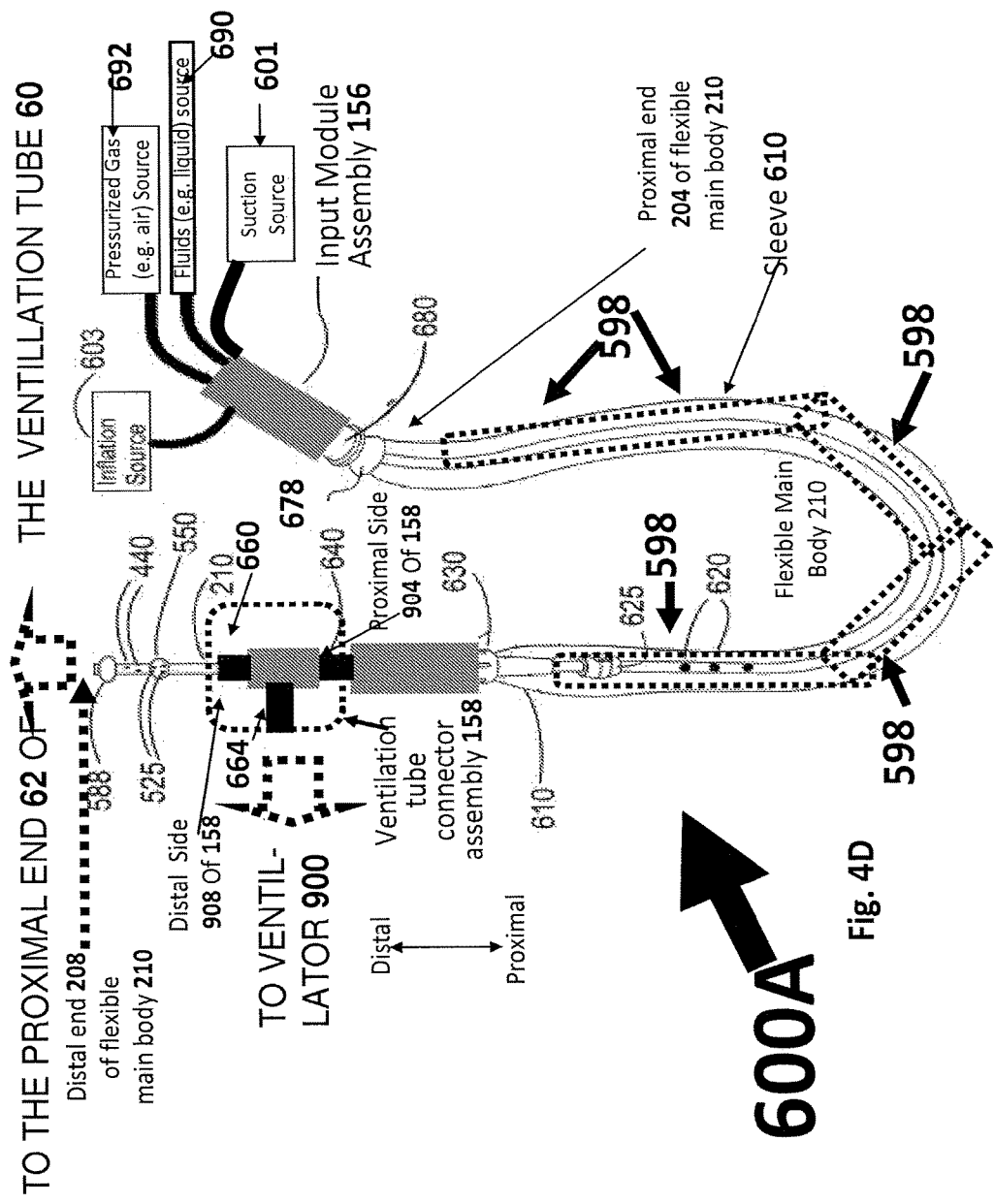
Figure 4E:
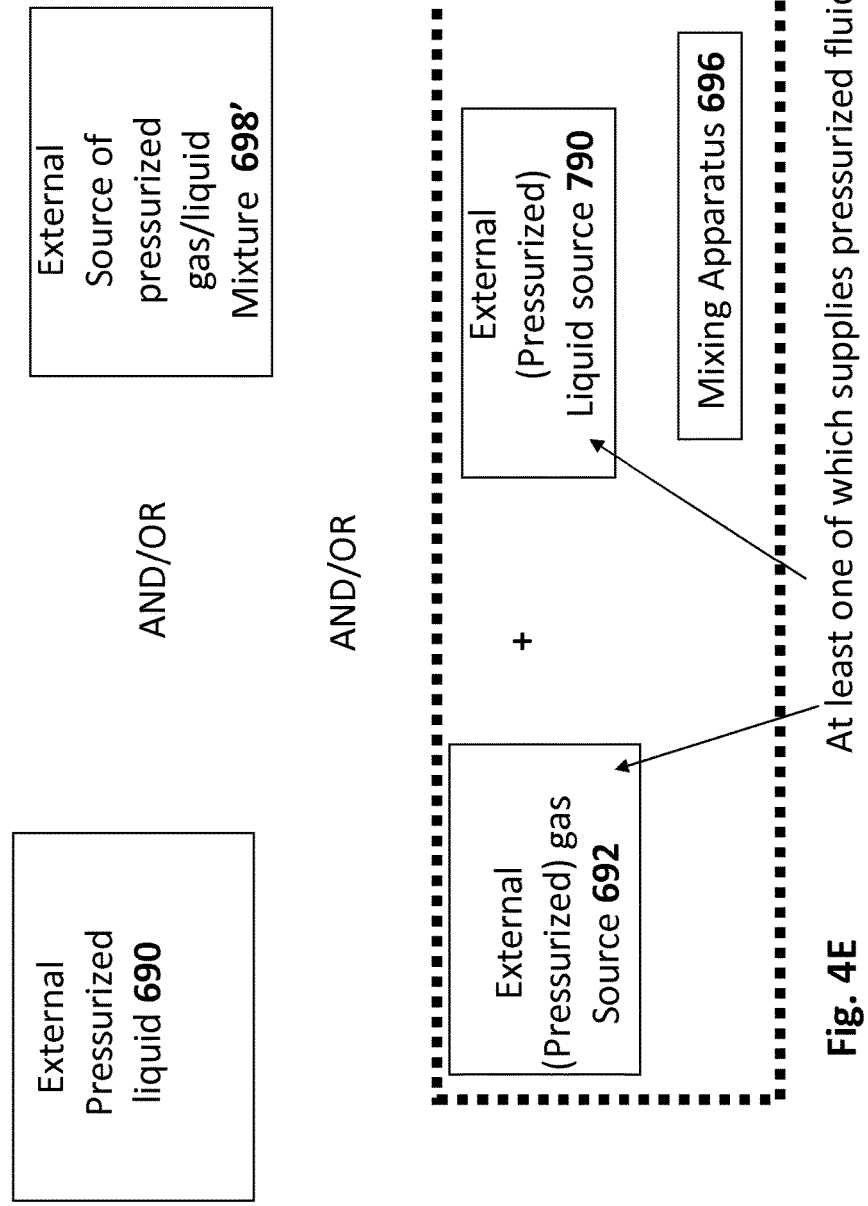

In the example of FIG. 4D, the cleaning device 600 receives: (i) gas (or gas-liquid mixture) (e.g. pressurized) from a first source 692 and (ii) liquid (or gas-liquid mixture) (e.g. pressurized) from a second source 602. These may be mixed—for example, within an 'inlets module' of device 600 or in any other location—for example, within a chamber or mixing apparatus 696 that is directly or indirectly connected/attached (e.g. permanently attached) to main body 610. This is illustrated schematically in FIG. 4E.

In some examples, this may obviate the need to provide a source of pressurized liquid. For example, it is possible to provide (i) a source of pressurized gas (or pressurized gas/liquid mixture) 692 and (ii) a source of liquids (i.e. pressurized or unpressurized) or liquid-gas mixture.

Figure 4F:
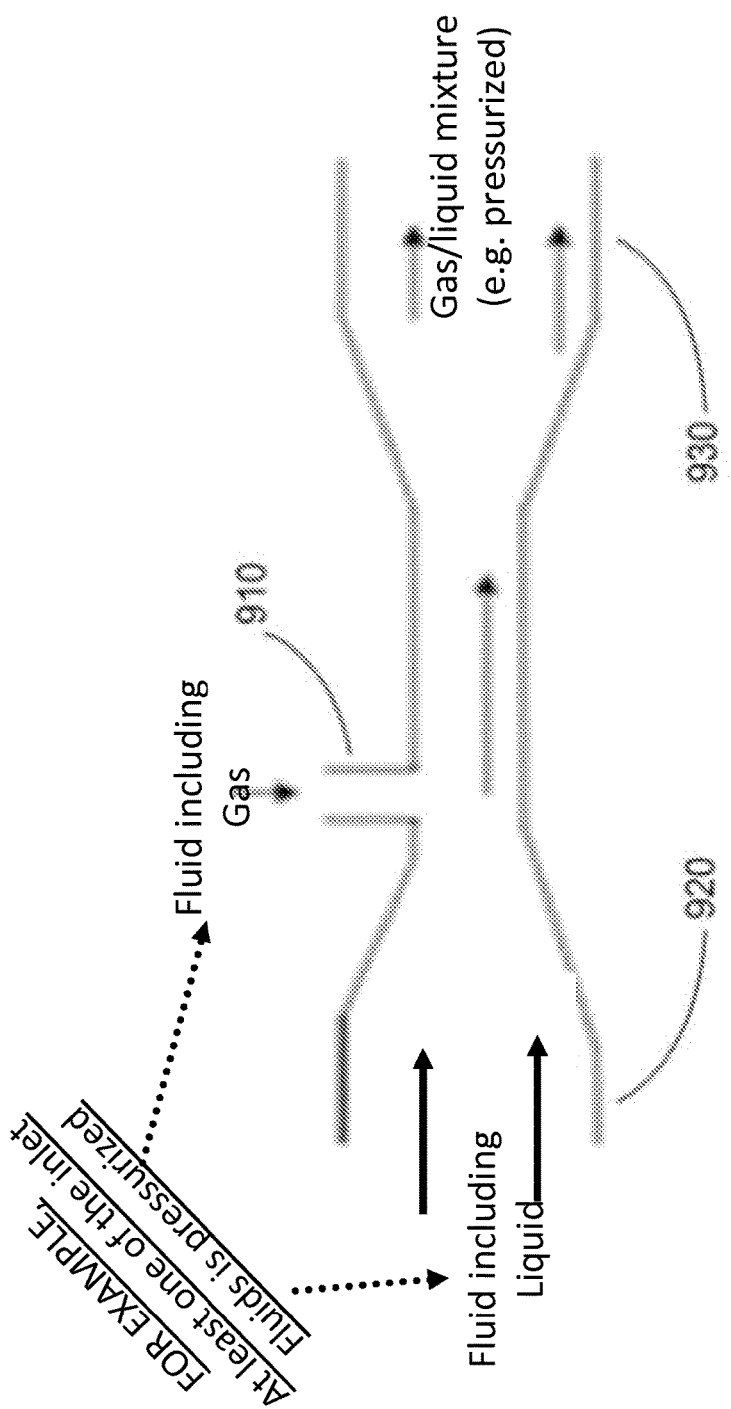

Liquids and gases may be mixed together within a mixing apparatus—for example, the apparatus 696 illustrated in FIG. 4F which operates for example according to the Venturi principle. The skilled artisan, after reading the present disclosure, will realize that there are a number of ways of mixing fluid and gases—for example, to produces a pressurized gas-liquid mixture including but not limited to techniques from the art of nebulizers (e.g. atomizers or jet nebulizers). Exemplary techniques include but are not limited to atomizing techniques or ultrasonic techniques or bubbling techniques any other technique for mixing gas and liquid—e.g. to produce a liquid-gas mixture for example pressurized.

Figure 5A:
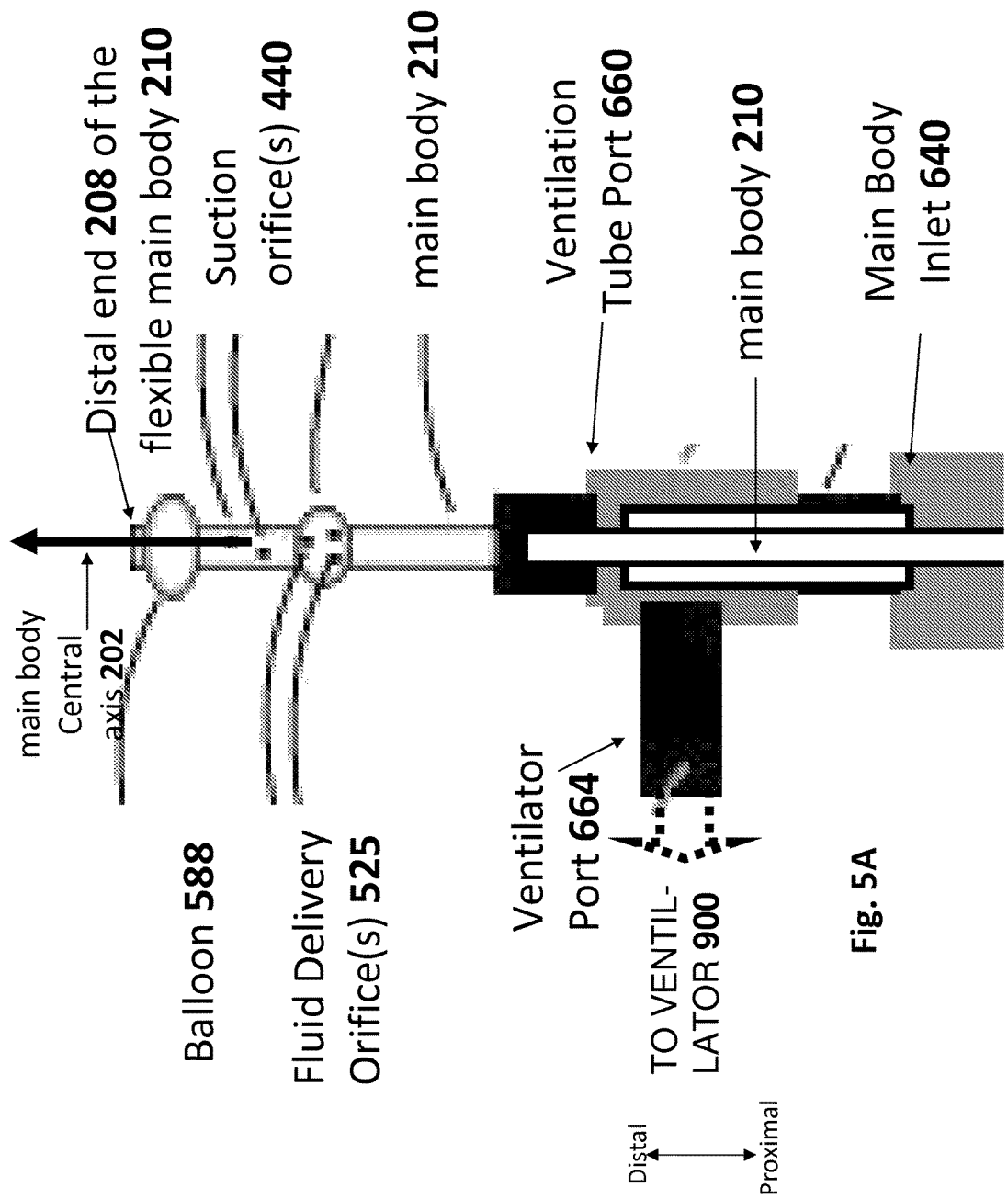
Figure 5B:
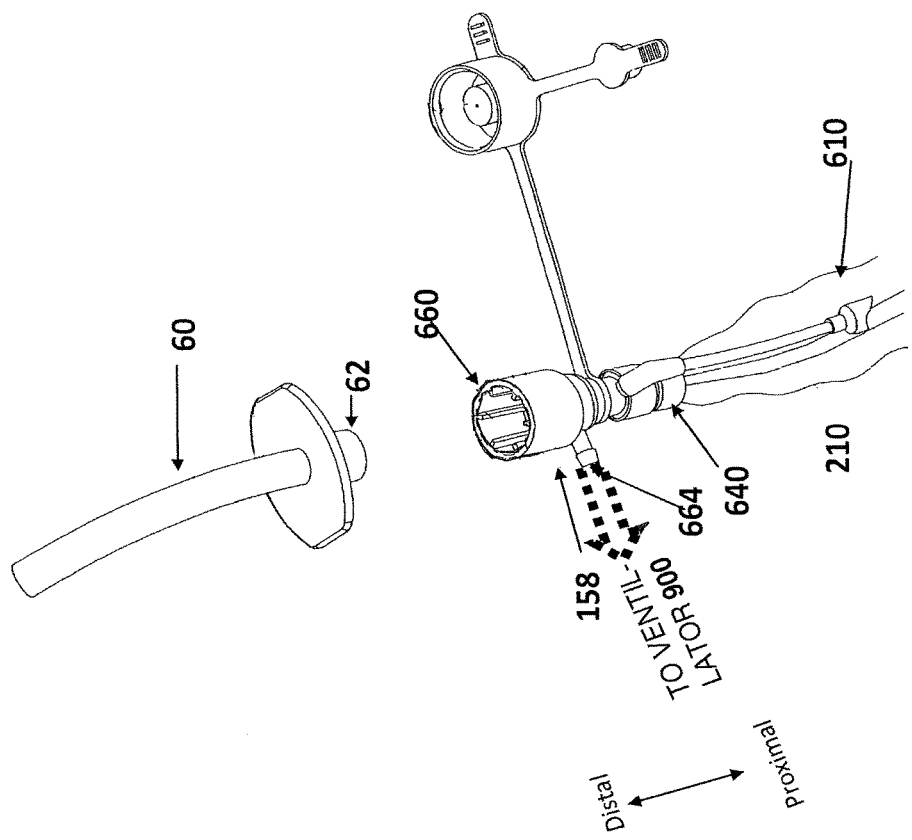

FIG. 5 is a close-up view of locations near distal end 208 of main body 210 in some embodiments and in some configurations. Inflatable balloon 588, suction orifice(s) 440 and fluid delivery orifice(s) are all visible close to the distal end 208 of main body 210.

FIG. 6 illustrates the distal end of main body 210 after insertion into ventilation tube 60 having an inner surface 201. In the example of FIG. 6A, inflatable balloon 588 divides the region of space within the ventilation tube 60 but outside of main body 210 into two regions:

(i) A first sub-region 774 that is proximal to slidable 'boundary' whose longitudinal location is identified in FIG. 6 by a dividing line 780 (it is appreciated that the dividing line 780 is only a mathematical construct). This first sub-region 774 is referred to as the 'more proximal portion of the interstitial region outside of the main body 210 and inside of ventilation tube 60;

(ii) A second sub-region 778 that is distal to dividing line 780.

Figure 6A:
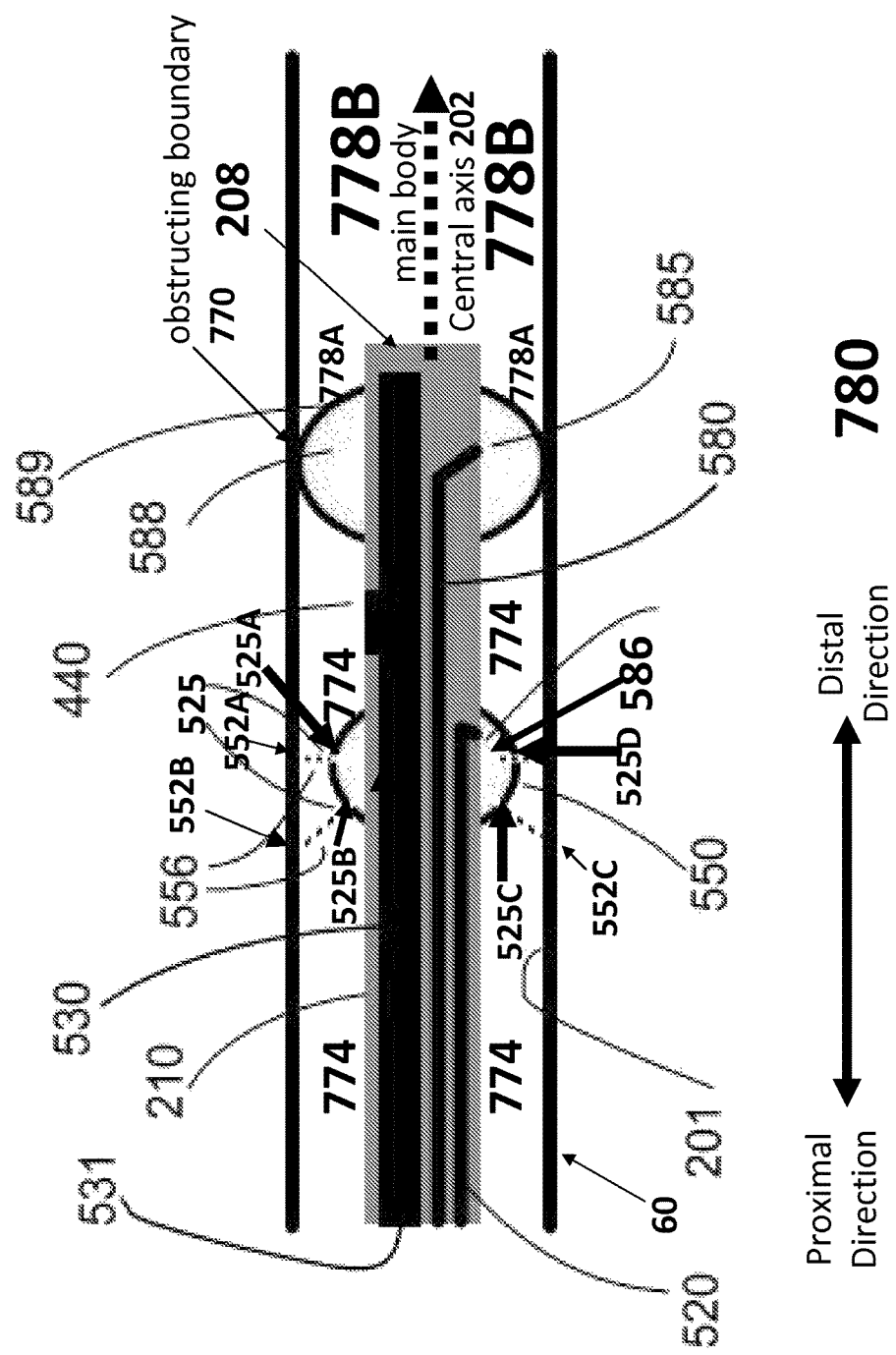
Figure 6B:
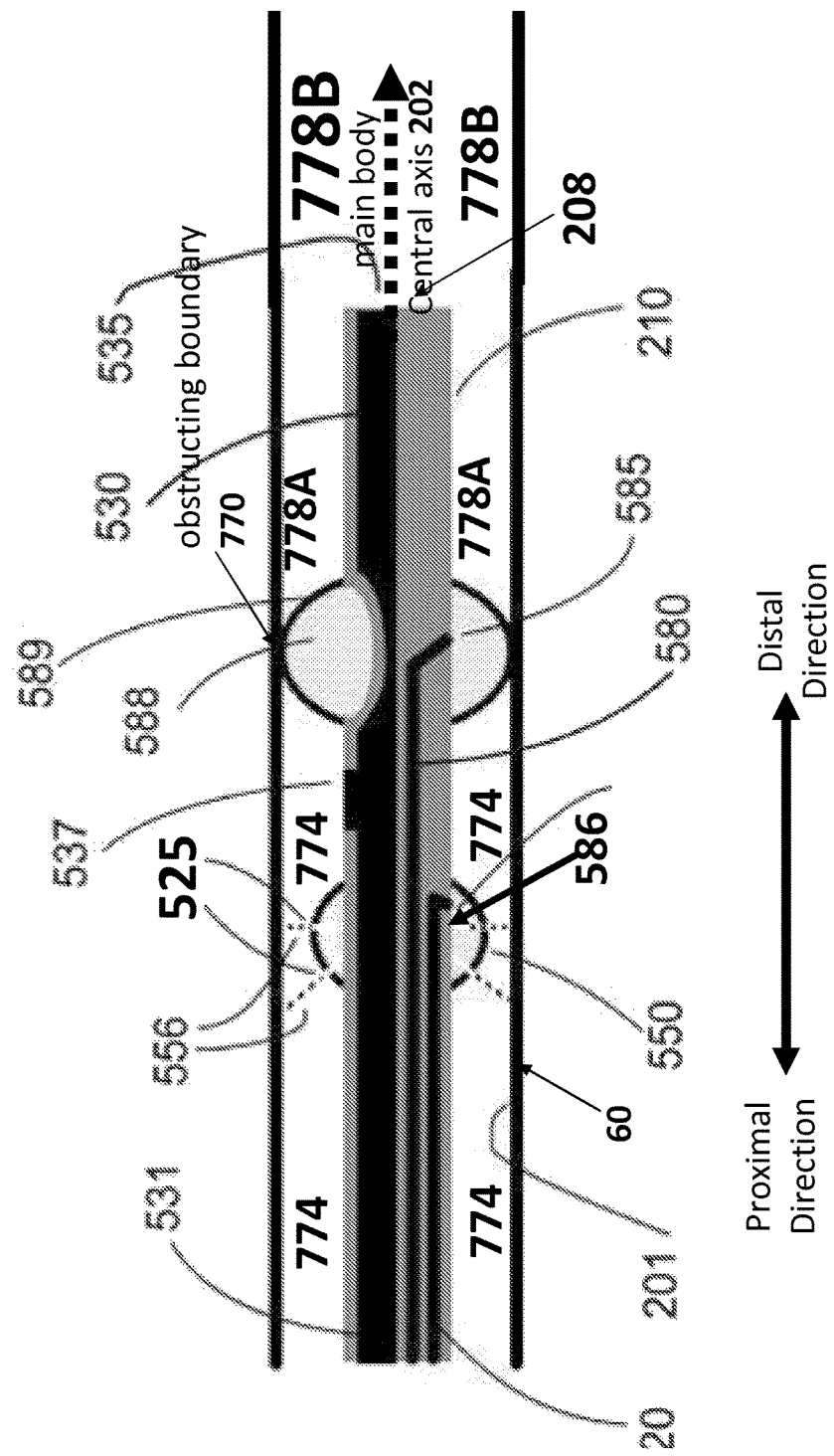
Figure 6C:
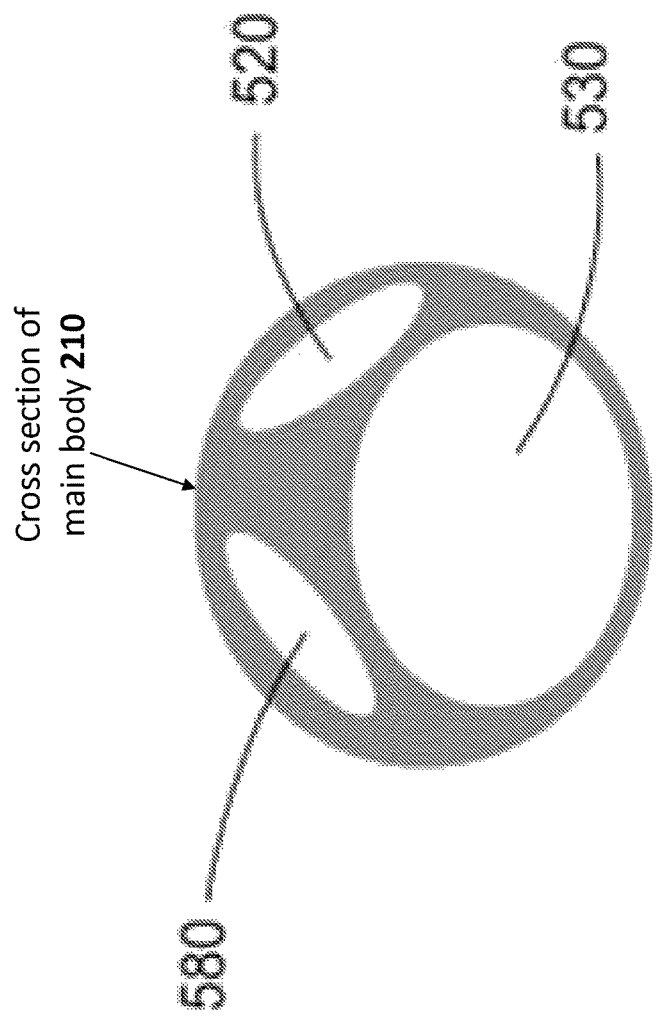
Figure 6D:
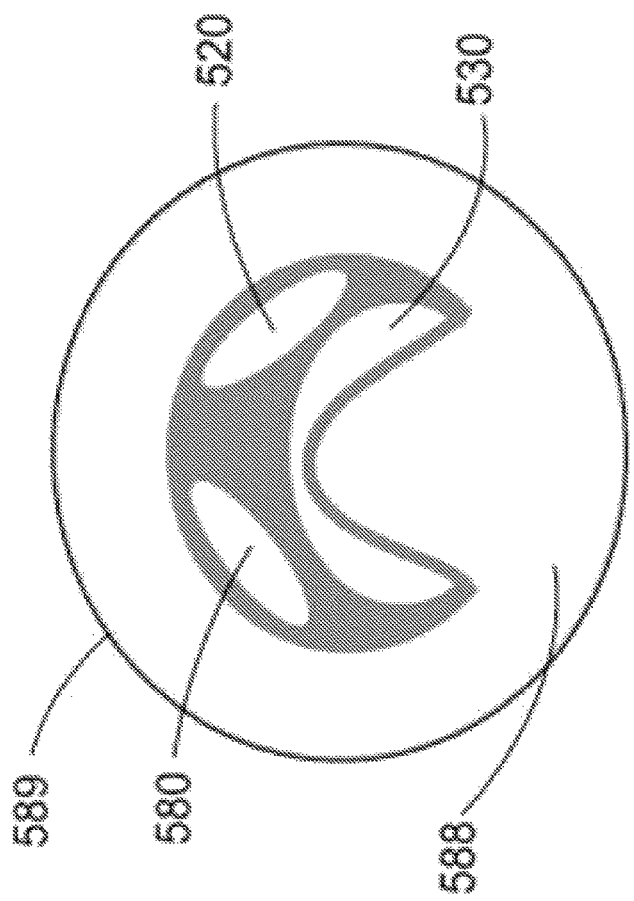
Figure 6E:
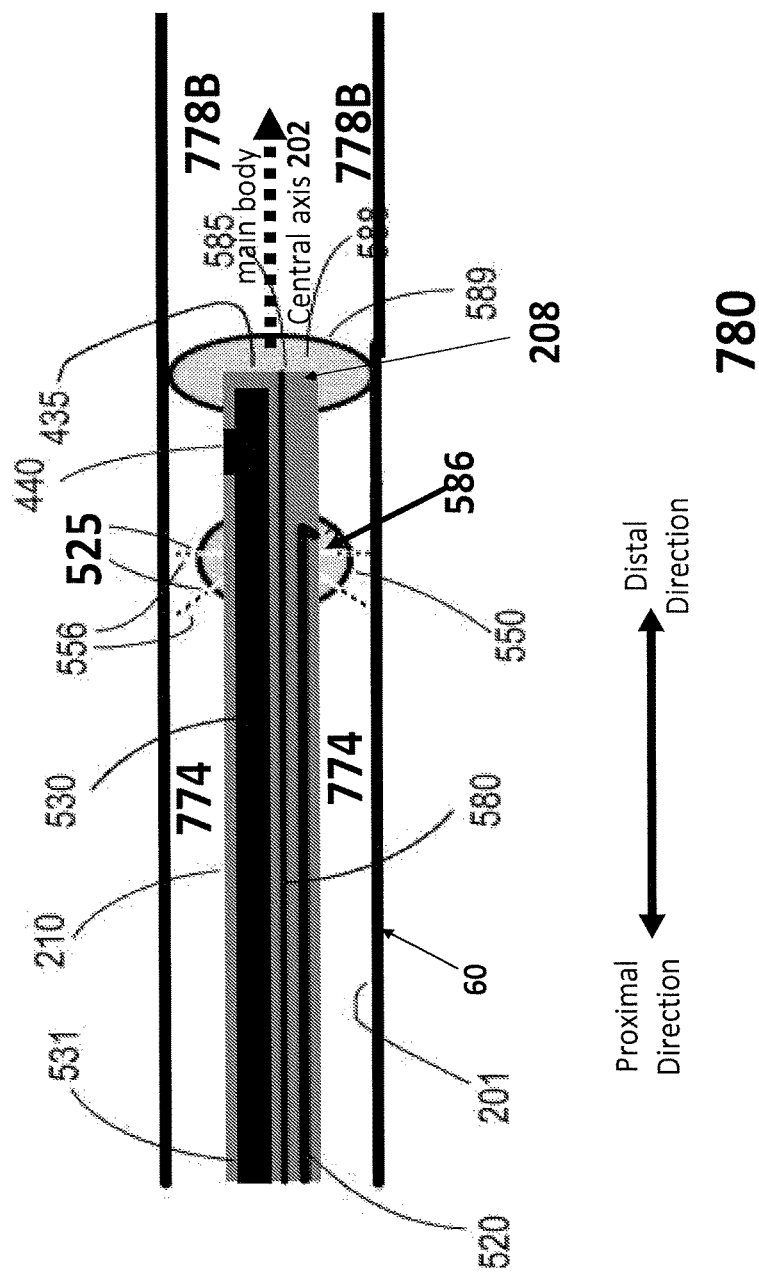
Figure 6F:
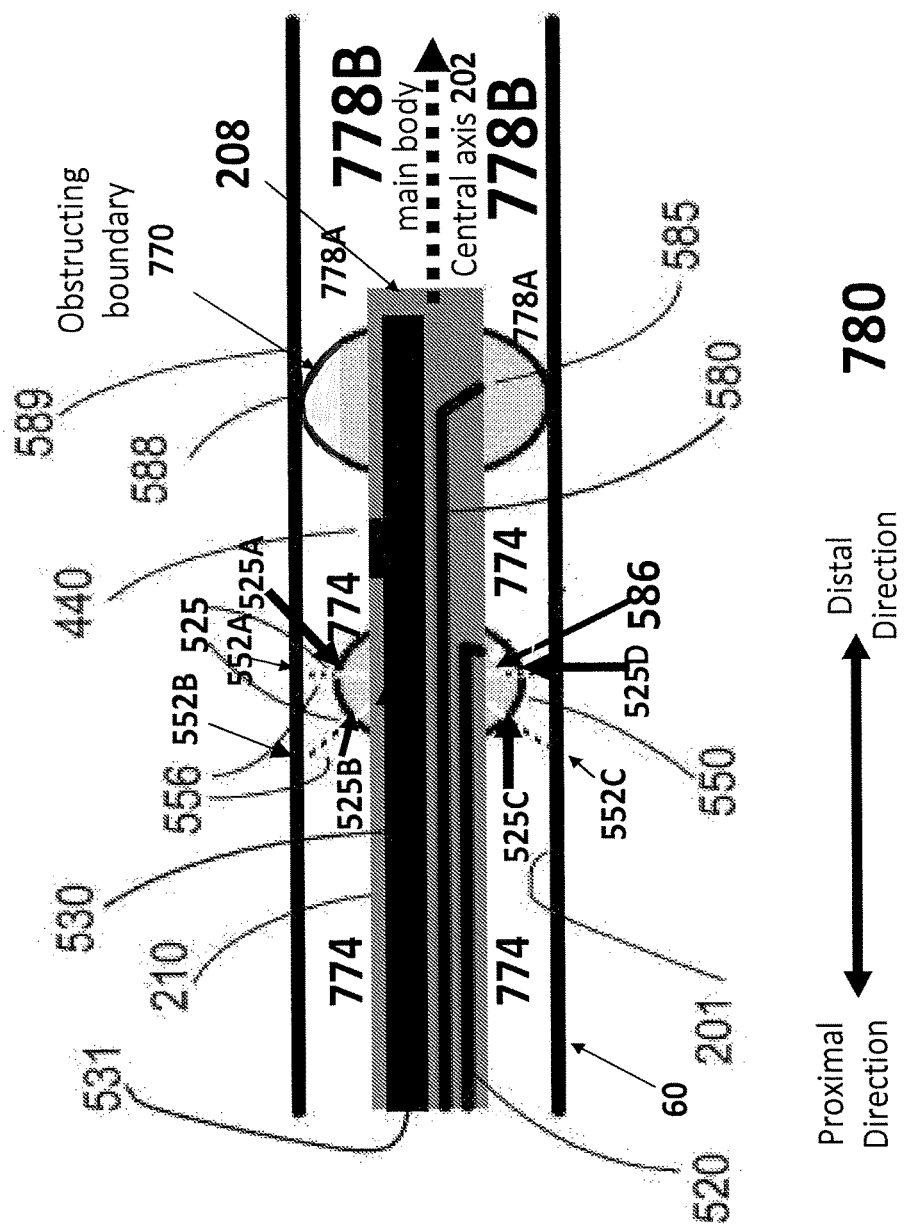
Figure 6G:
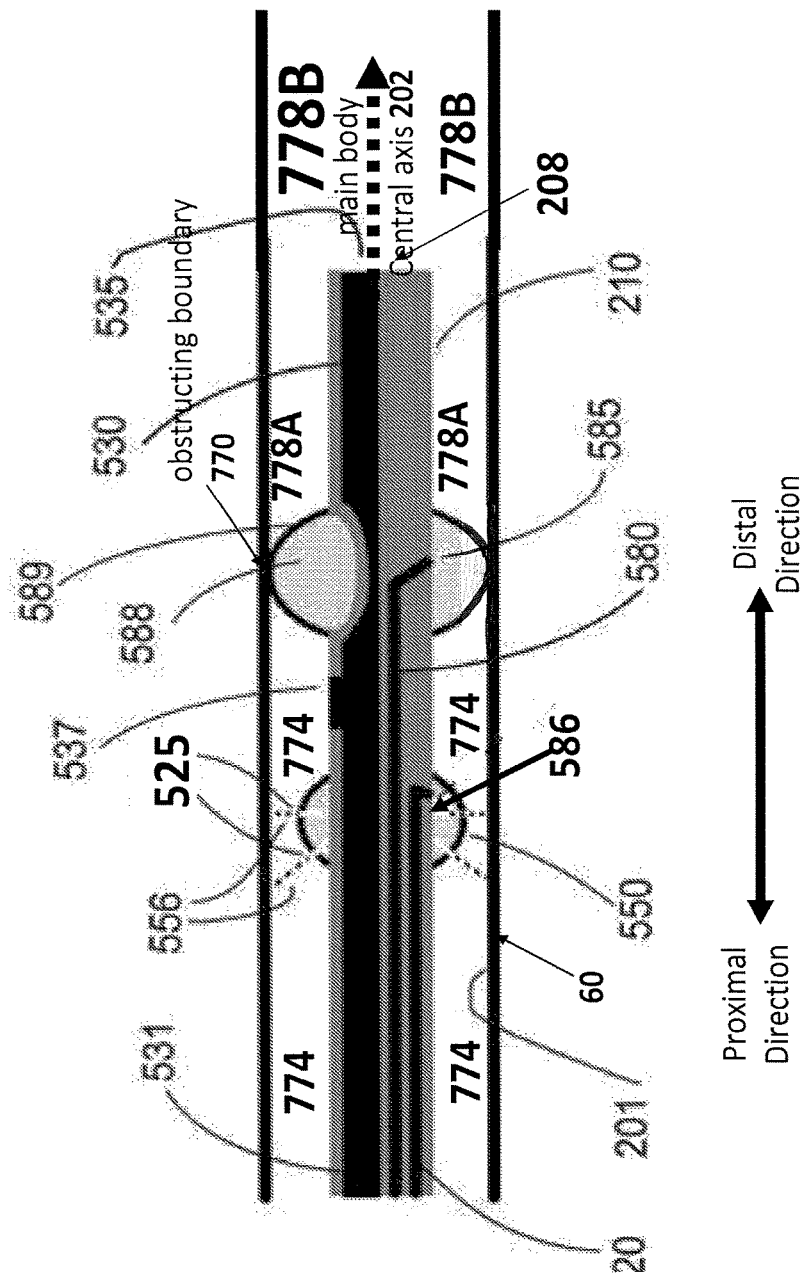
Figure 6H:
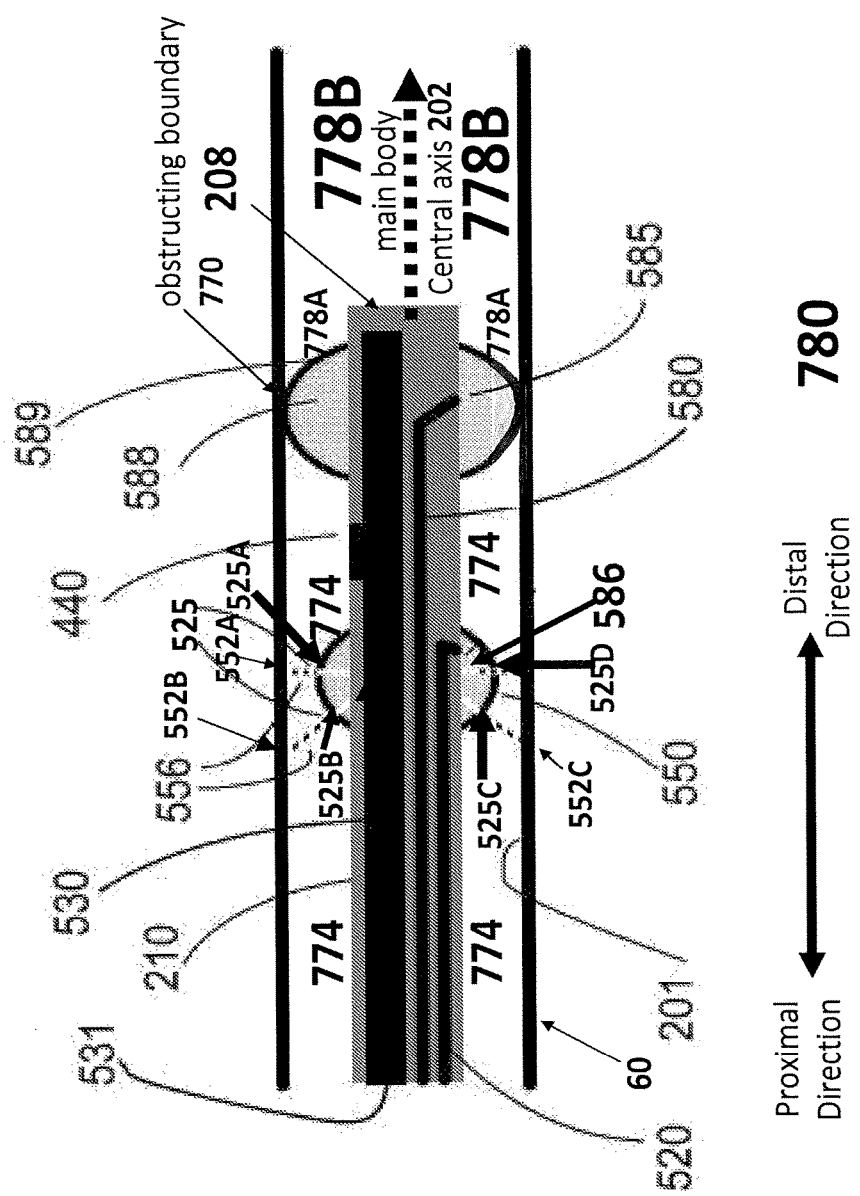
Figure 6I:
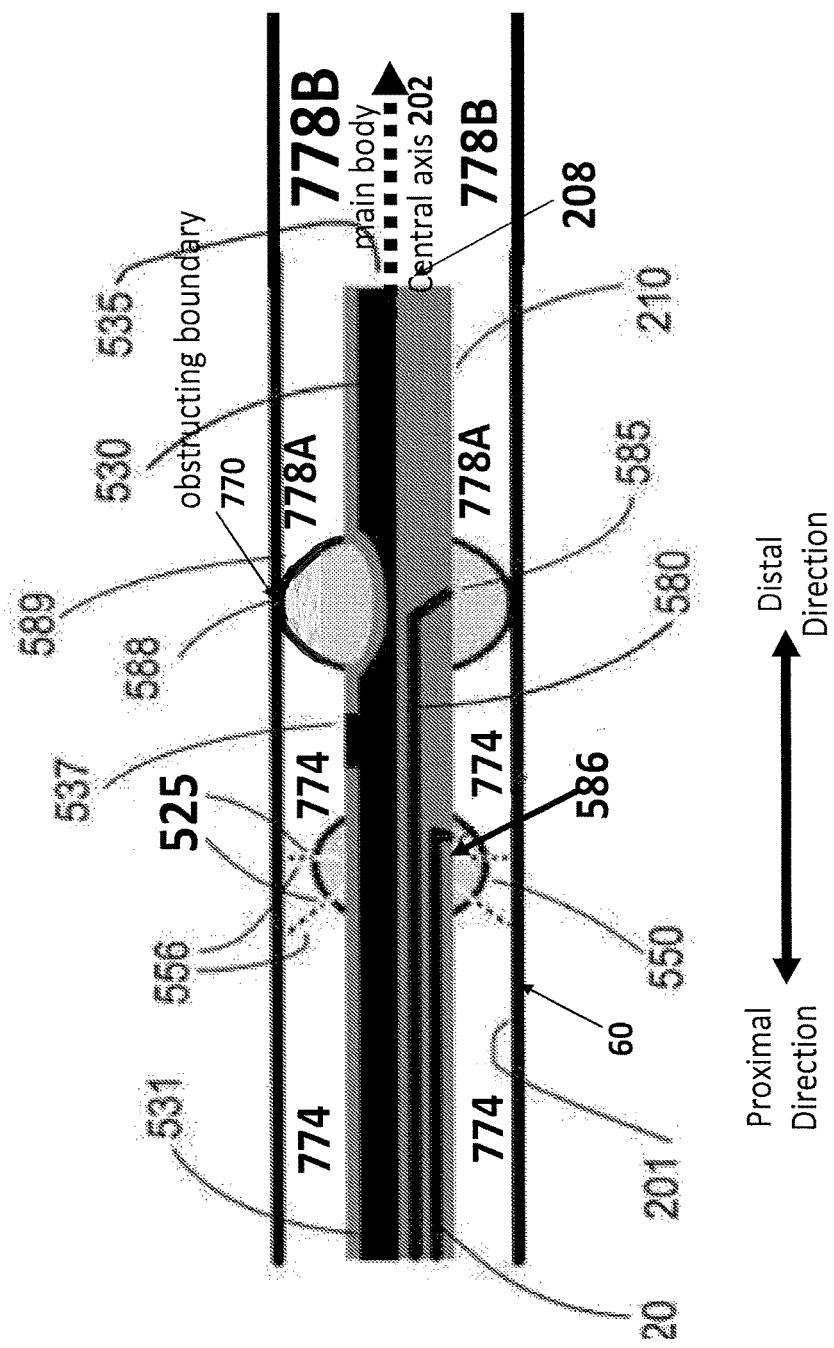

In the example of FIGS. 6A, 6E (also see FIG. 10A, 11A; 16A-16C) the balloon in contact with the inner surface 201 of ventilation tube 60 actually provides a seal between the first (i.e. proximal 774) and second (i.e. distal 778) regions. However, this is not a limitation, and in other embodiments (see, for example, FIGS. 6F-6I; 10C, 11C; 16D) it is possible for the inflated balloon to obstruct (i.e. significantly hinder) longitudinal flow between the first (i.e. proximal 774) and second (i.e. distal 778) regions without forming such a seal.

The first sub-region 774 may be referred to as 'the more proximal portion of the region within the ventilation tube and outside of main body' while the second sub-region 778 may be referred to as 'the more distal portion of the region within the ventilation tube and outside of main body.'

This second sub-region 778 may include: (i) locations in the interstitial region that are distal to the slidable boundary 770; and (ii) locations in the interior of the ventilation tube that are distal to the slidable boundary 770.

In the examples of FIGS. 6A, 6B, 10A, 14A, 14B,14C, contact balloon 588 (i.e. inflatable into contact) is deployed near the distal end 208 of main body 210 (but not at the distal end 208), and sub-region 778A is visible. In the examples of FIGS. 6E and 11A, inflatable balloon 588 is deployed at distal end 208 of main body 210 and sub-region 778A is absence. In both sets of examples, sub-region 778B is visible.

In the example of FIG. 6, a plurality of balloons located within ventilation tube 60 (i.e. each mounted to the main body 210—e.g. at or near a distal 208 end) include: (i) inflatable 'first' balloon 6 588 and (ii) second balloon 586 deployed to main body 210 (e.g. mounted to main body) which may or may not be inflatable and which functions as a 'liquid supply balloon.' The second balloon 586 includes one or more holes or voids which are fluid delivery orifice(s) 525 (in the example of FIG. 6A, four holes 525A-525D are illustrated). A pressurized liquid 525 may enter, via the fluid delivery orifice(s) 525 into 'the more proximal portion of the region within the ventilation tube and outside of main body' 774 of the interstitial region proximal to inflatable balloon 588 (for example, when balloon 588 is inflated into contact and/or so as to obstruct).

In some embodiments, the delivered fluid takes the form of a stream 556—for example, strong enough so that upon exit from the fluid delivery port 525 the flowing liquid has enough momentum to reach an interior surface 201 of ventilation tube 60. In some embodiments, the delivered fluid is pressurized immediately before exiting fluid delivery port 525 by at least 1.5 atmospheres or at least 2 atmospheres or at least 3 atmospheres.

In some embodiments, the delivered fluid is pressurized enough so that upon exiting fluid delivery port 525 a 'jet of fluid' or a 'strong jet' of fluid is obtained. In some embodiments, pressurized under a pressurize of at least 1.5 atmospheres or at least 2 atmospheres or at least 3 atmospheres exits a fluid delivery orifice having an internal width that is at most 1.5 mm or at most 1 mm or at most 0.75 mm or at most 0.5 mm.

Figure 7A:
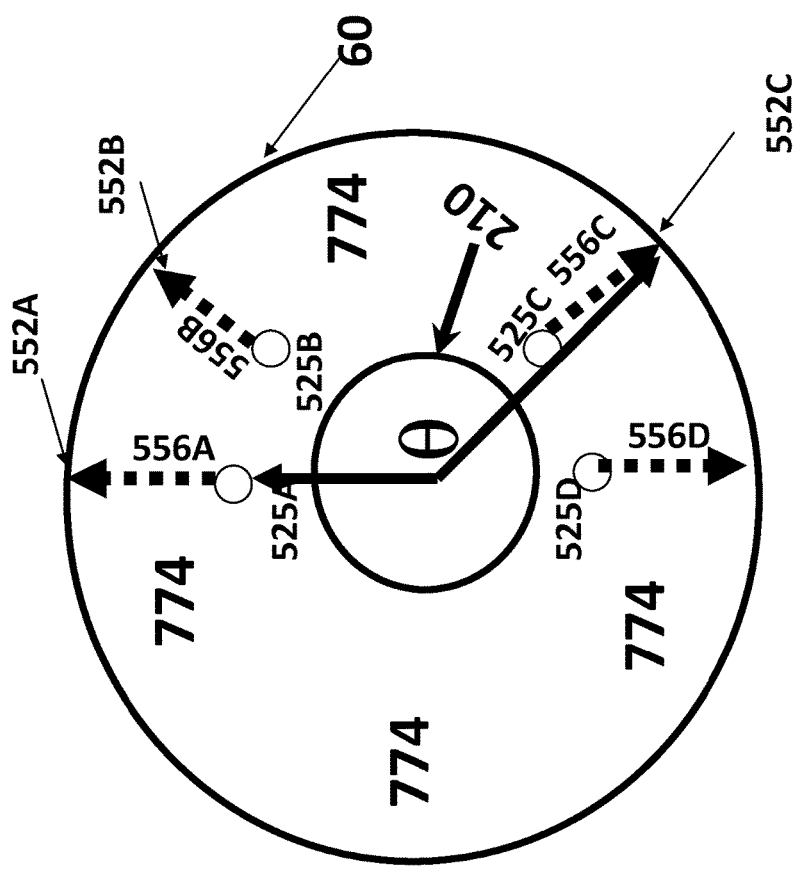

In some embodiments, the includes only a single fluid delivery orifice. Alternatively, in other embodiments, it is advantageous to employ a plurality of delivery ports. FIG. 7A illustrates four streams of liquid 556A-556D respectively exit from four different fluid delivery orifices 525A-525B.

In some embodiments, pressurized liquid (e.g. from a source outside of the ventilation tube and/or proximal to connector 158—e.g. from pressurized liquid source 602) is forced (e.g. simultaneously forced) through first 525A and second 525B fluid delivery orifices to respectively produce first 556A and second 556B fluid streams that are respectively incident (e.g. simultaneously incident) upon an inner surface 201 of the ventilation tube 60 at first 552A and second 552B locations. In some embodiments, the first 552A and second 552B locations are substantially on opposite sides of the ventilation tube 60 inner surface 201 within a tolerance that is at most 75 degrees (i.e. angle theta is between 105 and 180 degrees) or within a tolerance of at most 45 degrees (i.e. angle theta is between 135 and 180 degrees) or within a tolerance of at most 25 degrees (i.e. angle theta is between 155 and 180 degrees). Note that there is no requirement for first 552A and second 552B locations to have the same longitudinal position—i.e. it is possible to calculate theta by projecting the first and second positions into a plane that is perpendicular to a central axis of ventilation tube (e.g. having a longitudinal position that is the average of the longitudinal positions of the for first 552A and second 552B locations).

Although not a limitation, in some embodiments, one or more of the streams 556 may have enough momentum to reach an enclosing tube (e.g. ventilation tube 60). For example, any combination of the extent to which the delivered fluid pressurized and/or the size of the orifice (i.e. smaller sizes facilitated greater fluid momentum in stream 556) may be such that, for any position of main body 210 within tube 60, when the local central axis 202 (i.e. in the region of locations 552A and 552B) of main body 210 is perpendicular to the gravity vector, and when the local central axis (i.e. in the region of locations 552A and 552B) of an enclosing tube (e.g. ventilation tube 60) is parallel to gravity (e.g. both local axes are substantially straight), momentum of the delivered fluid upon exit via orifices 525A and 525B is sufficient such that respective streams 556A and 556B are incident upon locations in the inner wall For example, this may be true any position of main body 210 relative to an enclosing tube—e.g. a "reference" cylindrical tube having an inner diameter that is at least 4 mm or at least 6 mm and/or at most 12 mm or at most 10 mm or at most 8 mm. In some embodiments, under these conditions (e.g. both central axes parallel to the gravity vector so that the enclosing tube and main body 210 are at least locally 'upright', size features of the enclosing tube—e.g. ventilation tube 60) streams 556A and 556B may have enough momentum so as to be incident upon inner surface 201 of the enclosing tube at locations 552A, 552B that are substantially on opposite sides of the inner surface 201 of the enclosing tube 60.

Figure 7B:
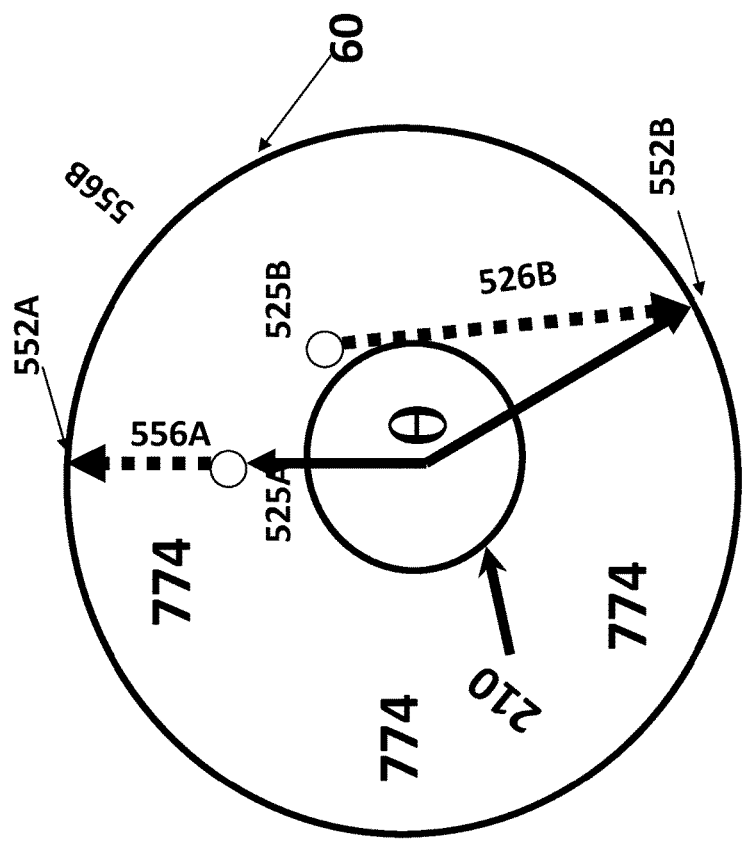
Figure 8:
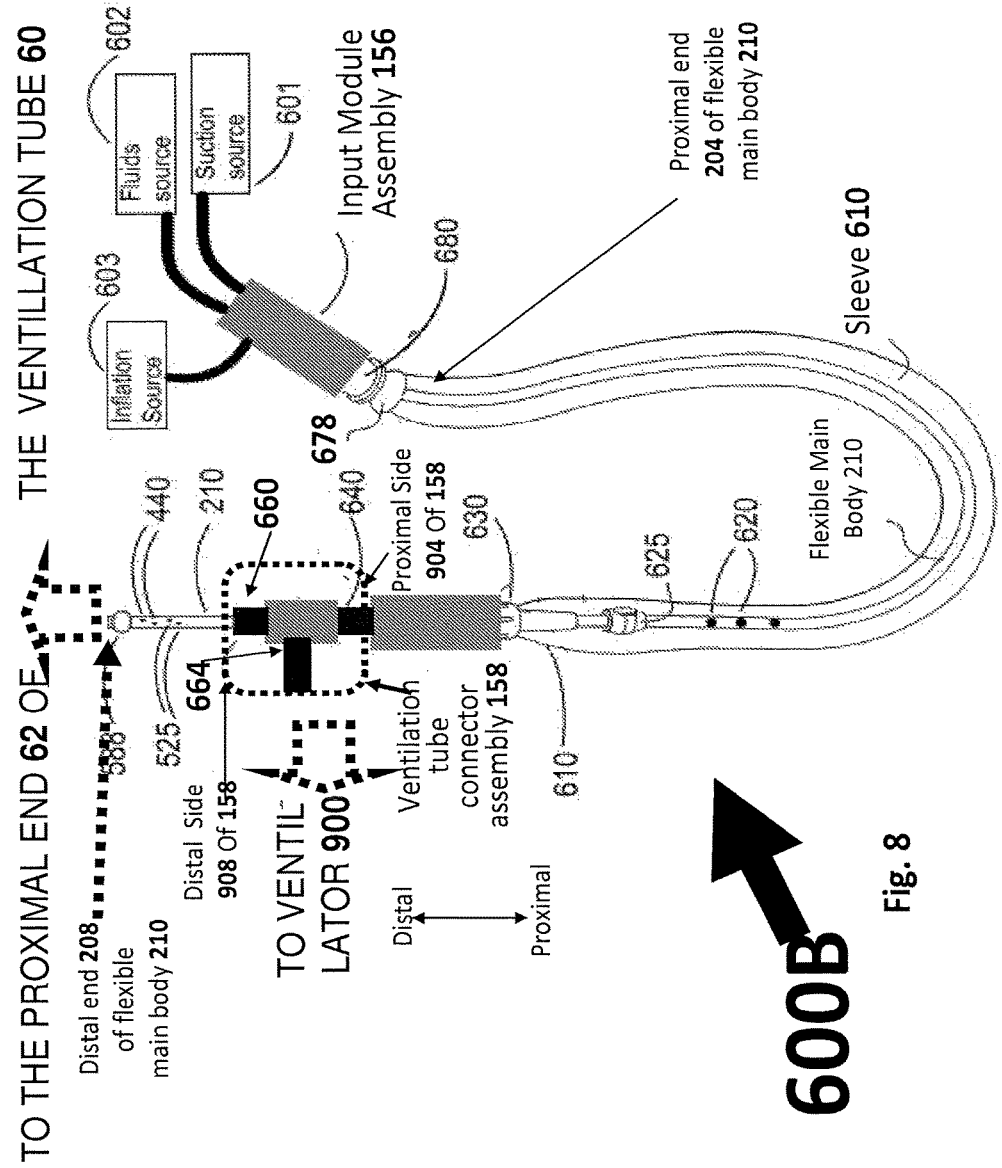
Figure 9:
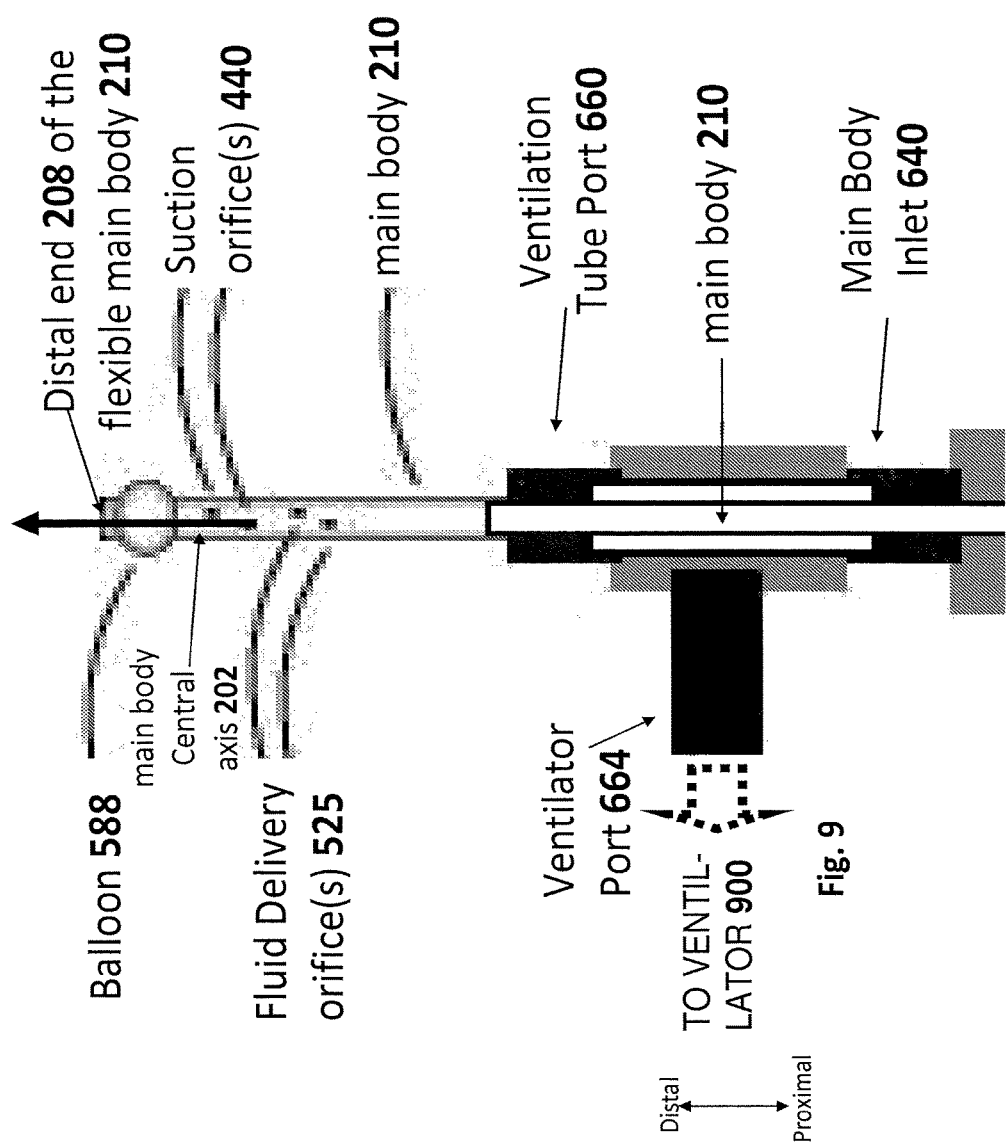

Any features described with relation to FIGS. 7A-7B are not limited to embodiments of FIG. 6, and may relate to the any other embodiment.

Not wishing to be bound by any particular theory, in some embodiments, delivering a stream of fluid with sufficient momentum to be incident upon inner surface 201 of ventilation tube 60 may be useful for mechanically dislodging biofilm temporarily attached to the ventilation tube inner surface 201 and/or chemically interacting with the biofilm in order to reduce any forces causing the biofilm to adhere to inner surface 201.

Not wishing to be bound by any particular theory, in some embodiments, ensuring that a plurality of streams are incident upon different 'sides' of ventilation tube inner surface 201 may be useful for achieving this effect throughout ventilation tube inner surface 201 (e.g. for longitudinal locations being cleaned—for example, located in a distal half of ventilation tube 60).

Reference is made once again to FIG. 6A. In FIG. 6A, suction orifice(s) 440 is also illustrated.

As illustrated in FIG. 6A, fluid delivery orifice(s) 525 is supplied with pressurized liquid (e.g. from liquid source 602) via fluid delivery lumen(s) 520. In some non-limiting embodiments, pressurized liquid received via fluid delivery lumen(s) 520 also functions to inflate second balloon 586. In some embodiments, second balloon 586 is inflatable. Alternatively, second balloon 586 is not required to be inflatable.

Suction orifice(s) 440 is supplied with negative pressure from suction source 601 via suction lumen(s) 530.

Inflatable balloon 588 is inflated with liquid or gas received from inflation source 603 via balloon inflation lumen 585.

In some embodiments, when inflatable balloon 588 is inserted into ventilation tube 60, balloon 588 is not sufficiently inflated to contact an inner surface 201 of tube 60 and thus free longitudinal motion of inflatable sealing balloon 588 is possible. After inflation, a slidable obstructing 'boundary' is created so that inflatable balloon 588 may longitindally move in ventilation tube 60 while in contact with the tube and/or inflated so as to 'obstruct' (i.e. significantly hinder) longitudinal flow. In some embodiments, inflation of balloon 588 is sufficient (e.g. for at least one location of main body 588 within main tube 210) to cause contact with an enclosing ventilation tube 60 and/or to 'obstruct flow' with the aforementioned 'reference' enclosing tube having an inner diameter of at least 4 mm or at least 6 mm and/or at most 12 mm or at most 11 mm or at most 10 mm or at most 8 mm.

FIG. 6C illustrates a cross section of main body 210 according to some embodiments. In some non-limiting example, lumen(s) may be embedded within main body 210 and provided as elongate voids within main body 210. In FIG. 6C, cross sections of three lumens are illustrated: (i) of suction lumen 530; and (ii) fluid delivery lumen 520 and (iii) of balloon lumen 580 via which pressurized gas or liquid is delivered from inflation source 603 into boundary-forming inflatable balloon 588. As noted earlier, there is no requirement for separate sources 602, 603 for fluid delivery into proximal region 744 and for balloon inflation. Similarly, there is no requirement separate lumen 520, 580.

FIGS. 8-11 illustrates an embodiment that lacks the second balloon 586. In the example of FIGS. 8-11, suction 440 orifice(s) and fluid delivery 525 orifice(s) are located on the surface of elongate main body 588. As was the case in the embodiments of FIGS. 4-6, (i) boundary-forming balloon 588 is inflated to form the slidable boundary between proximal 774 and distal 778 regions of the interior of tube

60, (ii) pressurized fluid (e.g. liquid or liquid-gas mixture such as a mist) enters proximal region 774 via fluid delivery 525 orifice(s), and (iii) material is suctioned into suction 440 orifice(s) for proximal transport out of ventilation tube 60. As noted elsewhere, fluid delivery and suctioning operations may be carried out sequentially or simultaneously. As noted elsewhere, in some embodiments, longitudinal motion of inflated boundary-forming balloon 588 (e.g. in a proximal direction) may be useful for wiping biofilm or other material attached to ventilation tube inner surface 201.

Figure 10A:
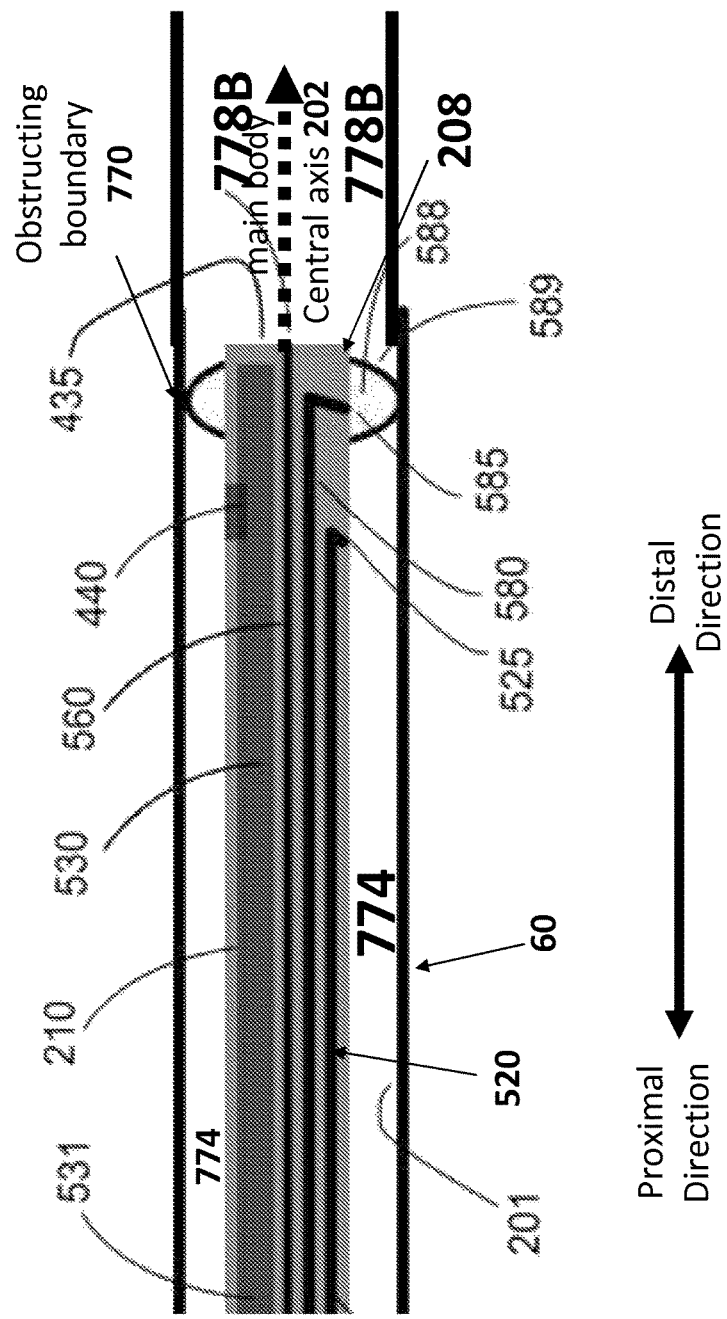
Figure 10B:
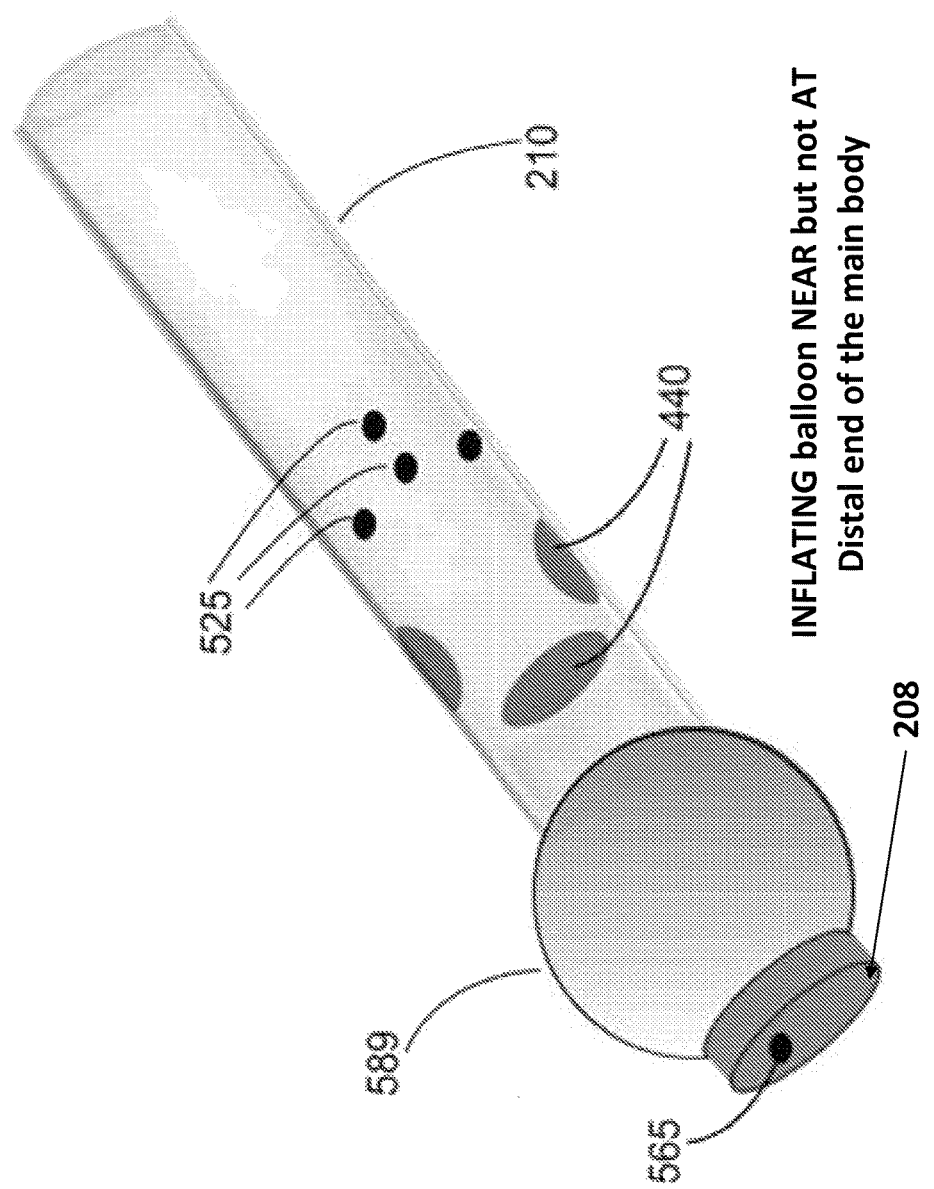
Figure 10C:
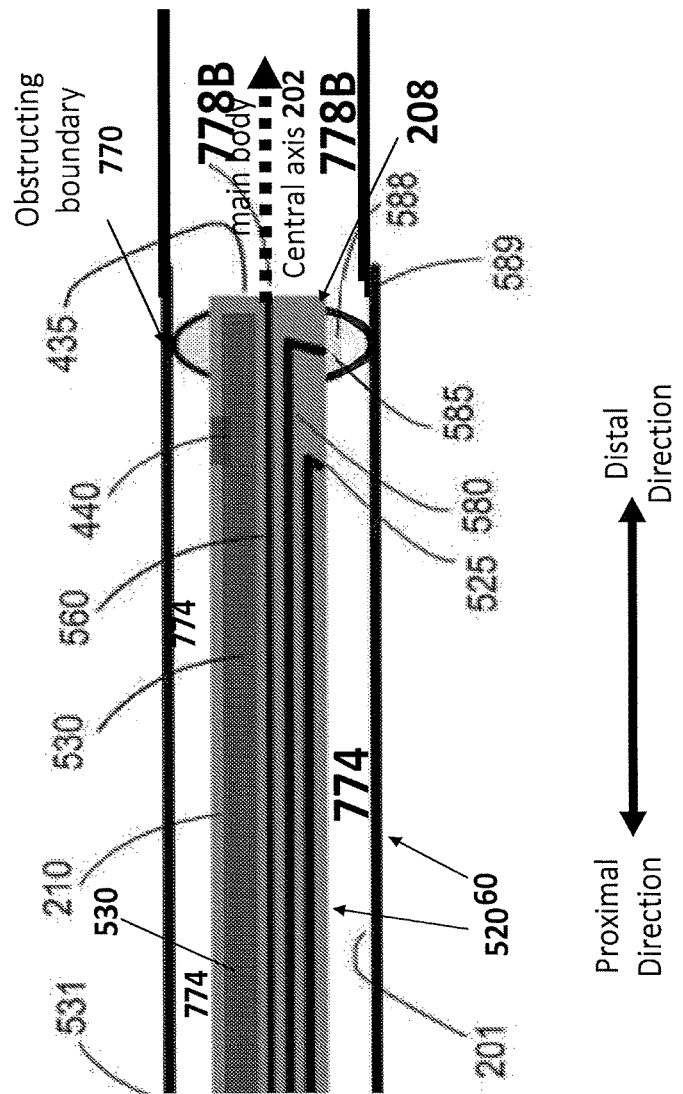
Figure 11A:
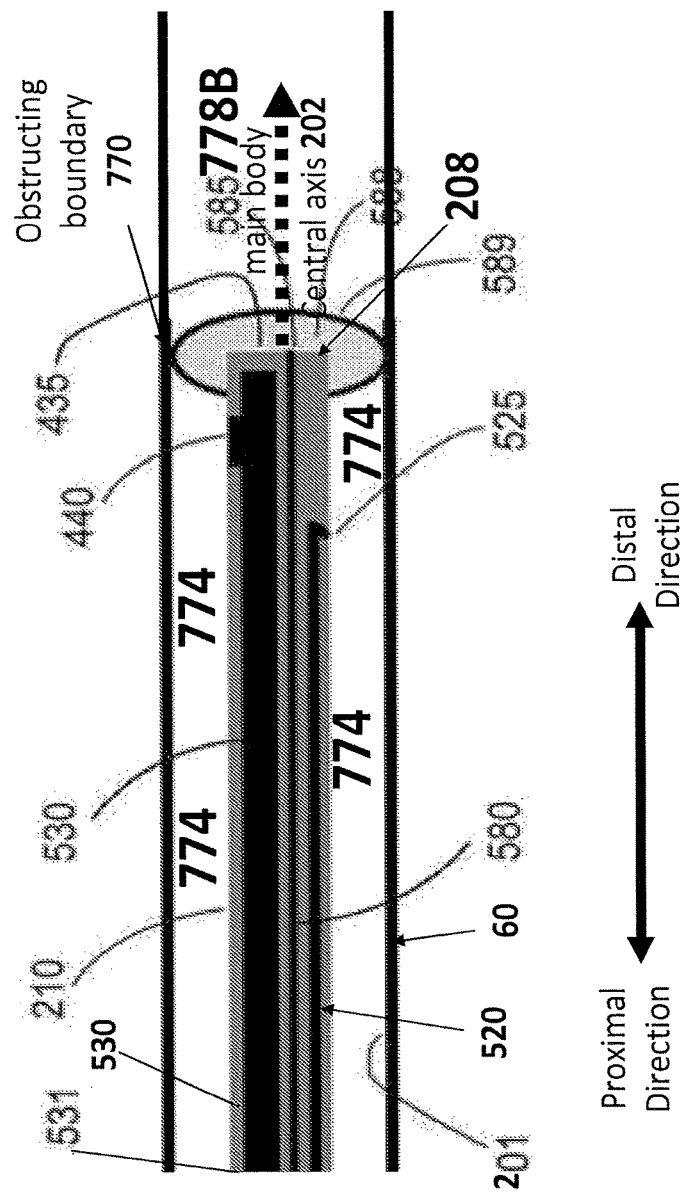
Figure 11C:
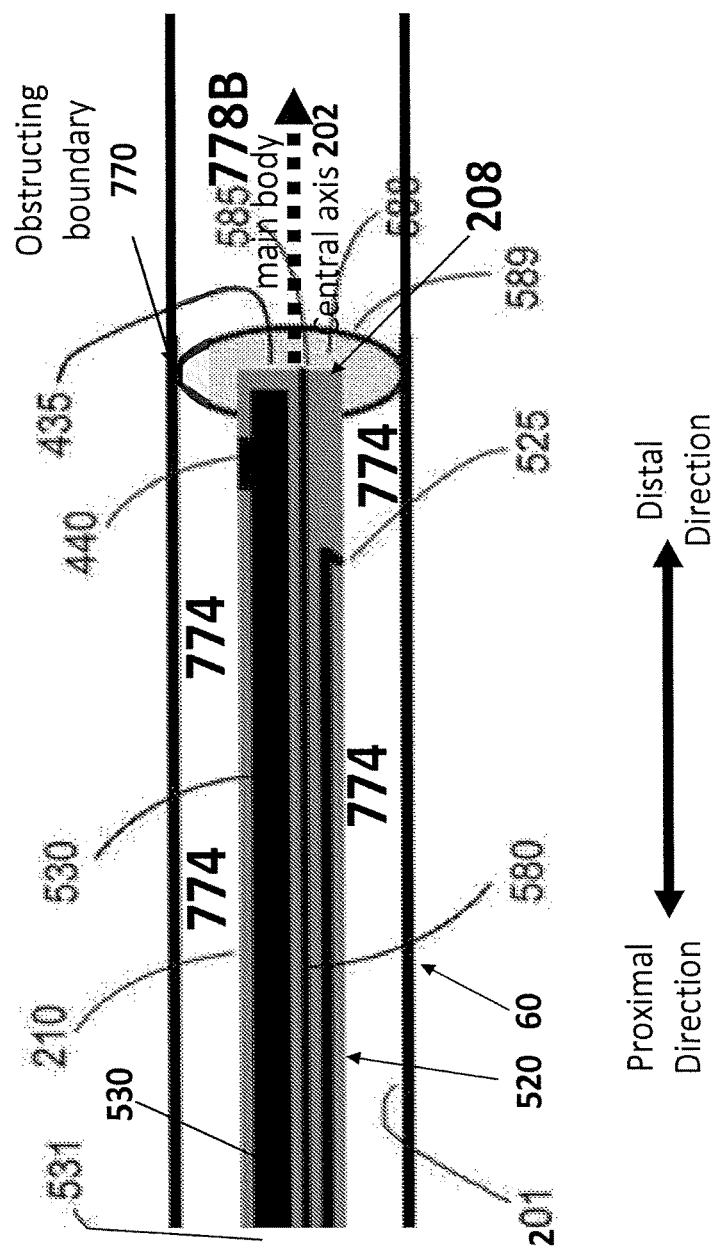

In the example of FIGS. 10A-10B, balloon 588 is not mounted at the distal end of main body 210. In the example of FIGS. 11A-11B, balloon 588 is mounted at the distal end of main body 210. In different embodiments, balloon 588 may be mounted to main body 210 at different locations, including locations not illustrated in the figures.

Figure 12:
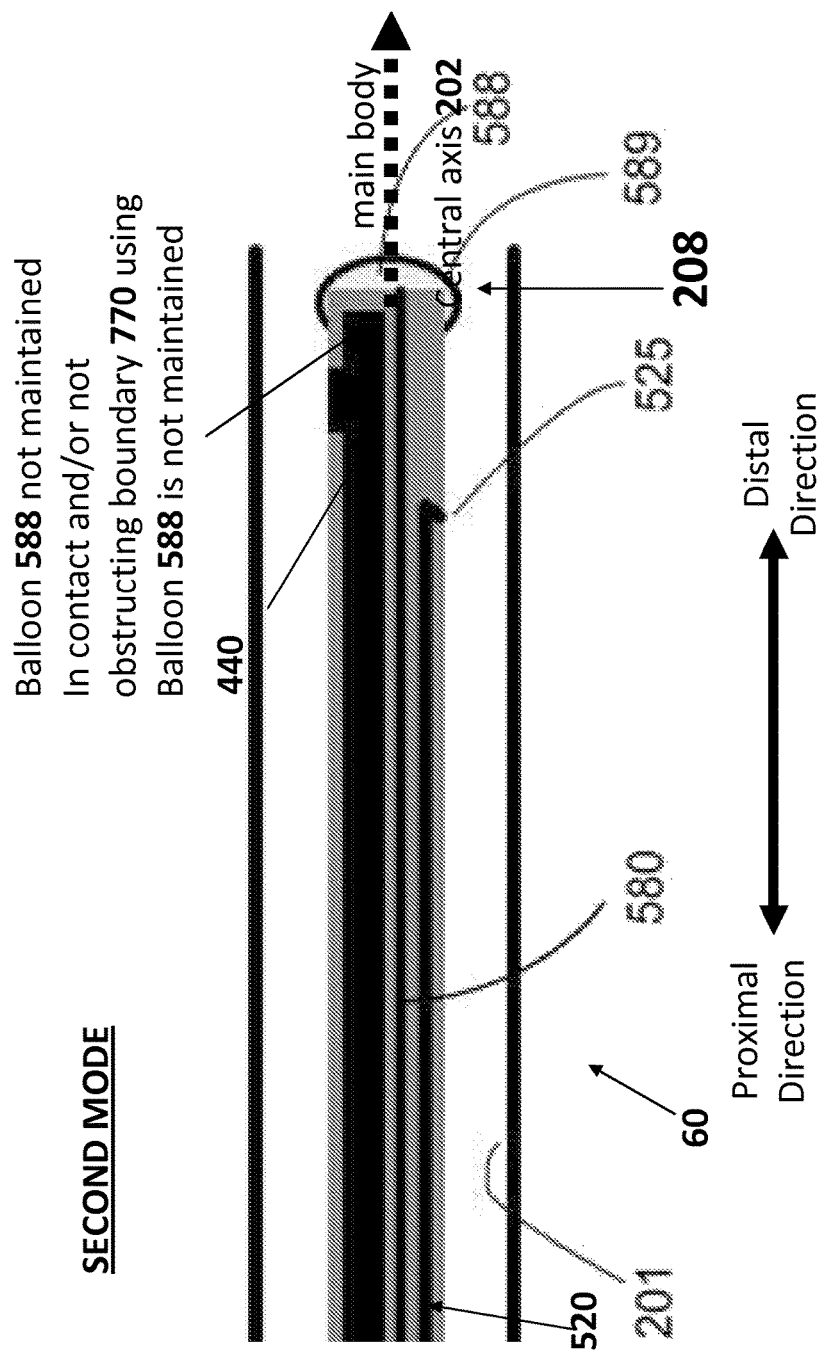

In the example of FIG. 12, boundary-forming balloon is not inflated and/or not sufficiently inflated to form a boundary that obstructs (i.e. significantly hinders) longitudinal flow between locations proximal and distal to balloon 588. This NON-CONTACT configuration may be useful for: (i) insertion of balloon 588 into tube 60 and/or distal motion of balloon 588 within tube 60 to a desired or target cleaning location; (ii) operation so that material located distal to balloon 588 (e.g. within the interior of tube 60 or distal to tube 60) may be suctioned into suction orifice(s) 440 and subsequently proximally transported out of tube 60 (e.g. within suction lumen(s) 530).

Thus, in some examples, it is possible to operate the cleaning device in multiple modes. In the first mode (see, e.g. FIGS. 6A-6B, 6E, 10A, 11A, 16A, 16B), (i) boundary-forming balloon 588 is in CONTACT mode so that 'obstructing' boundary (i.e. to significantly hinder longitudinal flow) is maintained; and (ii) material suctioned via proximally-located suction orifice(s) 440 (i.e. located proximal to boundary and/or balloon 588) is restricted, by the presence of boundary, to material within the proximal portion 774 of the interstitial region. This mode may used, in some embodiments, primarily to clean biofilm adhering to and/or temporarily attached to inner surface 201 of ventilation tube 60.

In the second mode (see FIG. 12), boundary forming balloon 588 is not sufficiently inflated to main boundary—however, proximally-located suction orifice(s) 440 are used to suction material distal of balloon 588 (for example, tracheo-bronchal fluids in the patient's trachea).

Figure 13:
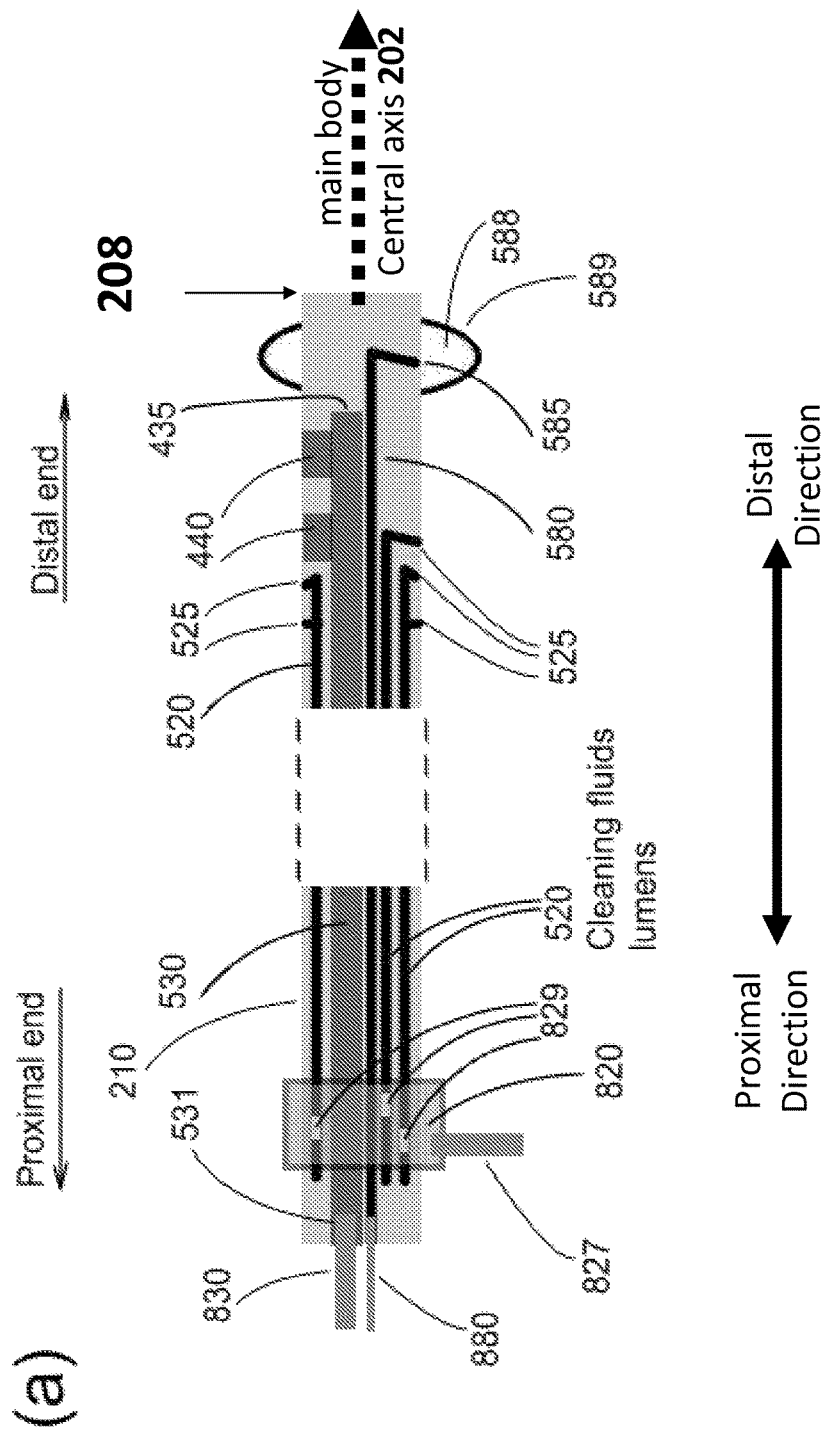

FIG. 13 illustrated proximal ends of various lumens. For example, it is possible to deliver pressurized fluid (e.g. from a source 602 of pressurized liquid or liquid-gas mixtures) through a proximal fluid port 827 into pressurized fluid reservoir 820. Pressurized liquid enters fluid delivery lumens 520 via respective openings in fluid delivery lumen located near the proximal end of the fluid delivery lumen 520.

In some embodiments, reservoir 820 may function as a mixing apparatus to mix gas and liquids—e.g. to provide pressurized liquid-gas mixtures).

As noted above, there is no requirement for multiple fluid delivery orifices 525, and some embodiments relate to the case where only a single fluid delivery orifice 525 is present. For embodiments where pressurized fluid (e.g. liquid or liquid-gas mixture) is distally sent to multiple fluid delivery orifices 525, it is possible to supply a multiple orifices by a single fluid delivery lumen 520 and/or to include multiple delivery lumen(s) 520. In FIG. 13, where the device includes five fluid delivery orifice 525, both features are illustrated. Multiple (e.g. two) fluid delivery lumen(s) are employed, and two of these lumens supply pressurized fluid (e.g. liquid or liquid-gas mixture) to multiple fluid delivery orifices 525.

Figure 14:
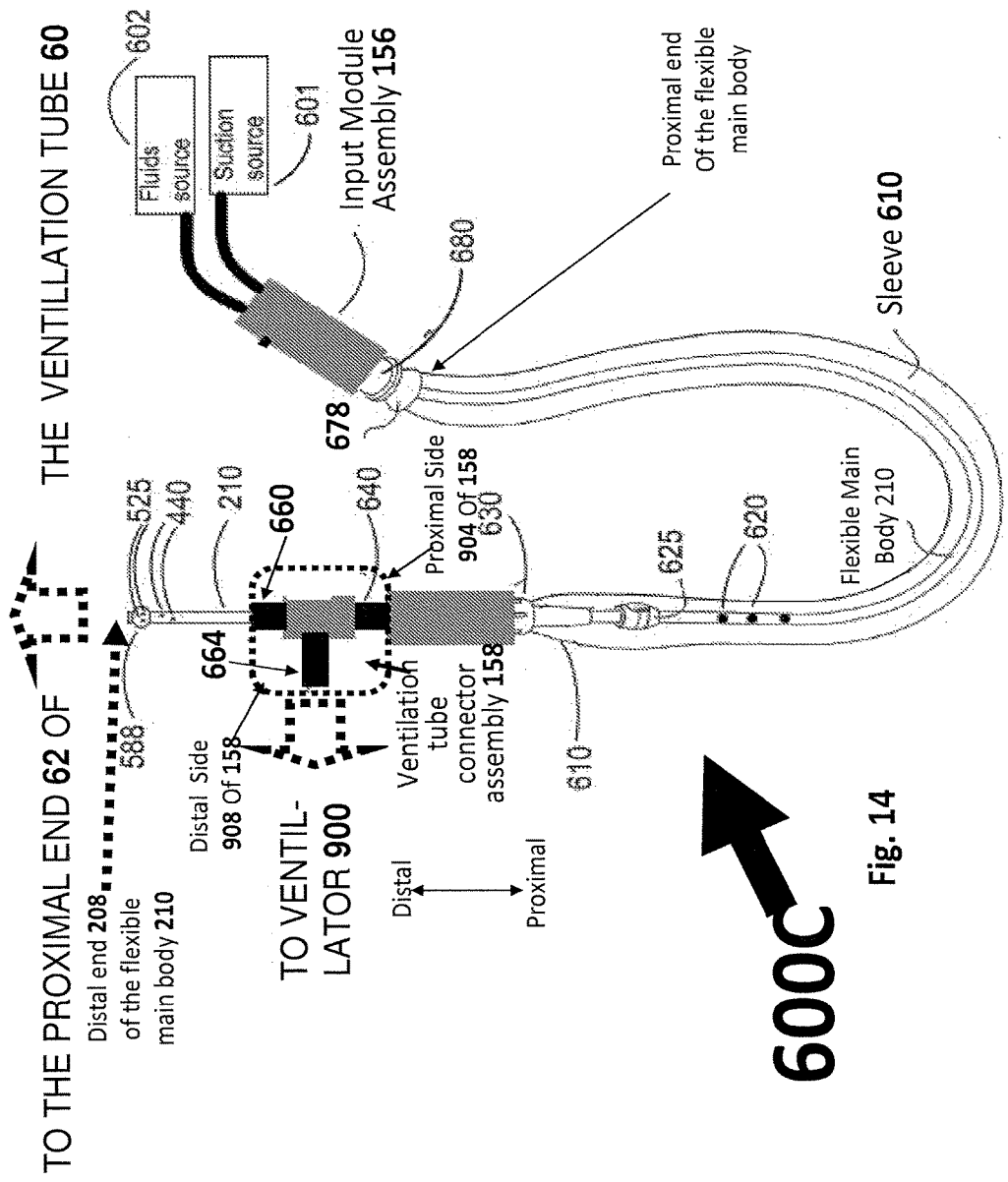

FIGS. 14-16 illustrate an embodiment of the invention where the fluid delivery orifices are actually located on surface 589 of boundary-forming balloon. In the non-limiting example of FIG. 4A, fluid delivery orifice(s) 525 located on the surface of the second balloon 550—for example, as voids or holes in the surface 589 of the balloon 588. In some embodiments, fluid delivered via these orifice(s) 525 is restricted to 'proximal' locations 774 within the interstitial region but proximal to boundary. As such, it may be useful to locate orifice(s) 525 on a proximal part of balloon and/or to orient orifice(s) 525 to deliver fluid in a proximal direction. In some embodiments (see FIG. 7) streams of fluid are incident upon substantially different sides of the inner surface 201 of tube 60—this feature is also provided in FIGS. 16A-16C.

Figure 16A:
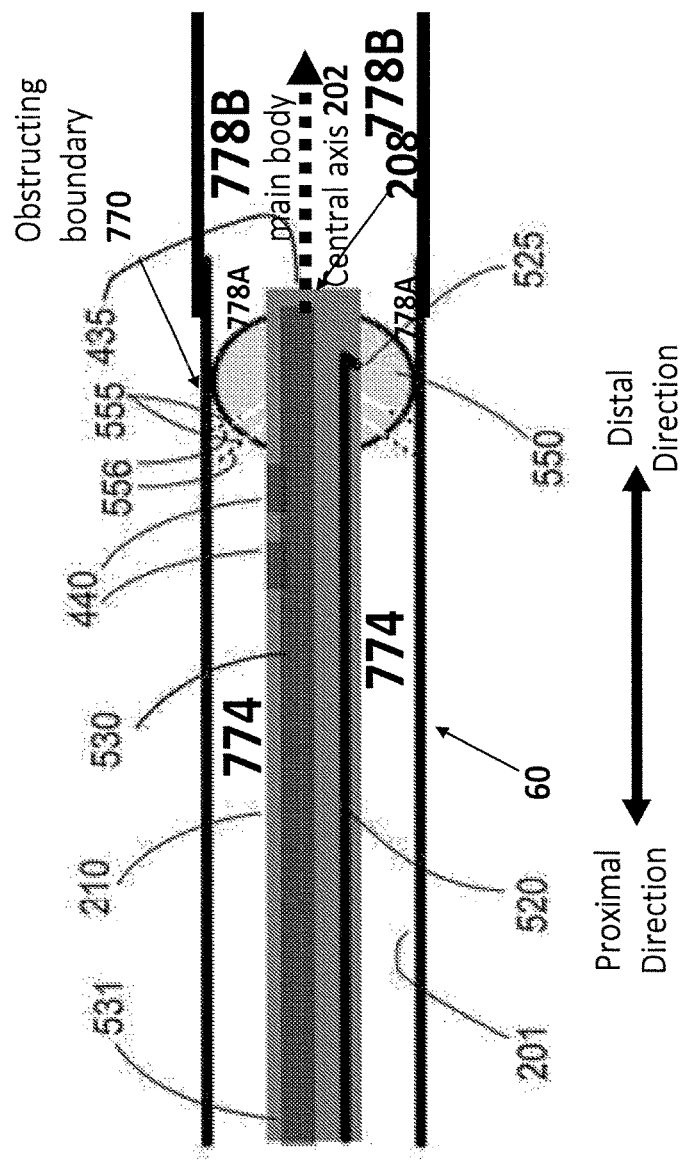
Figure 16B:
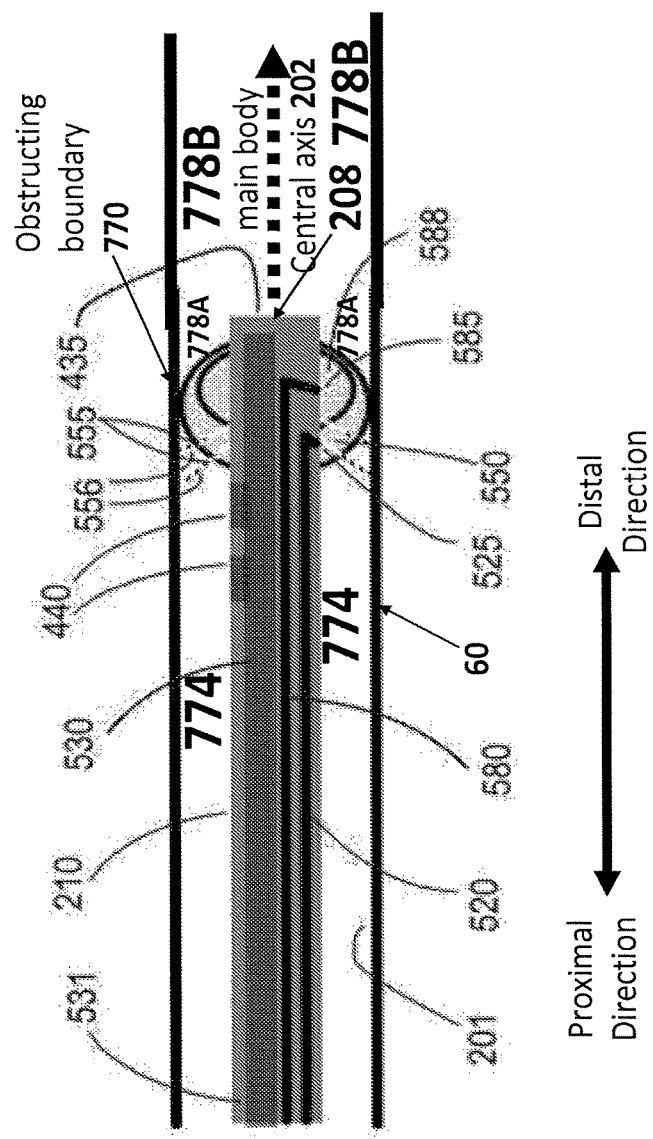

In the example of FIG. 16A, a single balloon is provided 588. Because this balloon includes one or more voids/holes on its surface 589 (i.e. these function as fluid-delivery orifices), pressurized fluid (i.e. liquid or liquid-gas mixtures—for example, a liquid-gas mixture that is predominantly liquid such as a bubbled liquid) needs to be supplied (e.g. from a source outside of tube 60 such as fluids source 602) at a sufficient rate (e.g. via lumen(s) 620) to maintain sufficient inflation of balloon 588 to maintain boundary. In some embodiments, the rate of pressurized fluid delivery to balloon 588 should, in the steady state, exceed that rate at which fluid is delivered from orifice(s) 525 in balloon surface 589 to maintain the contact between balloon 588 and inner surface 201 of tube 60.

In some embodiments, a ratio between an area of all orifice(s) 525 or voids in a surface 589 of boundary-forming balloon 588 to the total area of the surface 589 of boundary-forming balloon is at most 0.2 or at most 0.1 or at most 0.05 or at most 0.03 or at most 0.01 and/or at least 0.005 or at least 0.01 or at least 0.03 or at least 0.05.

Not wishing to be bound by theory, it is noted that in some clinical situations, a practitioner (e.g. nurse or doctor) needs to deflate and/or remove the balloon rather 'quickly'—e.g. within 60 seconds or 30 seconds or 15 seconds from a time that boundary is formed. This may be useful for reducing a risk of suffocation to the patient. Not wishing to be bound by theory, the provisioning of a single mechanism for both pressurized fluid delivery as well as maintenance of boundary can be useful for reducing the risk that, at the end of the procedure whereby an inner surface 201 of tube 60 is cleaned, the practitioner remembers to 'shut off' the fluid delivery but neglects to deflate boundary-forming balloon 588.

In some embodiments (see FIG. 14), it is no longer necessary to include separate pressurized fluid 602 and inflation 603 sources—it is sufficient to provide a single source for fluid delivery and for inflation.

In one variation (see FIG. 16B), it is possible to include a balloon within a balloon. For example, the inner balloon may be supplied with liquid or with a gas or a mixture thereof, and may have a separate fluids supply (and/or lumen(s)) than that of the outer balloon. In another variation (see FIG. 16C), a single balloon may include multiple compartments which are supplied by a common fluid supply and/or lumen or by separate supplies and/or lumens.

Figure 16C:
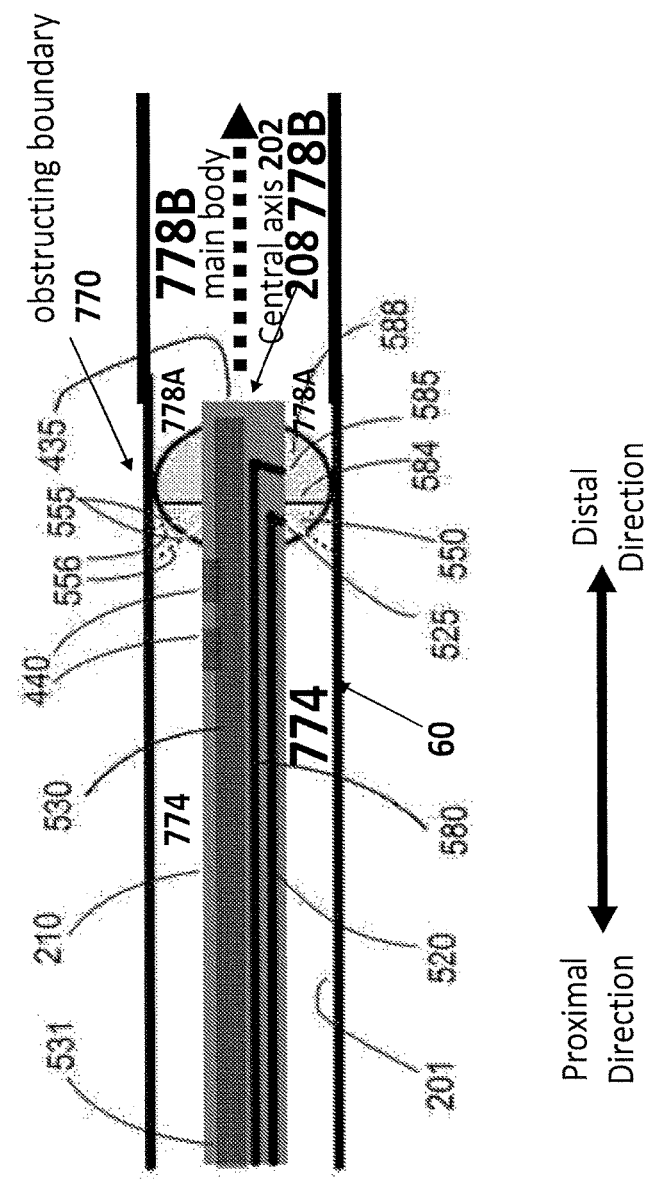
Figure 16D:
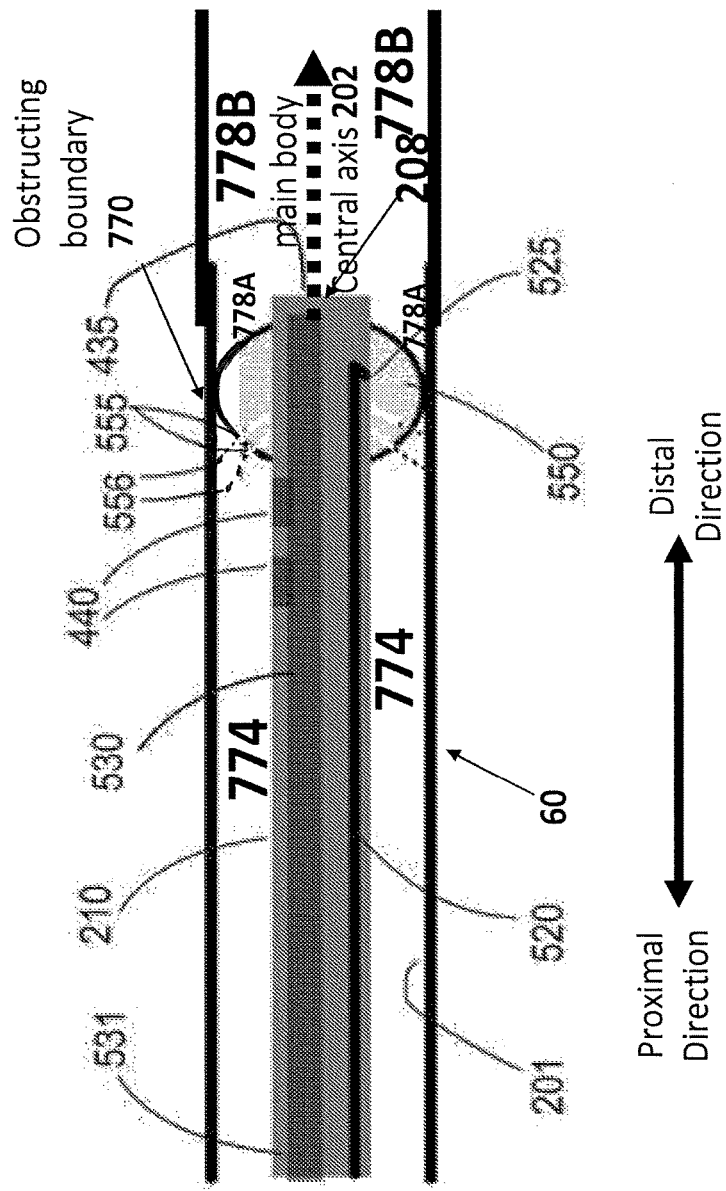

For the example of FIG. 16C, the proximal compartment includes fluid delivery orifice(s) 525, while the distal compartment lacks such orifices. The device may be operated in multiple modes. In one mode, distal compartment is sufficiently inflated (e.g. with gas or fluid) to form boundary. In this mode, delivery of fluid via fluid orifice(s) 525 in the proximal compartment is not needed to maintain the contact.

In a second mode, the distal compartment is not inflated or not sufficiently inflated to form boundary. In this mode, the device may provide features similar to those observed in the embodiment of FIG. 16A.

Figure 17A:
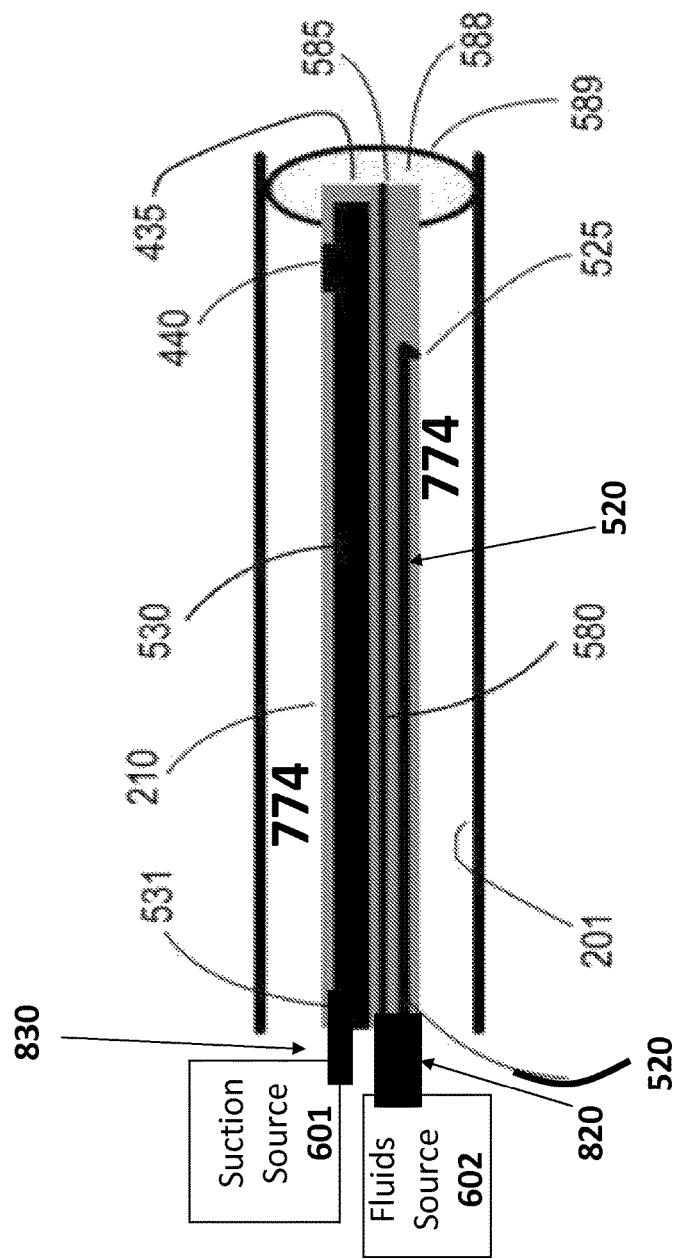

FIG. 17A illustrates yet another embodiment. In the example of FIG. 17A, a common fluids source 602 supplies fluid (e.g. liquid-containing fluid) to both balloon 588 and fluids delivery orifice 525. In some embodiments, common fluids source 602 is pressurized.

Figure 17B:
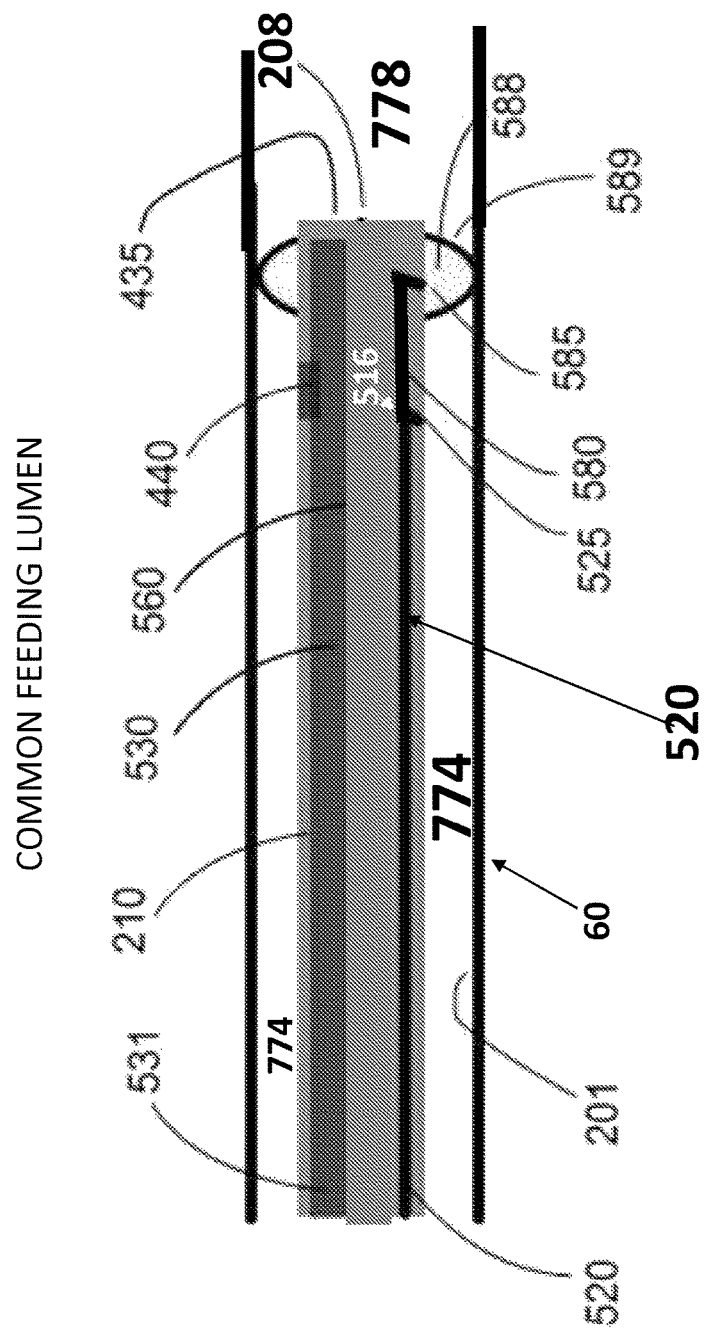
Figure 18:
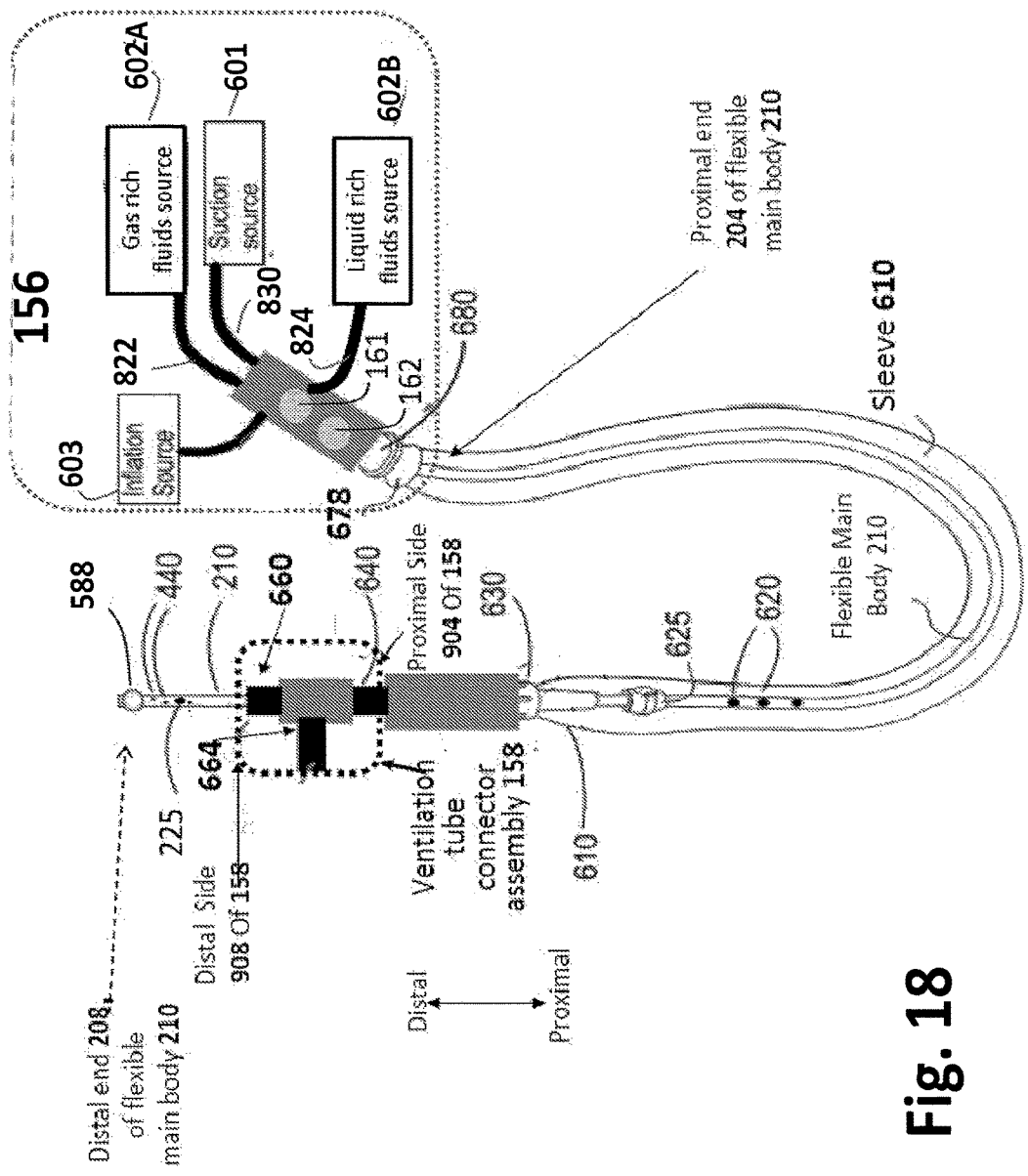

FIG. 17B illustrates an embodiment wherein a single fluids lumen 520 supplies both fluids delivery lumen 520 and an interior of balloon 588 with fluid (e.g. liquid and/or gas—for example, a pressurized fluid such as a pressurized liquid). The fluid travels within lumen 520—at location 516, a first portion of the fluid that has travelled within lumen 520 continues in a distal direction into balloon 588 to inflate balloon 518; a second portion of the fluid that has travelled within lumen 520 exits into proximal portion 774 of the interstitial region via fluid delivery orifice 525.

Although not a limitation, the balloon as illustrated in FIGS. 17A-17B is sealed and is not leaky—this is in contrast to the balloon of FIG. 16A which is leaky and has voids/holes therein.

In some embodiments related to FIGS. 17A and/or 17B, one or more of (i.e. any combination) the following features may be provided: (i) a single lumen 520 or a single fluids source 602 supplies fluid to fluid delivery orifice 525 and to inflatable balloon 588; and/or (ii) a single lumen 520 or a single fluids source 602 supplies fluid to fluid delivery orifice 525 and to an inflatable non-leaky or sealed balloon 588; and/or (iii) a single lumen 520 or a single fluids source 602 supplies fluid to inflatable balloon 588 and to a fluid delivery orifice 525 not located on balloon 588 (e.g. proximal to balloon 588—e.g. by at least 3 mm or at least 5 mm or at least 1 cm).

In the example of FIG. 17A, parallel lumens 580 and 520 respectively leading to an interior of balloon 588 and to fluid delivery orifice 525 are supplied with fluid (e.g. pressurized fluid—e.g. pressurized liquid or mist) by a common fluid source.

In the example of FIG. 17B, a single lumen supplies fluid (e.g. pressurized fluid) to both balloon 588 and to fluid delivery orifice 525.

FIGS. 18-22 relate to an embodiment whereby cleaning device includes a 'mist-formation assembly.' In the examples of FIGS. 18-22, a mist is formed by combining (i) a gas or gas-rich fluid (e.g. from fluid source 602A) and (ii) a liquid or liquid-rich fluid (e.g. from fluids source 602B). In some embodiments, the gas or gas-rich fluid is received into a first fluid-delivery lumen 520A (e.g. via port 822) and the liquid or liquid-rich fluid is received into a second fluid-delivery lumen 520B (e.g. via port 824). Upon mixing (i.e. at a mixing location—see for example mixing location 522 of FIG. 19A) between the two fluids, the liquid or liquid-rich fluid forms droplets which are suspended within the gas of or the gas-rich fluid, thereby forming the mist.

In some embodiments, the gas or gas-rich fluid is pressurized and/or flowing in a distal direction at some sort of 'significant flow velocity' upon exiting second fluid delivery lumen 520B via fluid delivery orifice 224 to mixing location 522. In some embodiments, there is no need for the fluids (e.g. the liquid or liquid-rich fluids) within the first fluid delivery lumen 520A or fluids of liquids-rich fluids source 602B to be pressurized. For example, the flow velocity of gas or gas-rich fluids at mixing location 522 (e.g. which is also 'close to' a fluid delivery orifice 244 via which fluids exit first fluid delivery lumen 520A) may be sufficient to induce distal motion of liquid or a liquids-rich fluid within the first fluid delivery lumen 520A to the mixing location 522 where the droplets are formed from liquid and suspended in the gas (or gas-rich fluid) flow to form the mist.

Figure 19A:
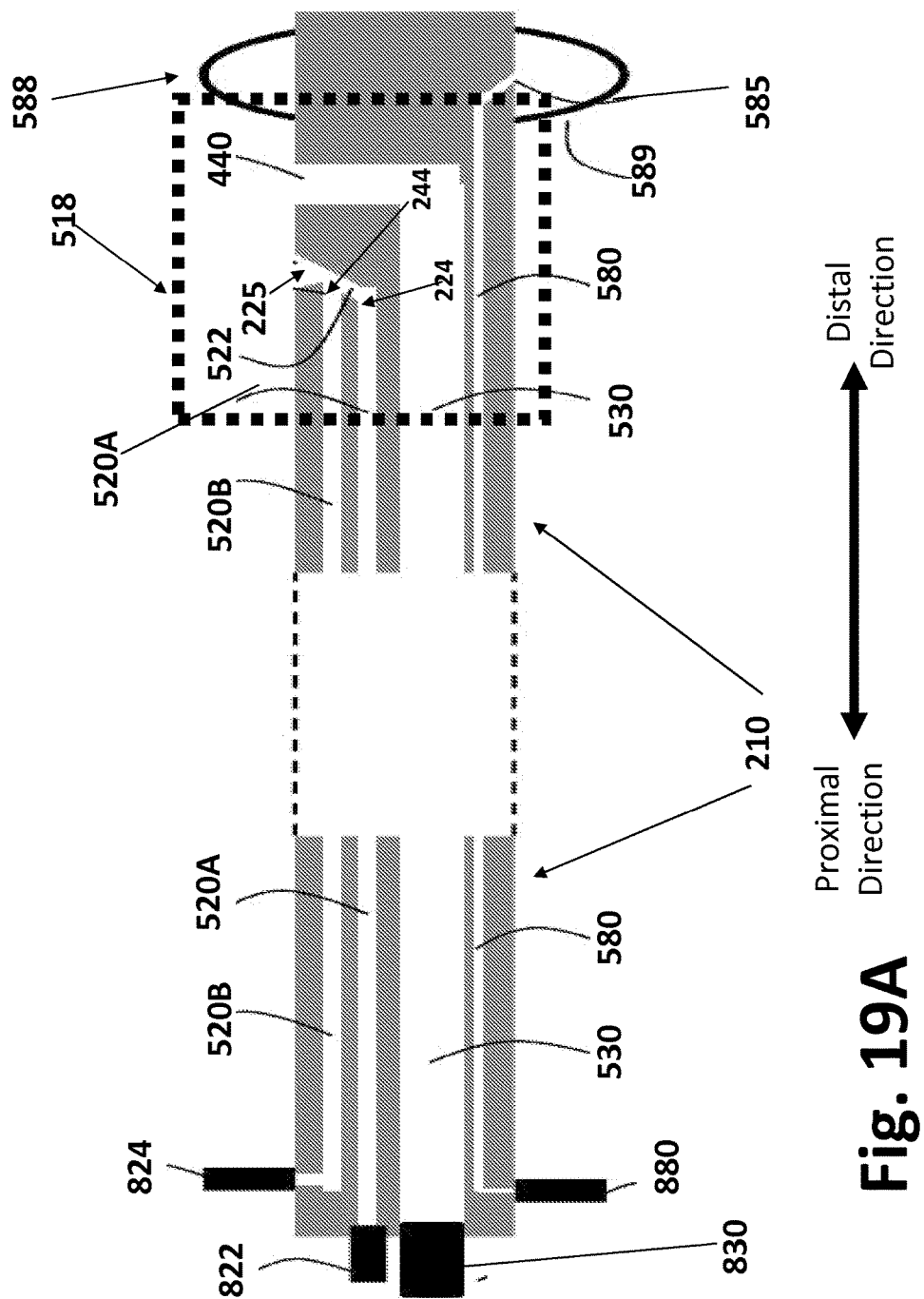
Figure 20:
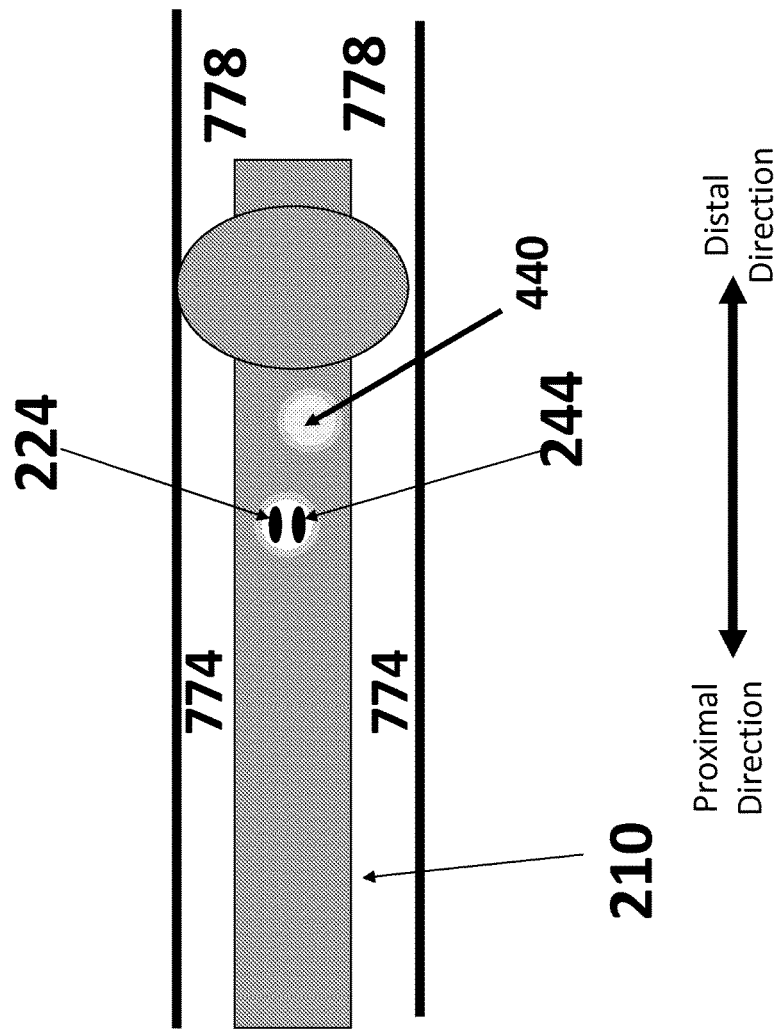
Figure 21:
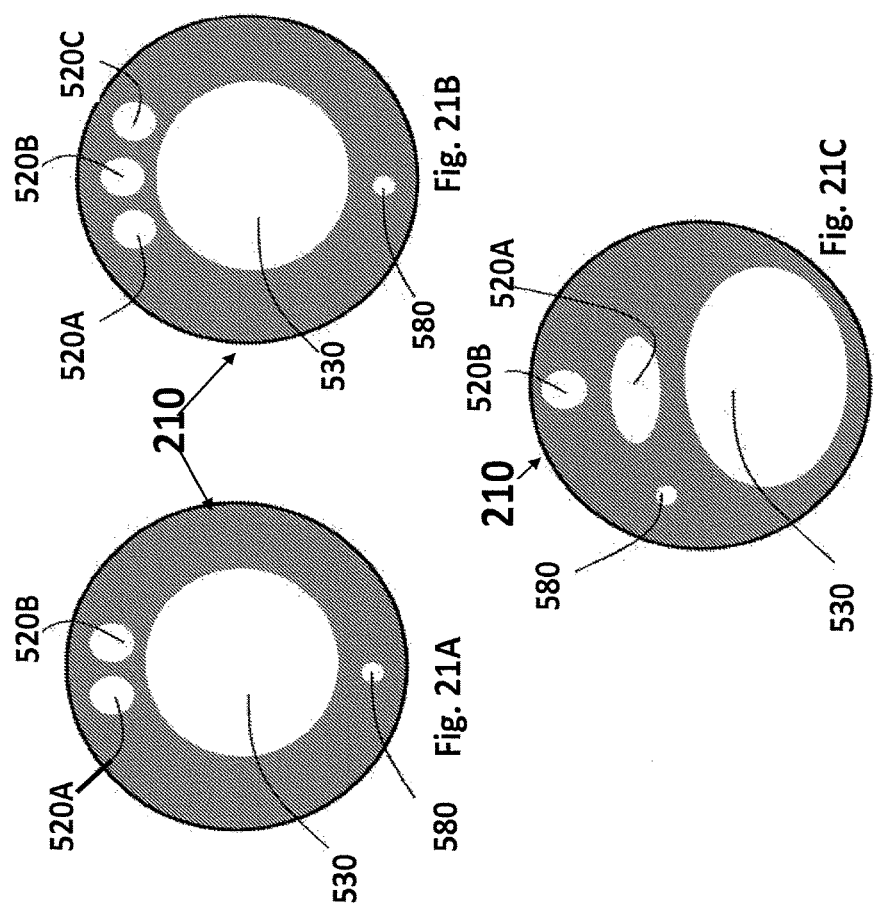

In the examples of FIG. 19A-19B, the mist may be formed at or below a surface of main body 210 or 'within main body 210' (e.g. at a location within ventilation tube 210). In the example of FIG. 20, the mist may be formed within the proximal portion 774 of interstitial region.

For both cases or for any other embodiment where mist is generated 'in situ' (i) at a location within main body 210 (e.g. within main body 210 at a location within ventilation tube); and/or (ii) at a location within proximal portion 774 of interstitial region, it may be useful to arrange fluid delivery lumens 224 and 244 to be 'close to each other'—i.e. so that a distance between 'closest locations' of fluid delivery lumens 224 and 244 (not a 'center-center distance') is at most 5 mm or at most 4 mm or at most 3 mm or at most 2 mm or at most 1 mm.

FIGS. 21A-21C are cross-sections of a main body 210 of a device including a mist-formation assembly according to some embodiments. In some embodiments, within a cross section of main body 210 the fluid delivery lumens 520A, 520B are 'close to each other' so that closest locations thereof are separated by at most 5 mm or at most 4 mm or at most 3 mm or at most 2 mm or at most 1 mm.

Figure 22:
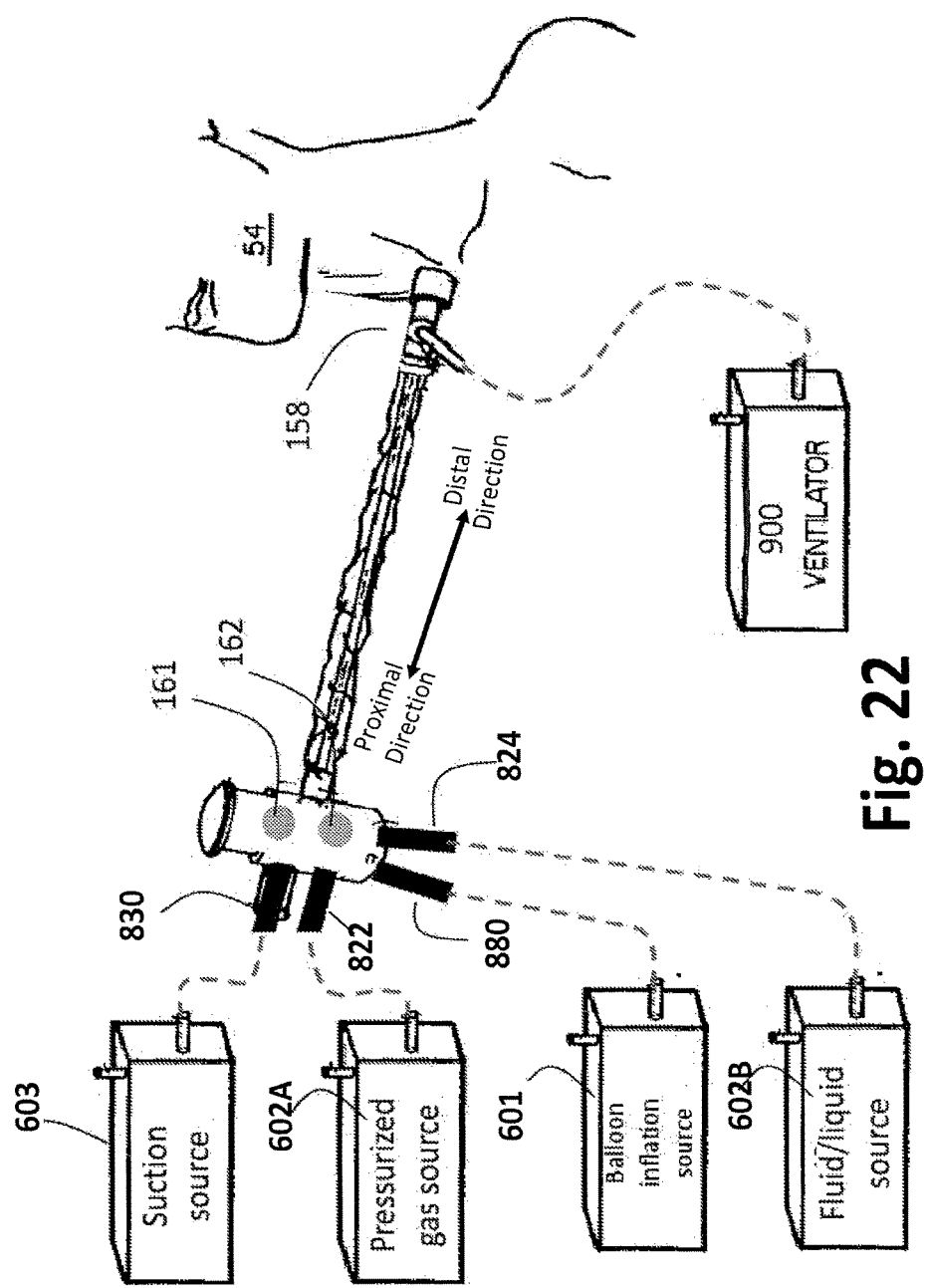
Figure 23A:
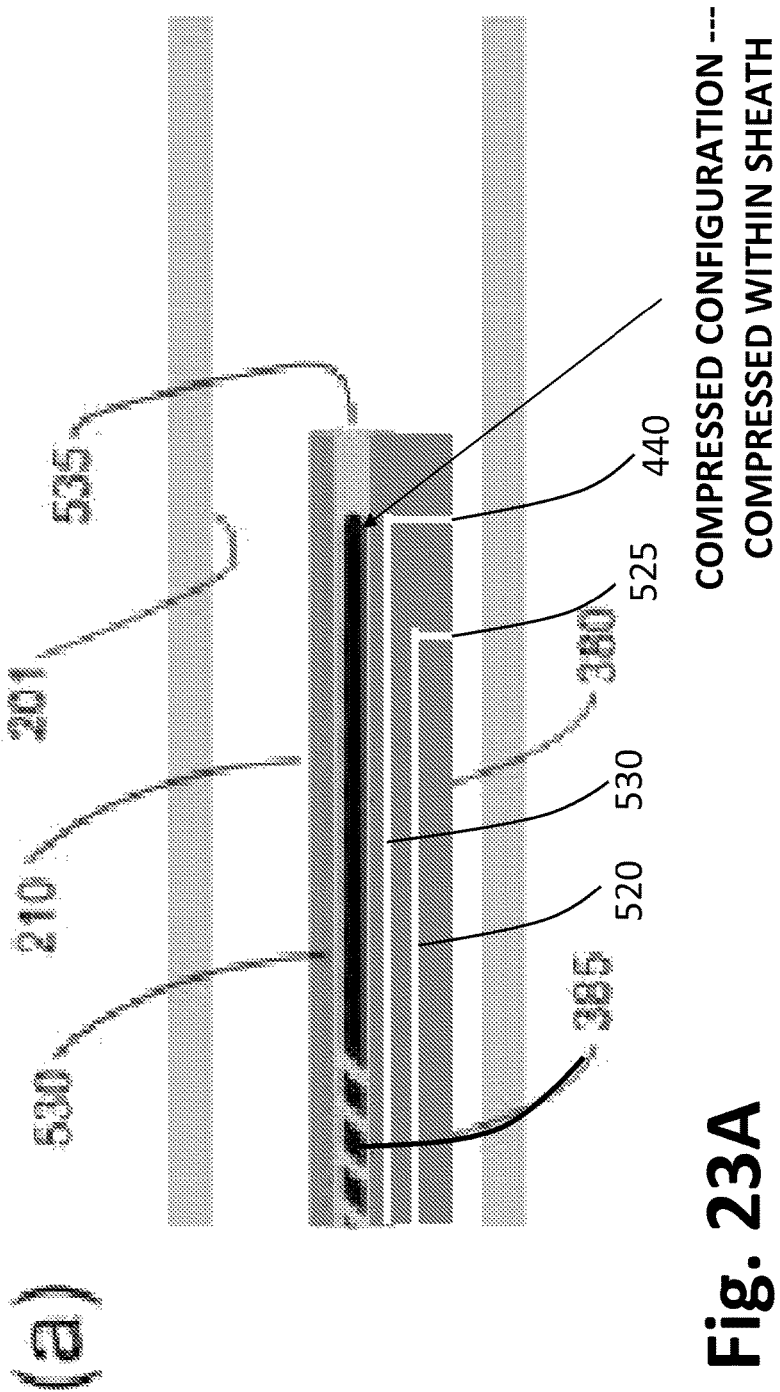
Figure 23B:
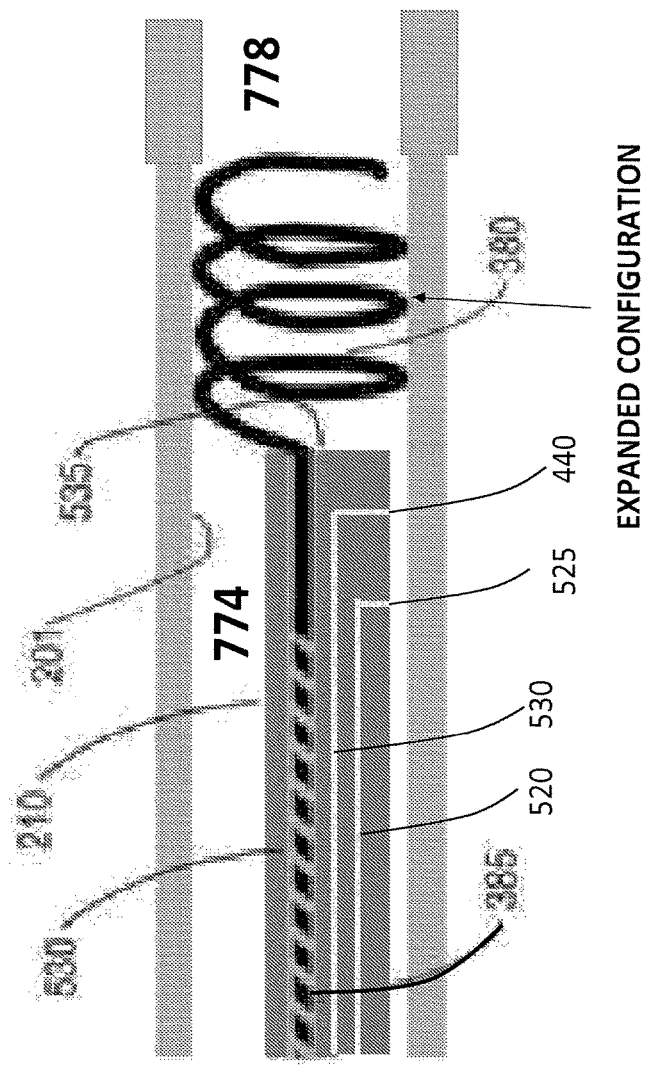

FIG. 22 is a more schematic illustration of a cleaning device including a mist formation assembly. In some embodiments, the mist formation assembly is operative, when the main body 210 is inserted through the tube-connector assembly 158 into the ventilation tube 60, to form a mist from a liquid or a liquid-rich fluid and a gas or a gas-rich fluid (e.g. supplied by respective sources 602B and 602A) so that the formed mist flows within a proximal portion 774 of the interstitial region that is proximal of to balloon 588.

As noted earlier, inflatable balloon 588 is just one example of a width-expandable wiping element.

Another example of a width-expandable wiping element is illustrated in FIGS. 23A-23B. The 'width-expandable' wiping element is expandable in a width direction defined by the elongated body 210—i.e. expandable in cross-section plane or a plane perpendicular to an elongate or central axis 202 of elongated body 210.

Inflatable balloon 588 is one example of the width-expandable wiping element—when inflated, balloon 588 may make contact with an inner surface 201 of ventilation tube 60.

Another example of a width-expandable wiping element 588 is illustrated respectively in compressed and expanded configuration respectively in FIGS. 23A-23B. For example, in FIGS. 23A-23B or in other embodiments, the wiping element 380 may be outwardly biased—when within a lumen of main body (see FIG. 23A—the lumen functions as a 'sheath') the outwardly-biased element may be constrained within the lumen so that the width (i.e. in a direction perpendicular to a central axis or elongate axis of main body 210) is relatively 'small.' This compressed configuration is illustrated in FIG. 23A.

In some embodiments, the wiping element 380 or 588 (e.g. outwardly-biased wiping element) may include a so-called shape-memory material. For example, the wiping element may be pre-shaped into a spiral shape as shown in FIGS. 23A-23B. In FIG. 23A, the wiping element is 'compressed' within main body 210—in FIG. 23B, the wiping element is moved distally relative to the 'sheath' or 'lumen' of main body. In this case, the wiping element expands to or towards its 'equilibrium shape'—in this case, a spiral shape. The spiral-shaped wiping element 380 may be contact with an interior wall 201 of ventilation tube 60, and just like was seen for the balloon-related examples, longitudinal motion of wiping element 380 may wipe material on the interior wall 201 of ventilation tube 60—for example, biofilm. The wiping element may also define a 'boundary' between proximal 774 and distal 778 portions of the interior of ventilation tube 60.

Since, in some embodiments, an inflatable balloon 588 is a special case of a width-expandable wiping element, any element which may be 'proximal' to a balloon 588 may, in some embodiments, be proximal to any width-expandable wiping element, including balloons 588 or width-expandable wiping elements other than balloons (e.g. see FIGS. 23A-23B or any other width-expandable wiping element).

Unless indicated to the contrary, in any embodiment illustrated herein in the contact of an inflatable balloon 588 (e.g. a 'boundary-forming' balloon 588), it is possible to substitute any width-expandable wiping element including those other than balloons instead.

Figure 24A:
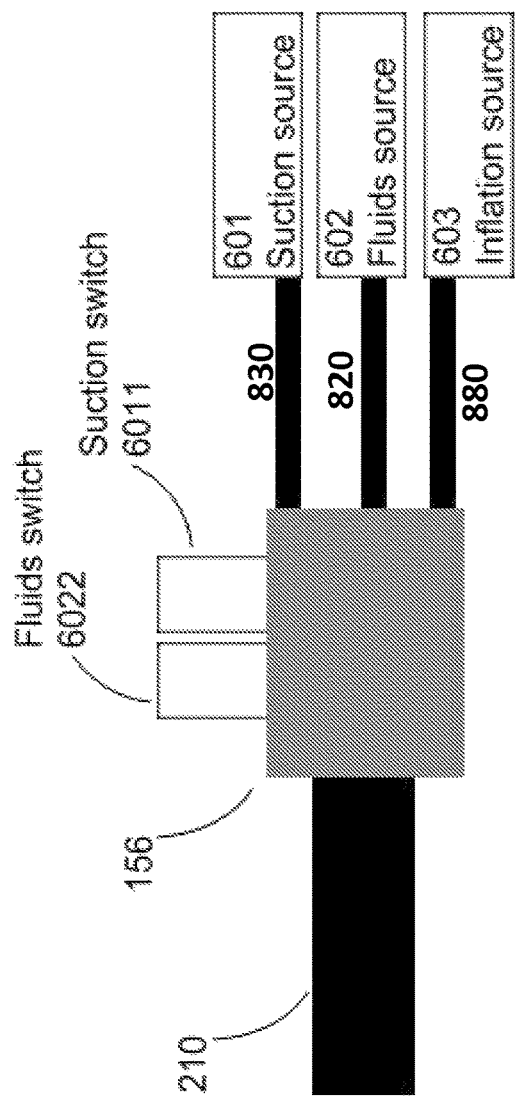
Figure 24B:
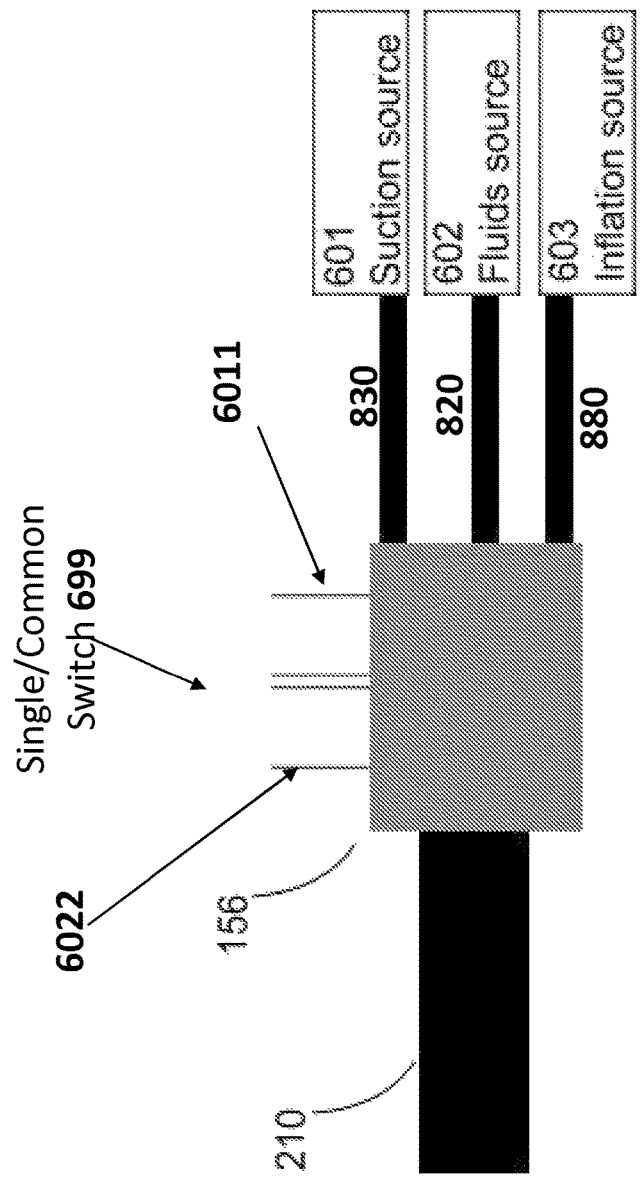

In some embodiments it is possible to manually regulate the suctioning and fluid delivery operations that are carried out within ventilation tube 60 using suction 440 and fluid delivery 525 orifices. In the example of FIG. 24A, a switching assembly is provided—for example, to regulate behavior of a valve Fluids switch 6022 regulates fluid delivery and suction switch 6011 regulates suction. In some embodiments, it is possible to easily and simultaneously control both switches. For example, a single switch may regulate both fluid delivery and suctioning—see for example, FIG. 24B. In some embodiments, any one of these switches, or both of these switches are biased to an 'off' position where there, substantially, is no suction and/or no fluid delivery.

In some embodiments, source 602 of pressurized fluid may include a syringe assembly—when the syringe is depressed, this distally forces fluid (e.g. liquid or a mist) into ventilation tube via the fluid delivery lumen.

Alternatively or additionally, a continuous (i.e. constant or non-constant) source of suction 601 or pressurized fluid 602 may be provided.

Figure 25:
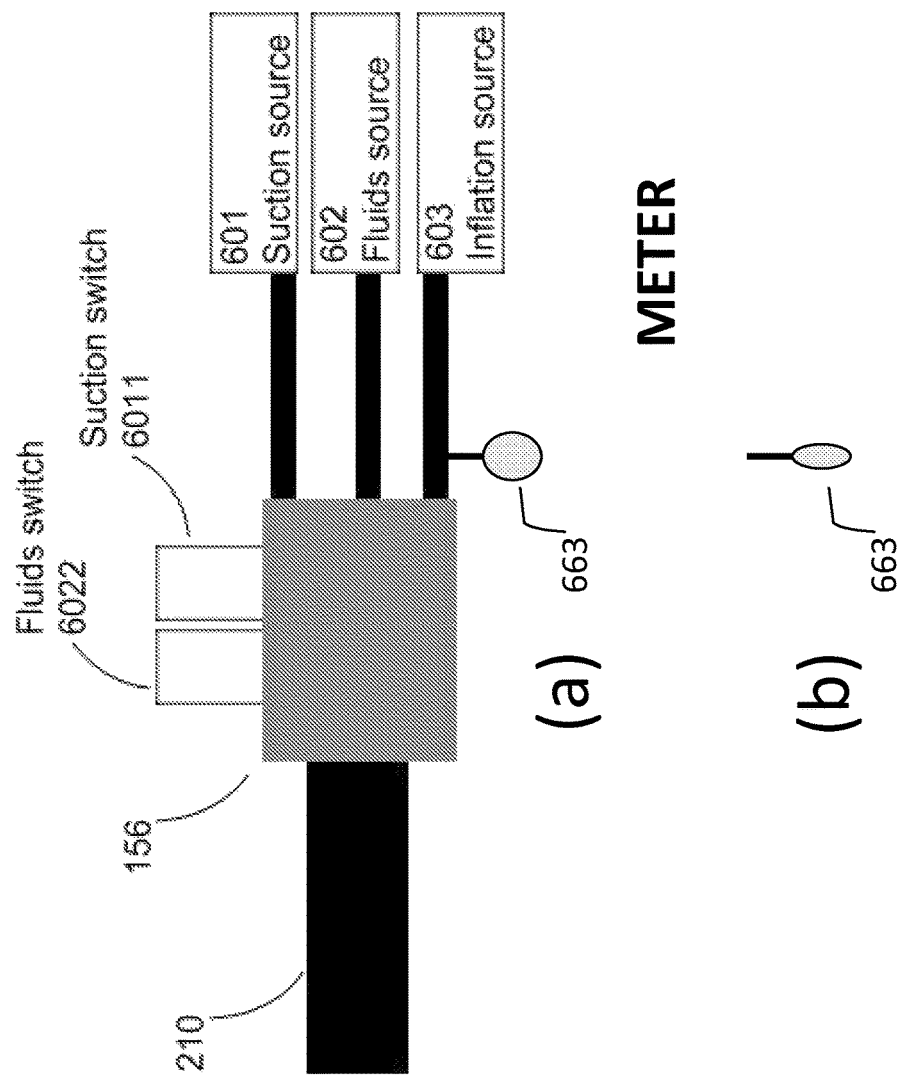

The example of FIG. 25 relates to the case where a balloon 588 (e.g. configured as a 'boundary-forming' balloon and/or as a width-expandable wiping element) is operatively linked to and/or in fluid communication with a balloon inflation indicator or meter 663 which indicates a degree to which boundary-forming balloon 588 (i.e. configured as a width-expandable wiping element). In FIG. 25, this is illustrated for the case of an inflation source 603 separate from fluids source 602—however, this is not a limitation and it is possible also to meter or measure a degree of balloon inflation when the same fluids source 602 supplies fluids both to fluid delivery orifice 525 and boundary-forming balloon 588.

In one non-limiting embodiment, the balloon inflation indicator or meter 663 is itself a balloon in fluid communication with boundary-forming balloon 588 (i.e. configured as a width-expandable wiping element).

In various examples described above, suctioning was restricted by slidable boundary to locations, within the interior of the tube. In some embodiments, concurrent with the maintaining of the slidable boundary, there is no suctioning carried out distal to the slidable boundary and/or only a "small" amount of suction relative to the suctioning of material from proximal locations 774 via suctioning orifice(s) 440. For example, a ratio between the 'suctioning flow' rate of material from the distal locations 778 to the 'suctioning flow' rate of material from the proximal 774 locations may be at most 0.25 or at most 0.2 or at most 0.1 or at most 0.05.

One feature provided by some embodiments is that when boundary-forming balloon 588 is inflated so that boundary is maintained, there is little or no suction/negative pressure applied to locations 778 distal of the boundary. Not wishing to be bound by any theory, the inventors presently believe that application so such 'distal' suction while boundary is maintained may reduce an amount of air available to the patient and/or located in the patient's trachea precisely during the short period of time when the balloon 588/boundary block air from the ventilator from reaching the patient's lungs.

Figure 26A:
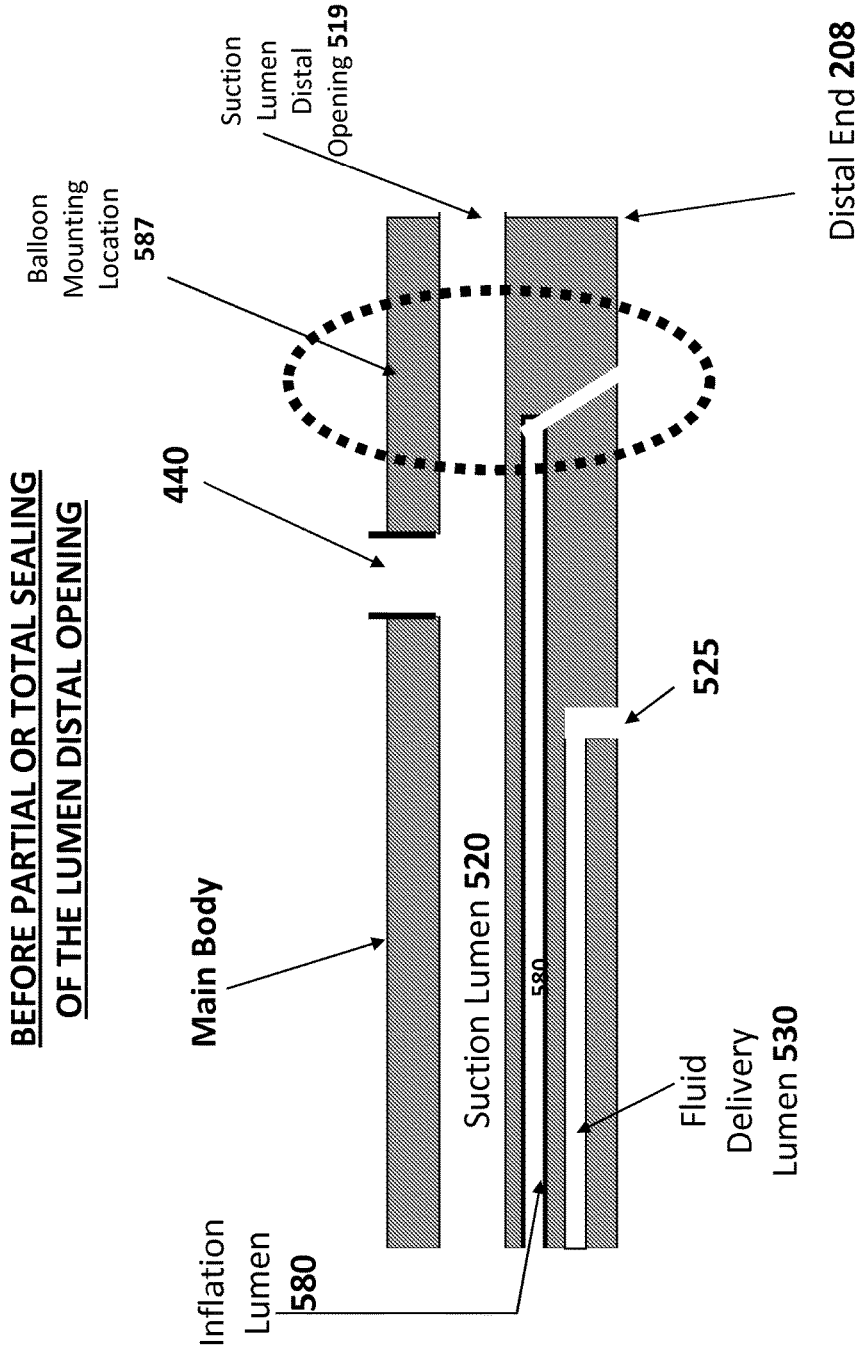
Figure 26B:
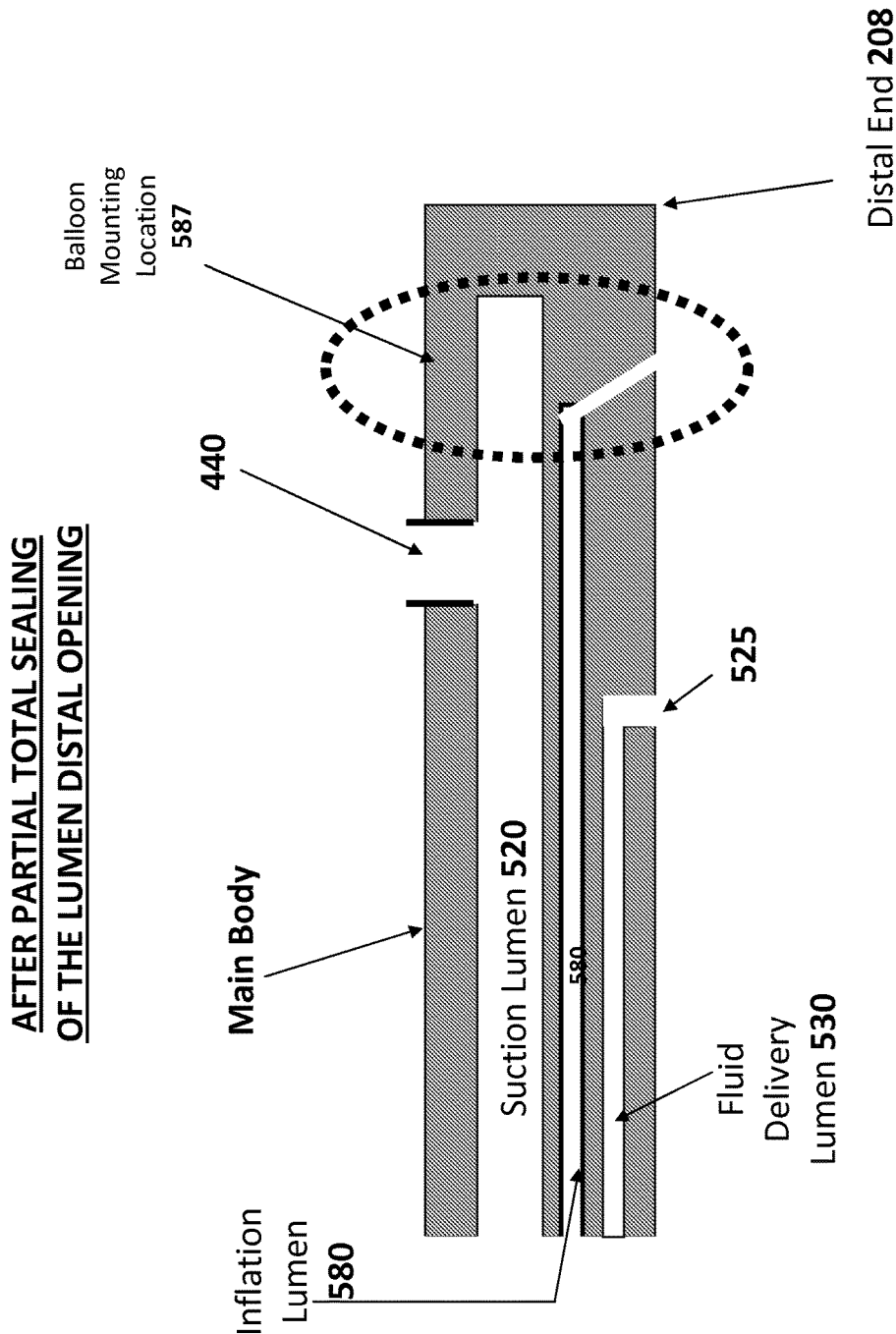
Figure 26C:
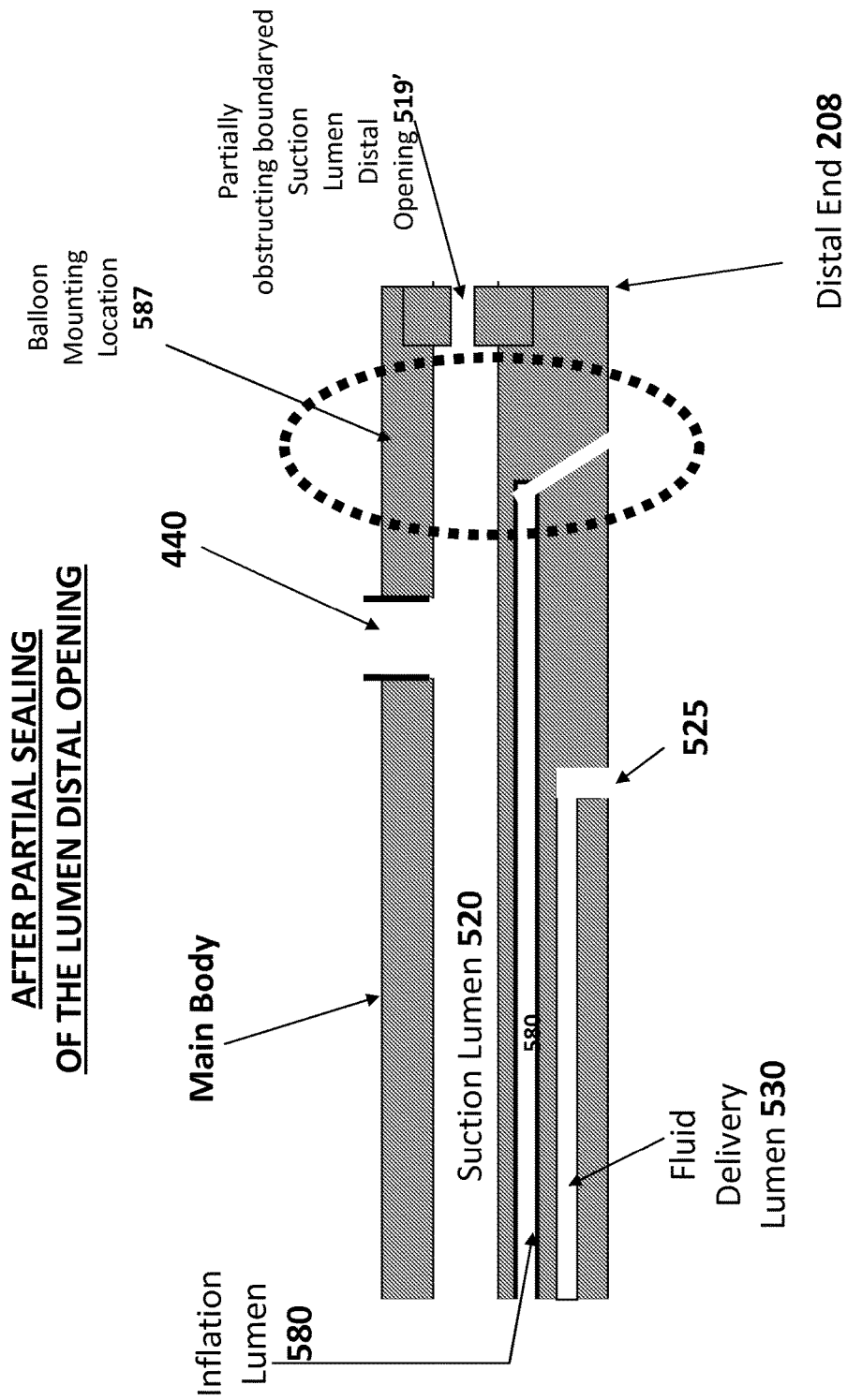
Figure 29:
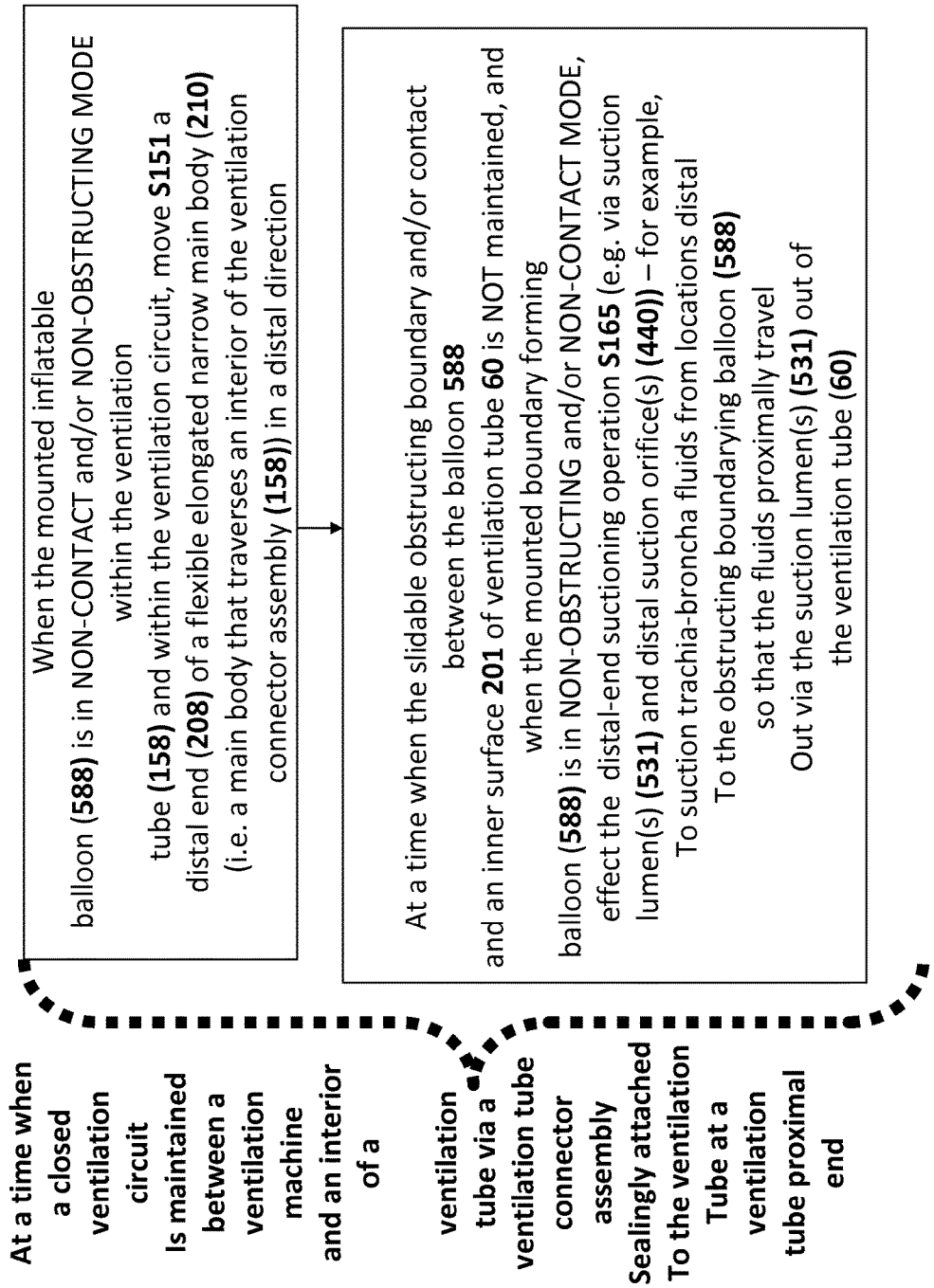

FIGS. 26A-26C describes a manufacturing technique which, in some non-limiting embodiments, is useful to facilitating this feature. During an earlier stage of manufacturing (FIG. 26A), suction lumen 520 and/or suction orifice(s) 440 is in fluid communication with a distal opening 519 which is located distal of the balloon mounting location 587 to which balloon 588 is mounted (for example, mounted at a later time). During a later stage of manufacturing, it is possible to completely (see FIG. 26B) or at least partially (see FIG. 26C) block this opening 519. There is no limitation on how this may be accomplished—appropriate techniques include melting the lumen (e.g. near opening 519) so as to close opening 519 or introduction of glue or any other foreign materials into 520 (e.g. near 519). Blocking of 519 creates some sort of 'blocking element' or 'blocking structure' which partially or completely blocks opening 519.

In some embodiments, after balloon 588 is inflated to create boundary, an interior of suction lumen 520 (e.g. at a 'half-way' location halfway between proximal 204 and distal 208 ends of main body 210 and/or at a location that is 3 cm or 5 cm or 10 cm proximal to balloon mounting location 587 or balloon 588) and/or one or more or all of suction lumen(s) 440 (e.g. located proximal to balloon mounting location 587) is not in substantially fluid communication with any location 778 outside of main body 210 and distal to boundary and/or is only in fluid communications with one or more opening(s) 519 whose total aggregate size is relatively 'small' relative to an aggregate size of suction port(s) 440 open to proximal locations 774 and/or located proximal to mounting location 587 or balloon 588.

This, in exemplary embodiments, the device is configured, when sleeve 770 is maintained, to substantially restrict suction/negative pressure to proximal locations 774—for example, at most 30% or at most 20% or at most 10% of a total negative pressure applied within an interior of tube 60 and/or applied via suction lumen 520 and/or via all suction lumen(s) 520 within or along main body 210 is applied to distal locations 778—i.e. a significant majority or an entirety of the negative pressure is restricted (i.e. by the presence of inflatable balloon 588 which maintains the 'obstructing boundary') to proximal location(s) 774.

In some embodiments, one or more of the suction orifice(s) 440 (e.g. proximal to mounting location 587 or balloon 588 or boundary and/or open to proximal locations 774) (e.g. which is supplied or primarily supplied with negative pressure via suction lumen(s) 520) is in fluid communication, through suction lumen 520, with a 'blocking element' or 'blocking structure' which partially or completely blocks opening 519.

Some additional features (e.g. related to numerical parameters) are discussed in the present section. As with all features, they are intended as exemplary and not as limiting.

There is no limitations on the material from which any element (e.g. main body, lumen(s), orifice(s), balloon, etc) may be constructed. In non limiting embodiments, material used may include, but are not limited to biocompatible materials, polymer-based materials, plastics, silicone, polyurethane and latex. As the skilled artisan will appreciated after reading the present disclosure, other materials may be used.

In various embodiments (not limited to the embodiments of FIG. 4A or in any other figure), there is no particular limitation on the size of the fluid delivery orifice(s) 525 and/or suction 440 orifice(s).

In some embodiments, an average suction lumen(s) 520 width (e.g. averaged over a longitudinal direction) is between 2 and 5 mm. In some embodiments, an average fluide delivery lumen(s) 530 width (e.g. averaged over a longitudinal direction) is at most 0.75 or at most 0.5 or at most 0.25 or at most 0.2 or at most 0.15 or at most 0.1 times an average suction lumen(s) 520 width.

In some embodiments, an inner width of one or more of the fluid delivery orifice(s) 525, or an average orifice inner width for any number (i.e. 2 or 3 or 4 or any other number) of fluid delivery orifice(s) 525 is at most 3 mm or at most 2 mm or at most 1 mm or at most 0.75 mm or at most 0.5 mm and/or at least 0.25 mm or at least 0.5 mm or at least 1 mm.

In some embodiments, an inner width of one or more of the suction orifice(s) 440, or an average orifice inner width for any number (i.e. 2 or 3 or 4 or any other number) of suction orifice(s) 440 is at most 7 mm or at most 3 mm or at most 2 mm and/or at least 0.5 mm or at least 1 mm or at least 2 mm or at least 3 mm or at least 4 mm.

In some embodiments, an inner width of one or two or three or any number of fluid delivery orifice(s) 525 is at most 50% or at most 30% or at most 20% or at most 15% of an inner width of one or two or three or any number of suction orifice(s) 440.

In some embodiments, one or more of the suction 440 and/or fluid delivery 525 orifice(s) is deployed at most 5 cm or at most 3 cm or at most 2 cm or at most 1 cm proximal to a balloon mounting location 770 and/or an average or proximal location of boundary-forming balloon 588 and/or a location of boundary.

In some embodiments, an cross section of the suction lumen 530 exceeds a cross section of fluid delivery lumen 530 by a factor of at least 1.5 or a factor of at least 2 or a factor of at least 4 or a factor of at least 5 or a factor of between 6 and 15 or a factor of between 8 and 12.

It is now disclosed a ballooned cleaning device for use with an ETT or tracheostomy ventilation tube 60, a ventilator machine 900, a source(s) 602 of pressurized liquid and a source(s) of suctioning 603, the cleaning device comprising:
 a. a tube-connector assembly 158 for connecting the ventilation tube 60 to the ventilator machine 900, in a substantially air-tight manner;
 b. an elongate, flexible, main body 210 that is insertable through the tube-connector assembly 158 into the ventilation tube 60 to form an interstitial region outside of the main body 210 within ventilation tube 60;
 c. a balloon 588 mounted to the main body 210 at a location in the distal half of the main body and inflatable into contact with an inner surface 201 of the ventilation tube 60;
 d. one or more liquid-delivery lumen(s) 520 arranged within or along the elongated main body, and operative to transport pressurized liquid received from pressurized liquid source(s) outside of the ventilation tube 60, into a proximal portion 774 of the interstitial region that is proximal of the balloon 588 so that the transported liquid enters the proximal portion 774 via liquid delivery orifice(s) 525 located on or mechanically coupled to the main body 210;
 e. suction lumen(s) 530 arranged within or along the main body 210, and operative to convey negative pressure from suction source(s) 603 predominantly into the proximal portion 774 of interstitial region via suction orifice(s) 440 when balloon 588 is inflated into contact, suction orifice(s) 440 being open to the proximal portion 774 and mechanically coupled to the main body 210;
 f. a suction port 830 connectable to the suction source(s) 603 for mediating a connection between the suction source and the suction lumen(s); and
 g. a pliable sleeve 610 around at least a portion of the main body 210 in locations proximal to the tube-connector assembly 158 and distal to the suction port 830 to inhibit contamination.

In some embodiments, at least one of the fluid delivery orifice(s) 525 is a void in the balloon 588 so that the balloon 588 is leaky.

In some embodiments, the inflatable balloon is operative to be inflated by pressurized fluid source via fluid delivery lumen(s) 520.

In some embodiments,
 i. inflatable balloon 588 is a leaky balloon having one or more surface-located leak holes; and
 ii. one or more of the fluid delivery orifice(s) 525 are leak holes that face in a direction having a proximal component; and
 iii. inflatable balloon is operative to be inflated by pressurized fluid source via fluid delivery lumen(s) 520.

In some embodiments,
 i. balloon 588 is a boundary-forming balloon which divides an interior of the ventilation tube into more proximate 774 and more distal 778 portions;
 ii. at least one of the at least one of the fluid delivery orifice(s) 525 is a void in the boundary-forming balloon 588 so that the boundary-forming balloon 588 is leaky;
 iii. forcing of pressurized liquid into the boundary-forming balloon 588 is operative both:
   A. to inflate boundary-forming balloon 588;
   B. to cause the pressurized liquid to enter the proximal portion 774 via liquid delivery orifice(s) 525 located on or mechanically coupled to the main body 210.

In some embodiments, the boundary-forming balloon 588 forms a seal between the proximate 774 and distal 778 portions of the interstitial region.

In some embodiments, the boundary-forming balloon 588 does not form a seal between the into proximate 774 and distal 778 portions of the interstitial region.

In some embodiments, the balloon 588 hinders and/or at least partially obstructs fluid communications between the more proximal and more distal portions.

It is now disclosed a cleaning device for use with an ETT or tracheostomy ventilation tube 60, a ventilator machine 900, a source(s) of fluid and a source(s) of suctioning 603, the cleaning device comprising:
 a. a tube-connector assembly 158 for connecting the ventilation tube 60 to the ventilator machine 900, in a substantially air-tight manner;

b. an elongate, flexible, main body 210 that is insertable through the tube-connector assembly 158 into the ventilation tube 60 to form an interstitial region outside of the main body 210 within ventilation tube 60;

c. a balloon 588 mounted to the main body 210 at and inflatable into contact with an inner surface 201 of the ventilation tube 60;

d. one or more fluid delivery lumen(s) 520 arranged within or along the elongated main body, and operative to transport pressurized fluid received from pressurized fluid source(s) outside of the ventilation tube 60, into a proximal portion 774 of the interstitial region that is proximal of the balloon 588 so that the transported fluid enters the proximal portion 774 via fluid delivery orifice(s) 525 located on or mechanically coupled to the main body 210;

e. suction lumen(s) 530 arranged within or along the main body, and operative to convey negative pressure from suction source(s) 603 predominantly into the proximal portion 774 of interstitial region via suction orifice(s) 440 when balloon 588 is inflated into contact, suction orifice(s) 440 being open to the proximal portion 774 and mechanically coupled to the main body 210.

f. a suction port 830 connectable to the suction source(s) 603 for mediating a connection between the suction source and the suction lumen(s); and g. a pliable sleeve 610 around at least a portion of the main body 210 in locations proximal to the tube-connector assembly 158 and distal to the suction port 830 to inhibit contamination.

It is now disclosed a ballooned cleaning device for use with an ETT or tracheostomy ventilation tube 60, a ventilator machine 900, a source(s) of fluid and a source(s) of suctioning 603, the cleaning device comprising:

a. a tube-connector assembly 158 for connecting the ventilation tube 60 to the ventilator machine 900, in a substantially air-tight manner;

b. an elongate, flexible, main body 210 that is insertable through the tube-connector assembly 158 into the ventilation tube 60 to form an interstitial region outside of the main body 210 within ventilation tube 60;

c. a balloon 588 mounted to the main body 210 at and inflatable into contact with an inner surface 201 of the ventilation tube 60;

d. one or more fluid delivery lumen(s) 520 arranged within or along the elongated main body, and operative to transport fluid received from fluid source(s) outside of the ventilation tube 60, into a proximal portion 774 of the interstitial region that is proximal of the balloon 588 so that the transported fluid enters the proximal portion 774 via fluid delivery orifice(s) 525 located on or mechanically coupled to the main body 210;

e. suction lumen(s) 530 arranged within or along the main body, and operative to convey negative pressure from suction source(s) 603 predominantly into the proximal portion 774 of interstitial region via suction orifice(s) 440 when balloon 588 is inflated into contact, suction orifice(s) 440 being open to the proximal portion 774 and mechanically coupled to the main body 210.

f. a suction port 830 connectable to the suction source(s) 603 for mediating a connection between the suction source and the suction lumen(s); and g. a pliable sleeve 610 around at least a portion of the main body 210 in locations proximal to the tube-connector assembly 158 and distal to the suction port 830 to inhibit contamination.

It is now disclosed a ballooned cleaning device for use with an ETT or tracheostomy ventilation tube 60, a ventilator machine 900, a source(s) of fluid and a source(s) of suctioning 603, the cleaning device comprising:

a. a tube-connector assembly 158 for connecting the ventilation tube 60 to the ventilator machine 900, in a substantially air-tight manner;

b. an elongate, flexible, main body 210 that is insertable through the tube-connector assembly 158 into the ventilation tube 60 to form an interstitial region outside of the main body 210 within ventilation tube 60;

c. a balloon 588 mounted to the main body 210 at a location inflatable into contact with an inner surface 201 of the ventilation tube 60;

d. suction lumen(s) 530 arranged within or along the main body, and operative to convey negative pressure from suction source(s) 603 predominantly into the proximal portion 774 of interstitial region via suction orifice(s) 440 when balloon 588 is inflated into contact, suction orifice(s) 440 being open to the proximal portion 774 and mechanically coupled to the main body 210;

e. a fluid delivery orifice(s) in fluid communication with a proximal portion 774 of the interstitial region that is proximal of the balloon 588 so that the fluid from the fluid source passing through the fluid delivery orifice enters the proximal portion 774;

f. a suction port 830 connectable to the suction source(s) 603 for mediating a connection between the suction source and the suction lumen(s); and g. a pliable sleeve 610 around at least a portion of the main body 210 in locations proximal to the tube-connector assembly 158 and distal to the suction port 830 to inhibit contamination.

It is now disclosed a ballooned cleaning device for use with an ETT or tracheostomy ventilation tube 60, a ventilator machine 900, and a source(s) of suctioning 603, the cleaning device comprising:

a. a tube-connector assembly 158 for connecting the ventilation tube 60 to the ventilator machine 900, in a substantially air-tight manner;

b. an elongate, flexible, main body 210 that is insertable through the tube-connector assembly 158 into the ventilation tube 60 to form an interstitial region outside of the main body 210 within ventilation tube 60;

c. a balloon 588 mounted to the main body 210 at a location inflatable into contact with an inner surface 201 of the ventilation tube 60;

d. suction lumen(s) 530 arranged within or along the main body, and operative to convey negative pressure from suction source(s) 603 predominantly into the proximal portion 774 of interstitial region via suction orifice(s) 440 when balloon 588 is inflated into contact, suction orifice(s) 440 being open to the proximal portion 774 and mechanically coupled to the main body 210;

e. a suction port 830 connectable to the suction source(s) 603 for mediating a connection between the suction source and the suction lumen(s); and f. a pliable sleeve 610 around at least a portion of the main body 210 in locations proximal to the tube-connector assembly 158 and distal to the suction port 830 to inhibit contamination.

It is now disclosed a ballooned cleaning device for use with an ETT or tracheostomy ventilation tube 60, a ventilator machine 900, a source(s) of fluid and a source(s) of suctioning 603, the cleaning device comprising:

a. an elongate, flexible, main body 210 that into the ventilation tube 60 to form an interstitial region outside of the main body 210 within ventilation tube 60;
b. an inflatable balloon 588 mounted to the main body 210 and inflatable when within the ventilation tube 60;
c. one or more fluid delivery lumen(s) 520 arranged within or along the elongated main body, and operative to transport fluid received from fluid source(s) outside of the ventilation tube 60, into a proximal portion 774 of the interstitial region that is proximal of the balloon 588 so that the transported fluid enters the proximal portion 774 via fluid delivery orifice(s) 525 located on or mechanically coupled to the main body 210;
d. suction lumen(s) 530 arranged within or along the main body, and operative to convey negative pressure from suction source(s) 603 via suction orifice(s) 440 when balloon 588 is inflated into contact, suction orifice(s) 440 being open to the proximal portion 774 and mechanically coupled to the main body 210.

It is now disclosed a ballooned cleaning device for use with an ETT or tracheostomy ventilation tube 60, a ventilator machine 900, a source(s) of fluid and a source(s) of suctioning 603, the cleaning device comprising:
a. an elongate, flexible, main body 210 that into the ventilation tube 60 to form an interstitial region outside of the main body 210 within ventilation tube 60;
b. an inflatable balloon 588 mounted to the main body 210 and inflatable towards an inner surface 201 the ventilation tube 60;
c. a fluid delivery orifice(s) 525 in fluid communication with a proximal portion 774 of the interstitial region that is proximal of the balloon 588 so that the fluid from the fluid source passing through the fluid delivery orifice enters the proximal portion 774;
d. suction lumen(s) 530 arranged within or along the main body, and operative to convey negative pressure from suction source(s) 603 via suction orifice(s) 440 when balloon 588 is inflated into contact, suction orifice(s) 440 being open to the proximal portion 774 and mechanically coupled to the main body 210.

In some embodiments, the balloon 588 is inflatable into contact with an inner surface 201 of the ventilation tube 60

In some embodiments, further comprising at least one of:
i. a tube-connector assembly 158 for connecting the ventilation tube 60 to the ventilator machine 900, in a substantially air-tight manner; and/or
ii. a suction port 830 connectable to the suction source(s) 603 for mediating a connection between the suction source and the suction lumen(s).

In some embodiments, the main body is insertable through the tube-connector assembly 158 into the ventilation tube 60 and/or the fluid delivery orifice is located on or mechanically coupled to the main body 210.

In some embodiments, further comprising a pliable sleeve 610 around at least a portion of the main body 210 in locations proximal to the tube-connector assembly 158 and distal to the suction port 830 to inhibit contamination.

In some embodiments, the balloon is fluid-inflatable, and the device is configured so that for a given fluid delivery lumen 520, a first portion of fluid flowing through the given fluid delivery lumen enters into the proximal portion 774 after passing through fluid delivery orifice(s) 525, and a second portion of fluid flowing through the given fluid delivery lumen inflates balloon 588.

In some embodiments, balloon 588 is leaky and fluid delivery orifice(s) that is supplied by fluid via the given fluid delivery lumen 520 is located on a surface 589 of balloon 588.

In some embodiments, the balloon 588 is sealed and fluid delivery orifice(s) that is supplied by fluid via the given fluid delivery lumen 520 is not located on a surface 589 of balloon 588.

In some embodiments, fluid delivery orifice(s) that is supplied by fluid via the given fluid delivery lumen 520 is located proximal to balloon 588.

It is now disloswed a cleaning device for use with an ETT or tracheostomy ventilation tube 60, a ventilator machine 900, a source(s) of fluid and a source(s) of suctioning 603, the cleaning device comprising:
a. a tube-connector assembly 158 for connecting the ventilation tube 60 to the ventilator machine 900, in a substantially air-tight manner;
b. an elongate, flexible, main body 210 that is insertable through the tube-connector assembly 158 into the ventilation tube 60 to form an interstitial region outside of the main body 210 within ventilation tube 60;
c. a width-expandable wiping element 588 mounted to the main body 210 and width-expandable in a direction perpendicular to an elongate axis of the main body 210 into contact with an inner surface 201 of the ventilation tube 60;
d. one or more fluid delivery lumen(s) 520 arranged within or along the elongated main body, and operative to transport fluid received from fluid source(s) outside of the ventilation tube 60, into a proximal portion 774 of the interstitial region that is proximal of the wiping element 588 so that the transported fluid enters the proximal portion 774 via fluid delivery orifice(s) 525 located on or mechanically coupled to the main body 210;
e. suction lumen(s) 530 arranged within or along the main body, and operative to convey negative pressure from suction source(s) 603 predominantly into the proximal portion 774 of interstitial region via suction orifice(s) 440 when wiping element 588 is expanded into contact, suction orifice(s) 440 being open to the proximal portion 774 and mechanically coupled to the main body 210;
f. a suction port 830 connectable to the suction source(s) 603 for mediating a connection between the suction source and the suction lumen(s); and
g. a pliable sleeve 610 around at least a portion of the main body 210 in locations proximal to the tube-connector assembly 158 and distal to the suction port 830 to inhibit contamination.

It is now disclosed a cleaning device for use with an ETT or tracheostomy ventilation tube 60, a ventilator machine 900, a source(s) of fluid and a source(s) of suctioning 603, the cleaning device comprising:
a. a tube-connector assembly 158 for connecting the ventilation tube 60 to the ventilator machine 900, in a substantially air-tight manner;
b. an elongate, flexible, main body 210 that is insertable through the tube-connector assembly 158 into the ventilation tube 60 to form an interstitial region outside of the main body 210 within ventilation tube 60;
c. a width-expandable wiping element 588 mounted to the main body 210 and width-expandable in a direction perpendicular to an elongate axis of the main body 210 into contact with an inner surface 201 of the ventilation tube 60;

d. suction lumen(s) 530 arranged within or along the main body, and operative to convey negative pressure from suction source(s) 603 predominantly into the proximal portion 774 of interstitial region via suction orifice(s) 440 when the width-expandable wiping element 588 is expanded into contact, suction orifice(s) 440 being open to the proximal portion 774 and mechanically coupled to the main body 210;

e. a fluid delivery orifice(s) in fluid communication with a proximal portion 774 of the interstitial region that is proximal of the wiping element 588 so that the fluid from the fluid source passing through the fluid delivery orifice enters the proximal portion 774;

f. a suction port 830 connectable to the suction source(s) 603 for mediating a connection between the suction source and the suction lumen(s); and g. a pliable sleeve 610 around at least a portion of the main body 210 in locations proximal to the tube-connector assembly 158 and distal to the suction port 830 to inhibit contamination.

It is now disclosed a cleaning device for use with an ETT or tracheostomy ventilation tube 60, a ventilator machine 900, a source(s) of fluid and a source(s) of suctioning 603, the cleaning device comprising:

a. a tube-connector assembly 158 for connecting the ventilation tube 60 to the ventilator machine 900, in a substantially air-tight manner;

b. an elongate, flexible, main body 210 that is insertable through the tube-connector assembly 158 into the ventilation tube 60 to form an interstitial region outside of the main body 210 within ventilation tube 60;

c. a width-expandable wiping element 588 mounted to the main body 210 and width-expandable in a direction perpendicular to an elongate axis of the main body 210 into contact with an inner surface 201 of the ventilation tube 60;

d. first 220 and second 240 fluid delivery lumen(s) arranged within or along the elongated main body, and operative to transport fluid, received respectively from first and second fluid source(s) outside of the ventilation tube 60, into a proximal portion 774 of the interstitial region that is proximal of the wiping element 588 so that the:
  (i) transported fluid from both fluid delivery lumen(s) enters the proximal portion 774 via a common fluid delivery orifice(s) 225 located on or mechanically coupled to the main body 210; or
  (ii) fluid respectively transported through the first 220A and second 220B fluid delivery lumen(s) respectively enters the proximal portion 774 via first 224 and second 244 orifices that are separated from each other by at most 5 mm and that are each located on or mechanically coupled to the main body 210;

e. suction lumen(s) 530 arranged within or along the main body, and operative to convey negative pressure from suction source(s) 603 predominantly into the proximal portion 774 of interstitial region via suction orifice(s) 440 when wiping element 588 is expanded into contact, suction orifice(s) 440 being open to the proximal portion 774 and mechanically coupled to the main body 210;

f. a suction port 830 connectable to the suction source(s) 603 for mediating a connection between the suction source and the suction lumen(s); and g. a pliable sleeve 610 around at least a portion of the main body 210 in locations proximal to the tube-connector assembly 158 and distal to the suction port 830 to inhibit contamination.

It is now disclosed a cleaning device for use with an ETT or tracheostomy ventilation tube 60, a ventilator machine 900, an array of fluid sources and a source(s) of suctioning 603, the cleaning device comprising:

a. a tube-connector assembly 158 for connecting the ventilation tube 60 to the ventilator machine 900, in a substantially air-tight manner;

b. an elongate, flexible, main body 210 that is insertable through the tube-connector assembly 158 into the ventilation tube 60 to form an interstitial region outside of the main body 210 within ventilation tube 60;

c. a width-expandable wiping element 588 mounted to the main body 210 and width-expandable in a direction perpendicular to an elongate axis of the main body 210 into contact with an inner surface 201 of the ventilation tube 60;

d. a mist formation assembly operative, when the main body 210 is inserted through the tube-connector assembly 158 into the ventilation tube 60, to form a mist from a liquid-containing fluid and a gas-containing fluid so that the formed mist flows within a proximal portion 774 of the interstitial region that is proximal of the wiping element 588 e. suction lumen(s) 530 arranged within or along the main body, and operative to convey negative pressure from suction source(s) 603 predominantly into the proximal portion 774 of interstitial region via suction orifice(s) 440 when wiping element 588 is expanded into contact, suction orifice(s) 440 being open to the proximal portion 774 and mechanically coupled to the main body 210;

f. a suction port 830 connectable to the suction source(s) 603 for mediating a connection between the suction source and the suction lumen(s); and g. a pliable sleeve 610 around at least a portion of the main body 210 in locations proximal to the tube-connector assembly 158 and distal to the suction port 830 to inhibit contamination.

In some embodiments, the mist is formed within the proximal portion 774 of the interstitial region.

In some embodiments, the mist is formed within the main body 210.

In some embodiments, when the main body is inserted through the tube-connector assembly 158 into the ventilation tube 60 to form the interstitial region, the mist is formed within the main body in location(s) within ventilation tube 60.

In some embodiments, the device is configured so that the mist enters the proximal portion 774 of the interstitial region via a fluid delivery orifice(s) open thereto, the fluid delivery orifice(s) being mechanically coupled to main body 210.

In some embodiments, the mist formation assembly includes first and second fluid-delivery lumen(s) arranged within or along the elongated main body and respectively operative to receive and transport the liquid-containing and gas-containing fluids.

In some embodiments, the mist formation assembly includes a common orifice via which material transported within the first and second fluid-delivery lumen(s) enters into the proximal portion 774 of the interstitial region.

In some embodiments, the first and second fluid-delivery lumen(s) merge within main body 210 at a merge or mixing location 522.

In some embodiments, wherein the mist is formed as fluid(s) flow from the merge location to or through a fluid delivery orifice, mechanically coupled to main body 210 and open to the proximal portion 774 of the interstitial region.

In some embodiments, the first 224 and second 244 orifices are separated from each other by at most 4 mm or at most 3 mm or at most 2 mm or at most 1 mm.

It is now disclosed a cleaning device for use with an ETT or tracheostomy ventilation tube 60, a ventilator machine 900, a source(s) of fluid and a source(s) of suctioning 603, the cleaning device comprising:
a. an elongate, flexible, main body 210 that into the ventilation tube 60 to form an interstitial region outside of the main body 210 within ventilation tube 60;
b. a width-expandable wiping element 588 mounted to the main body 210 and width-expandable in a direction perpendicular to an elongate axis of the main body 210;
c. one or more fluid delivery lumen(s) 520 arranged within or along the elongated main body, and operative to transport fluid received from fluid source(s) outside of the ventilation tube 60, into a proximal portion 774 of the interstitial region that is proximal of the wiping element 588 so that the transported fluid enters the proximal portion 774 via fluid delivery orifice(s) 525;
d. suction lumen(s) 530 arranged within or along the main body, and operative to convey negative pressure from suction source(s) 603 via suction orifice(s) 440 when wiping element 588 is expanded into contact, suction orifice(s) 440 being open to the proximal portion 774 and mechanically coupled to the main body 210.

It is now disclosed a cleaning device for use with an ETT or tracheostomy ventilation tube 60, a ventilator machine 900, a source(s) of fluid and a source(s) of suctioning 603, the cleaning device comprising:
a. an elongate, flexible, main body 210 that into the ventilation tube 60 to form an interstitial region outside of the main body 210 within ventilation tube 60;
b. a width-expandable wiping element 588 mounted to the main body 210 and width-expandable in a direction perpendicular to an elongate axis of the main body 210;
c. a fluid delivery orifice(s) 525 in fluid communication with a proximal portion 774 of the interstitial region that is proximal of the wiping element 588 so that the fluid from the fluid source passing through the fluid delivery orifice enters the proximal portion 774;
d. suction lumen(s) 530 arranged within or along the main body, and operative to convey negative pressure from suction source(s) 603 via suction orifice(s) 440 when wiping element 588 is expanded into contact, suction orifice(s) 440 being open to the proximal portion 774 and mechanically coupled to the main body 210.

In some embodiments, the width-expandable wiping element 588 is expandable into contact with an inner surface 201 of the ventilation tube 60

In some embodiments, further comprising at least one of:
i. a tube-connector assembly 158 for connecting the ventilation tube 60 to the ventilator machine 900, in a substantially air-tight manner; and/or
ii. a suction port 830 connectable to the suction source(s) 603 for mediating a connection between the suction source and the suction lumen(s).

In some embodiments, the main body is insertable through the tube-connector assembly 158 into the ventilation tube 60 and/or the fluid delivery orifice is located on or mechanically coupled to the main body 210.

In some embodiments, further comprising a pliable sleeve 610 around at least a portion of the main body 210 in locations proximal to the tube-connector assembly 158 and distal to the suction port 830 to inhibit contamination.

In some embodiments, the width-expandable wiping element is an inflatable object that width-expands upon inflation.

In some embodiments, the width-expandable wiping element is a balloon that width-expands upon inflation.

In some embodiments, the balloon 588 is inflatable via a balloon lumen 580 along or within main body 210.

In some embodiments, the balloon 588 is inflatable via one of the fluid delivery lumen(s) 520 along or within main body 210.

In some embodiments, the width-expandable wiping element is expands by a mechanism other than inflation.

In some embodiments, the width-expandable wiping element includes an outwardly biased element.

In some embodiments, the width-expandable wiping element includes an outwardly-biased shape memory device.

In some embodiments, when in an expanded configuration, the outwardly-biased shape memory is shaped as a spiral.

In some embodiments, when in the expanded configuration, the outwardly-biased shape memory is pre-shaped as a spiral having a central axis that is substantially parallel to an elongate axis of the main body 210.

In some embodiments, the outwardly biased element is a stent.

In some embodiments, the width-expandable wiping element is not outwardly biased.

In some embodiments, the width-expandable wiping element includes a rigid skeleton having a multiple configuration.

In some embodiments, a width ratio between:
i. an expanded-configuration width of the width-expandable wiping element; and
ii. a contracted-configuration width of the width-expandable wiping element is at least 1.5.

In some embodiments, a contracted-configuration width of the width-expandable wiping element is at most one-half of an inner diameter of the ventilation tube 60.

In some embodiments, a contracted-configuration width of the width-expandable wiping element is at most one-third of an inner diameter of the ventilation tube 60.

In some embodiments inflatable balloon 588 and fluid delivery orifice 525 are supplied by a common fluid supply.

In some embodiments, inflatable balloon 588 and fluid delivery orifice 525 are supplied by a common fluid supply via a common fluid delivery lumen 520.

In some embodiments, inflatable balloon 588 and fluid delivery orifice 525 are supplied by a common fluid supply respectively via first 520A and second 520B fluid delivery lumen.

In some embodiments, balloon 588 or swiping element 588 are mounted to the main body 210 in a distal half thereof.

It is now disclosed a system comprising:
any device described herein; and
source(s) of pressurized liquid 602, the device and liquid source configured, when the main body 210 is inserted within the ventilation tube 60, such that the pressurized liquid received from the fluid(s) source or a derivative thereof enters proximal portion 774 after passing through fluid delivery orifice(s).

It is now disclosed a system comprising:
any device described herein; and
source(s) of liquid 602, the device and liquid source configured, when the main body 210 is inserted within the ventilation tube 60, such that the liquid received from the fluid(s) source or a derivative thereof enters proximal portion 774 after passing through fluid delivery orifice(s).

It is now disclosed a system comprising:

any device described herein; and source(s) of pressurized fluid 602, the device and fluid source configured, when the main body 210 is inserted within the ventilation tube 60, such that the pressurized fluid received from the fluid(s) source or a derivative thereof enters proximal portion 774 after passing through fluid delivery orifice(s).

It is now disclosed a system comprising:

any device described herein; and source(s) of fluid 602, the device and liquid source configured, when the main body 210 is inserted within the ventilation tube 60, such that the fluid received from the fluid(s) source or a derivative thereof enters proximal portion 774 after passing through fluid delivery orifice(s).

In some embodiments, the fluid(s) source includes a source of unpressurized fluid.

In some embodiments, a mist is formed from a liquid-containing source and a gas containing source within main body 210 and is delivered into enters proximal portion 774.

In some embodiments, a mist is formed from a liquid-containing source and a gas containing source upon entry into proximal portion 774.

It is now disclosed a method comprising employing any device or system disclosed herein to clean biofilm from the inner surface 201 of the ventilation tube.

It is now disclosed a method comprising employing any device or system disclosed herein to prevent accumulation or hinder accumulation of biofilm from the inner surface 201 of the ventilation tube.

It is now disclosed a method of cleaning a main lumen of an ETT or tracheostomy ventilation tube 60 and/or hindering accumulation of biofilm on an inner surface of ventilation tube 60, the method comprising:

at a time when:
  i. a ventilation machine 900 is connected to the ventilation tube 60 via a tube connector assembly 158 in a substantially air-tight manner;
  ii. an elongate, flexible, main body 210 traverses an interior of the tube connector assembly 158 so that a distal end of the main body 210 is located within the ventilation tube 60 to form an interstitial region outside of the main body 210 and within the ventilator tube;
  iii. an inflatable balloon 588 mounted to the main body 210 is located within the ventilation tube 60;
  iv. sources of fluid 602 and suction 603 are respectively in fluid communication with fluid delivery orifice(s) 525 and suction orifice(s) 440, the suction 440 orifice(s) being located proximal to balloon 588 within ventilation tube 60 and on main body 210 or mechanically coupled to main body 210, carrying out the following:
  inflating the balloon 588 outwardly towards an inner surface 201 of the ventilation tube 60 and/or into contact with the inner surface 201 of the ventilation tube 60 so that both suction 440 and fluid delivery 525 orifice(s) are in fluid communication to a proximal portion 774 of the interstitial region that is proximal to inflatable balloon 588;
  concurrent with a maintaining the balloon in an inflated state, conveying negative pressure from the suction source(s) 603, via the suction lumen(s) 530 and orifice(s) 440, predominantly into the proximal portion 774 of the interstitial region; and
  concurrent with a maintaining of the balloon in the inflated state, sending fluid from the fluid source(s) 602 through the fluid delivery orifice(s) 525 into the interstitial region proximal portion 774.

It is now disclosed a method of cleaning a main lumen of an ETT or tracheostomy ventilation tube 60 and/or hindering accumulation of biofilm on an inner surface of ventilation tube 60, the method comprising:

at a time when:
  i. a ventilation machine 900 is connected to the ventilation tube 60 via a tube connector assembly 158 in a substantially air-tight manner;
  ii. an elongate, flexible, main body 210 traverses an interior of the tube connector assembly 158 so that a distal end of the main body 210 is located within the ventilation tube 60 to form an interstitial region outside of the main body 210 and within the ventilator tube;
  iii. an inflatable balloon 588 mounted to the main body 210 is located within the ventilation tube 60;
  iv. sources of fluid 602 and suction 603 are respectively in fluid communication with fluid delivery orifice(s) 525 and suction orifice(s) 440, the suction 440 orifice(s) being located proximal to balloon 588 within ventilation tube 60 and on main body 210 or mechanically coupled to main body 210, carrying out the following:
  inflating the balloon 588 into contact with the inner surface 201 of the ventilation tube 60 so that both suction 440 and fluid delivery 525 orifice(s) are in fluid communication to a proximal portion 774 of the interstitial region that is proximal to inflatable balloon 588;
  concurrent with a maintaining the balloon inflated into contact, conveying negative pressure from the suction source(s) 603, via the suction lumen(s) 530 and orifice(s) 440, predominantly into the proximal portion 774 of the interstitial region; and
  concurrent with a maintaining of the balloon inflated into contact, sending fluid from the fluid source(s) 602 through the fluid delivery orifice(s) 525 into the interstitial region proximal portion 774.

It is now disclosed a method of cleaning a main lumen of an ETT or tracheostomy ventilation tube 60 and/or hindering accumulation of biofilm on an inner surface of ventilation tube 60, the method comprising:

at a time when:
  i. a ventilation machine 900 is connected to the ventilation tube 60 via a tube connector assembly 158 in a substantially air-tight manner;
  ii. an elongate, flexible, main body 210 traverses an interior of the tube connector assembly 158 so that a distal end of the main body 210 is located within the ventilation tube 60 to form an interstitial region outside of the main body 210 and within the ventilator tube;
  iii. a width-expandable wiping element 588 mounted to the main body 210 is located within the ventilation tube 60;
  iv. sources of fluid 602 and suction 603 are and are respectively in fluid communication with fluid delivery orifice(s) 525 and suction orifice(s) 440, the suction 440 orifice(s) being located proximal to wiping element 588 within ventilation tube 60 and on main body 210 or mechanically coupled to main body 210,
carrying out the following:
a expanding the mounted width-expandable wiping element 588 towards an inner surface 201 of the ventilation tube 60 so that both suction 440 and fluid delivery 525 orifice(s) are in fluid communication to a proximal portion 774 of the interstitial region that is proximal to width-expanded wiping element 588;
concurrent with a maintaining of the width-expanded wiping element 588 in the width-expanded state, conveying negative pressure from the suction source(s) 603, via the suction lumen(s) 530 and orifice(s) 440, predominantly into the proximal portion 774 of the interstitial region; and
concurrent with a maintaining of the width-expanded wiping element 588 in the width-expanded state, sending fluid from the fluid source(s) 602 through the fluid delivery orifice(s) 525 into the interstitial region proximal portion 774.

It is now disclosed a method of cleaning a main lumen of an ETT or tracheostomy ventilation tube 60 and/or hindering accumulation of biofilm on an inner surface of ventilation tube 60, the method comprising:
at a time when:
i. a ventilation machine 900 is connected to the ventilation tube 60 via a tube connector assembly 158 in a substantially air-tight manner;
ii. an elongate, flexible, main body 210 traverses an interior of the tube connector assembly 158 so that a distal end of the main body 210 is located within the ventilation tube 60 to form an interstitial region outside of the main body 210 and within the ventilator tube;
iii. a width-expandable wiping element 588 mounted to the main body 210 is located within the ventilation tube 60;
iv. sources of fluid 602 and suction 603 are and are respectively in fluid communication with fluid delivery orifice(s) 525 and suction orifice(s) 440, the suction 440 orifice(s) being located proximal to wiping element 588 within ventilation tube 60 and on main body 210 or mechanically coupled to main body 210, carrying out the following:
a. expanding the mounted width-expandable wiping element 588 into contact with an inner surface 201 of the ventilation tube 60 so that both suction 440 and fluid delivery 525 orifice(s) are in fluid
b. communication to a proximal portion 774 of the interstitial region that is proximal to width-expanded wiping element 588;
concurrent with a maintaining of the contact by the width-expanded wiping element 588, conveying negative pressure from the suction source(s) 603, via the suction lumen(s) 530 and orifice(s) 440, predominantly into the proximal portion 774 of the interstitial region; and
c. concurrent with a maintaining of the contact by the width-expanded wiping element 588, sending fluid from the fluid source(s) 602 through the fluid delivery orifice(s) 525 into the interstitial region proximal portion 774.

In some embodiments, the suction source and/or the source of fluid(s) are located outside of ventilation tube 60.

In some embodiments, further comprising moving the expanded wiping element or inflated balloon in a longitudinal direction so as to wipe material from the inner surface of ventilation tube 60 and/or to hinder accumulation of biofilm thereon.

In some embodiments, the fluid which enters the proximal portion 774 includes a liquid.

In some embodiments, the fluid which enters the proximal portion 774 includes a mist.

In some embodiments, the fluid is sent into the interstitial region proximal portion 774 so that a liquid-containing stream of fluid flows therein, the fluid stream being sustained so that a liquid fraction thereof flows at a flow rate of at least x cc/second for at least y seconds, a value of x being at least 0.25 cc/second and a value of y being at least y seconds.

In some embodiments, x is at least 0.5 cc/second or at least 1 cc/second and/or at most 10 cc/second or at most 5 cc/second.

In some embodiments, carried out to deliver a mist into proximal region 774.

In some embodiments, carried out to form a mist within ventilation tube 60 which is formed within and/or delivered to proximal region 774.

In some embodiments, fluid cannot be delivered into proximal portion 774 when the balloon is not in contact with the inner surface 201 of ventilation tube 60 and/or is in an uninflated state.

In some embodiments, fluid cannot be delivered into proximal portion 774 when the width-expandable wiping element is not in contact with the inner surface 201 of ventilation tube 60 and/or is in an unexpanded state.

In some embodiments, an inner surface of the ventilation tube is cleaned within 15 second.

It is now disclosed a method of cleaning a main lumen of an ETT or tracheostomy ventilation tube 60 comprising:
at a time when:
i. a ventilation machine 900 is connected to the ventilation tube 60 via a tube connector assembly 158 in a substantially air-tight manner;
ii. an elongate, flexible, main body 210 traverses an interior of the tube connector assembly 158 so that a distal end of the main body 210 is located within the ventilation tube 60 to form an interstitial region outside of the main body 210 and within the ventilator tube;
iii. a balloon 588 mounted to the main body 210 is located within the ventilation tube 60;
iv. sources of pressurized fluid and/or suction 603 are:
A. any of which or both of which located in a tube-connector-assembly-proximal location outside of the ventilation tube 60 and proximal to tube connector assembly 158; and
B. are respectively in fluid communication with fluid delivery orifice(s) 525 and suction orifice(s) 440 via fluid delivery lumen(s) 520 and suction lumen(s) 530,
each of the suction 440 and fluid delivery 525 orifice(s) being:
A. located proximal to balloon 588 within ventilation tube 60, and
B. on main body 210 or mechanically coupled to main body 210,
carrying out the following steps:
a. inflating the balloon 588 mounted to the main body 210 into contact with an inner surface 201 of the ventilation tube 60 so that both suction 440 and fluid delivery 525 orifice(s) are open to a proximal portion 774 of the interstitial region that is proximal to balloon 588;

b. concurrent with a maintaining of the contact by the balloon 588, forcing pressurized fluid from the pressurized fluid source(s) 602 through the fluid delivery lumen(s) 520 and orifice(s) 525, into the interstitial region proximal portion 774;

c. concurrent with a maintaining of the contact by the balloon 588, conveying negative pressure from the suction source(s) 603, via the suction lumen(s) 530 and orifice(s) 440, predominantly into the proximal portion 774 of the interstitial region.

It is now disclosed a ballooned cleaning device for use with an ETT or tracheostomy ventilation tube 60, a ventilator machine 900, a source(s) of fluid (e.g. pressurized) and a source(s) of suctioning 603, the cleaning device comprising:

a. a tube-connector assembly 158 for connecting the ventilation tube 60 to the ventilator machine 900, in a substantially air-tight manner;

b. an elongate, flexible, main body 210 that is insertable through the tube-connector assembly 158 into the ventilation tube 60 to form an interstitial region outside of the main body 210 within ventilation tube 60;

c. a balloon 588 mounted to the main body 210 at a location (for example in the distal half of the main body) and inflatable into contact with an inner surface 201 of the ventilation tube 60;

d. one or more fluid delivery lumen(s) 520 arranged within or along the elongated main body, and operative to transport pressurized fluid received from pressurized fluid source(s) outside of the ventilation tube 60, into a proximal portion 774 of the interstitial region that is proximal of the balloon 588 so that the transported fluid enters the proximal portion 774 via fluid delivery orifice(s) 525 located on or mechanically coupled to the main body 210;

e. suction lumen(s) 520 arranged within or along the main body, and operative to convey negative pressure from suction source(s) 603 predominantly into the proximal portion 774 of interstitial region via suction orifice(s) 440 when balloon 588 is inflated into contact, suction orifice(s) 440 being open to the proximal portion 774 and mechanically coupled to the main body 210.

f. a suction port 820 connectable to the suction source(s) 603 for mediating a connection between the suction source and the suction lumen(s); and g. a pliable sleeve 610 around at least a portion of the main body 210 in locations proximal to the tube-connector assembly 158 and distal to the suction port 820 to inhibit contamination.

In some embodiments, the balloon 588 is inflated by liquid or gas supplied by balloon fluid source that is located in the tube-assembly-proximal location.

In some embodiments, balloon 588 is supplied via a balloon lumen(s) 580 that is different from fluid delivery lumen(s) 520.

In some embodiments, balloon 588 is inflated by gas or by a liquid.

In some embodiments, the fluid delivered via orifice(s) 525 and/or sent through fluid delivery lumen(s) 520 is a liquid and/or a liquid-gas mixture (e.g. a mist or bubbled fluid).

In some embodiments, balloon 588 is inflated by fluid (e.g. liquid and/or liquid-gas mixture) delivered via fluid delivery lumen(s) 520.

In some embodiments, a length of the pliable sleeve 610 is at least 5 cm.

In some embodiments, the method is carried out when the suction orifice(s) and/or the fluid delivery are located closer to balloon 588 than to a proximal end 62 of ventilation tube 60.

In some embodiments, the method is carried out at a time when a pliable sleeve 610 is arranged around at least a portion of the main body 210 in locations 598 proximal to the tube-connector assembly 158.

In some embodiments, the method is carried out at a time when a pliable sleeve 610 is arranged around at least a portion of the main body 210 in locations 598 proximal to the tube-connector assembly and distal to a suction port 820 which mediates a connection between suction source(s) 603 and suction lumen(s) 520.

In some embodiments, the one or more suction orifice(s) is(are) longitudinally displaced from the balloon 588 by at most a suction-orifice-displacement-value that is at most 3 cm or at most 2 cm or at most 1 cm.

In some embodiments, i. the pressurized fluid is simultaneously forced through first 525A and second 525B fluid delivery orifices to respectively produce first 556A and second 556B fluid streams that are respectively and simultaneously incident upon an inner surface 201 of the ventilation tube 60 at first 552A and second 552B locations; and ii. the first 552A and second 552B locations are substantially on opposite sides of the ventilation tube 60 inner surface 201 within a tolerance that is at most 75 degrees or at most 45 degrees or at most 25 degrees.

In some embodiments, at least one fluid-delivery-orifice 525 is proximally displaced from the slidable boundary by at most a fluid-orifice-displacement-value that is at most 3 cm, or at most 2 cm or at most 1 cm.

In some embodiments, the first 525A and second 525B fluid delivery orifices are respectively supplied via first 520A and second 520B fluid-delivery lumens.

In some embodiments, the first 520A and second 520B second fluid delivery lumens are simultaneously supplied by a common pressurized fluid chamber (e.g. a chamber mixing apparatus 696 of any other chamber).

In some embodiments, immediately before exiting each fluid delivery port 525, the delivered fluid is pressurized to at least 1.5 atmospheres, or at least 2 atmospheres or at least 3 atmospheres.

In some embodiments, each fluid delivery orifice 525 has a width of at most 5 mm, at most 3 mm, or at most 2 mm, or at most 0.5 mm, at most 0.3 mm, at most 0.2 mm.

In some embodiments, each fluid delivery orifice 525 has width that is at most 50%, or at most 25% or at most 10%, or at most 5%, of an average width of the 440 suction orifice(s).

In some embodiments, the suction-orifice-displacement-value is at most 2 cm, or at most 1 cm or at most 0.5 cm.

In some embodiments, the ventilation tube 60 is an ETT.

In some embodiments, the ventilation tube 60 is a tracheostomy tube.

In some embodiments, the fluid delivery operation and the suctioning are carried out simultaneously.

In some embodiments, the fluid delivery operation and the suctioning are carried out sequentially.

In some embodiments, concurrent to the maintaining of the slidable boundary, longitudinally moving the boundary-forming balloon 588 so as to mechanically dislodge and/or loosen biofilm material located on the inner surface 201 of the ventilation tube 60.

In some embodiments, the longitudinal moving is carried out simultaneously with the fluid delivery operation and/or the suctioning.

In some embodiments, at least one of the fluid delivery orifice(s) 525 are deployed to and/or voids within a second balloon 586 deployed distal to the boundary-forming balloon 588.

In some embodiments, the second balloon 586 is inflatable.

In some embodiments, the second balloon 586 is not inflatable.

In some embodiments, at least one of the at least one of the fluid delivery orifice(s) 525 is an inner-surface-facing void in the main body 210 facing towards the inner surface 201 of the ventilation tube 60 or a inner-surface-facing-void in a fluid-delivery lumen 520 that at least spans a longitudinal range between the fluid delivery orifice(s) 525 and a location on or within the main body 210 that is proximal to the ventilation tube connector assembly 158.

In some embodiments, i. at least one of the at least one of the fluid delivery orifice(s) 525 is a void in the boundary-forming balloon 588 so that the boundary-forming balloon 588 is leaky;

ii. forcing of pressurized fluid into the boundary-forming balloon 588 is operative to carry out at least some of both of the balloon-inflation operation and the fluid-delivery of the fluid-delivery operation.

In some embodiments, a surface of the boundary-forming balloon 588 is at least 90% or at least, by surface area, substantially impermeable.

In some embodiments, a surface of the boundary-forming balloon 588 is at most 99%, by surface area, substantially impermeable.

In some embodiments, boundary-forming 588 balloon is substantially sealed and is not leaky.

In some embodiments, further comprising carrying out the additional step of:

D. concurrent with the maintaining of the ventilation circuit, and at a time that the boundary-forming balloon 588 mounted to the elongate, flexible main body 210 is located within the ventilation tube 60 and in a non-obstructing mode so that the slidable boundary with the inner surface 201 of the ventilation tube 60 is not maintained and/or in non-contact mode so that balloon 588 is not inflated into contact with the inner surface 201 of ventilation tube 60, proximally suctioning into the suction orifice(s) 440 material that is located:

I. within the ventilation tube 60 and distal to the boundary-forming balloon 588; and/or II. distal to the ventilation tube distal end 60 so that the material located distal to the ventilation tube distal end 60 enters an interior region of ventilation tube 60 en route to the suction orifice(s), wherein the suctioning step when the boundary-forming balloon 588 is in non-obstructing and/or non-contact mode is carried out to proximally transport material suctioned in step D proximally out of ventilation tube 60 via a proximal opening of the ventilation tube 60.

In some embodiments, the balloon is mounted to the main body 210 at a location in a distal half, or distal third, or distal quarter, or distal fifth or distal tenth of the main body 210.

In some embodiments, an inner diameter of ventilation tube 60 is at least 4 mm and/or at most 11 mm.

In some embodiments, the pressurized fluid source 602 and the suction source 603 are respectively operative, in combination with the lumens and the orifices, to effect the fluid delivery and the suctioning when the boundary-forming balloon 588 is located in a distal half of the ventilation tube 60 and/or the system lacks suction orifice(s) more distal than the balloon 588.

In some embodiments, the system lacks suction orifice(s) more distal than the balloon 558 and/or distal to boundary and in fluid communication with suction source 603.

In some embodiments, the combined total aperture area of any and all suction orifices more distal than the balloon 588 and/or open to distal locations 778 is at most 50%, or at most 40%, or at most 30%, or at most 20%, or at most 10% of the combined total aperture area of any and all suction orifices 440 proximal to the balloon 558 and/or open to proximal location(s) 774.

In some embodiments, the combined total aperture area of any and all suction orifices in fluid communication with suction source 603 and more distal than the balloon 588 and/or open to distal locations 778 is at most 50%, or at most 40%, or at most 30%, or at most 20%, or at most 10% of the combined total aperture area of any and all suction orifices 440 in fluid communication with suction source 603 and proximal to the balloon 558 and/or open to proximal location(s) 774.

In some embodiments, further comprising: a sleeve 610 operative to envelop and/or cover at least 5 cm of the elongate flexible main body 210.

In some embodiments, wherein a distal end of the sleeve 610 is directly or indirectly attached to ventilation tube connector assembly 158 so that the main body 210 may slide through the sleeve.

In some embodiments, a proximal end of sleeve 610 is configured to have a substantially fixed longitudinal position relative to a proximal end of elongate flexible main body 210.

In some embodiments, the system lacks suction orifice(s) more distal than the balloon 558 and/or distal to boundary.

In some embodiments, the system lacks suction orifice(s) more distal than the balloon 558 and/or distal to boundary and in fluid communication with suction source 603.

In some embodiments, wherein the combined total aperture area of any and all suction orifices more distal than the balloon 588 and/or open to distal locations 778 is at most 50%, or at most 40%, or at most 30%, or at most 20%, or at most 10% of the combined total aperture area of any and all suction orifices 440 proximal to the balloon 558 and/or open to proximal location(s) 774.

In some embodiments, the combined total aperture area of any and all suction orifices in fluid communication with suction source 603 and more distal than the balloon 588 and/or open to distal locations 778 is at most 50%, or at most 40%, or at most 30%, or at most 20%, or at most 10% of the combined total aperture area of any and all suction orifices 440 in fluid communication with suction source 603 and proximal to the balloon 558 and/or open to proximal location(s) 774.

In some embodiments, wherein at least one of the suction orifice(s) 440 is in fluid communication, via suction lumen 520, with a blocking construct or blocking element that is distal of at least one suction orifice 440 and that is configure to mostly or completely block fluid communication with a distal opening 519. 132. The device, system or method of any of preceding claim wherein the blocking construct or blocking element comprises a blocking glue or other material introduced onto or into suction lumen 520 and/or comprises a melt construct of a melted inner wall(s) of suction lumen(s) 520.

In some embodiments, the system is operative such that:
i. the pressurized fluid is simultaneously forced through first 525A and second 525B fluid delivery orifices to respectively produce first 556A and second 556B fluid streams that are respectively and simultaneously incident upon an inner surface 201 of the ventilation tube 60 at first 552A and second 552B locations; and
ii. the first 552A and second 552B locations are substantially on opposite sides of the ventilation tube 60 inner surface 201 within a tolerance that is at most 75 degrees.

In some embodiments, the system or apparatus comprises a plurality of fluid delivery orifices 525 including:
i. a first fluid delivery orifice 525A deployed to a first side of the elongate main body 210; and
ii. a second fluid delivery orifice 525B deployed substantially to a second side of the elongate main body 210 that is on opposite side of main body central axis 202 within a tolerance that is at most 75 degrees or at most 45 degrees or at most 25 degrees.

In some embodiments, the the system or apparatus comprises first 525A and second 525B fluid delivery orifice(s) which are operative such that:
i. when an inner diameter of ventilation tube 60 is between 4 and 11 mm and exceeds an outer diameter of main body 210,
ii. when the main body 210 traverses the ventilation tube connector 158 so as to enter the ventilation tube;
iii. when the boundary-forming balloon 588 is inflated so as to maintain the boundary; and
iv. when the pressurized fluid is simultaneously forced, via fluid delivery lumen(s) 530 through first 525A and second 525B fluid delivery orifice, to respectively produce first 556A and second 556B fluid streams that are respectively and simultaneously incident upon an inner surface 201 of the ventilation tube 60 at first 552A and second 552B locations such that the first 552A and second 552B locations are substantially on opposite sides of the ventilation tube 60 inner surface 201 within a tolerance that is at most 75 degrees or at most 45 degrees or at most 25 degrees.

In some embodiments, at least one fluid-delivery-orifice 525 is proximally displaced from the slidable boundary by at most a fluid-orifice-displacement-value that is at most 3 cm, or at most 2 cm.

In some embodiments, the first 520A and second 520B fluid second fluid delivery lumens are simultaneously supplied by a common pressurized fluid chamber.

In some embodiments, immediately before exiting each fluid delivery port 525, the delivered fluid is pressurized to at least 1.5 atmospheres, or at least 2 atmospheres or at least 3 atmospheres.

In some embodiments, one or more fluid delivery orifice 525, or a majority of the fluid delivery orifice(s) 525, has a width of at most 3 mm, or at most 2 mm or at most 1 mm, or at most 0.5 mm, at most 0.3 mm, at most 0.2 mm and/or that is at most 50% or at most 25% or at most 10% or at most 5% of an average width of the 440 suction orifice(s).

In some embodiments, the suction-orifice-displacement-value is at most 2 cm, or at most 1 cm or at most 0.5 cm.

In some embodiments, the main body 210 is operative to slidably, snugly and/or internally traverse the connector assembly 158.

In some embodiments, i. negative pressure from suction source(s) 603 induces air flow within the interstitial region; and
ii. the cleaning device provides a mode whereby a maximum rate of the induced air flow within a distal portion 778 of the interstitial region distal to the inflatable balloon 588 is at most 20% of a maximum rate of the induced air flow in the proximal portion 774.

In some embodiments, all suction lumen(s) are collectively not in fluid communication with any suction orifice located distal to balloon 588.

In some embodiments,
i. collectively all suction lumen(s) of the cleaning device are in fluid communication with one or more proximal suction orifice(s) located proximal to balloon 588 and one or more distal orifice(s) located distal to balloon 588; and
ii. a ratio between an aggregate surface area of all proximal suction orifice(s) 440 to an aggregate surface area of all distal suction orifice(s) is at least SURF_AREA_RAT;
iii. a value of SURF_AREA_RAT is at least 1.5.

Although various embodiments were describe with respect to assembled systems, it is appreciate that kits including one or more parts which, when assembled, form any presently disclosed apparatus or device or portion thereof are also in the scope of the invention. In different non-limiting examples, connector assembly 158 and/or input module assembly 156 and/or any port disclosed herein may be provided as parts which may be assembled on-site (e.g. in the intensive care ward). In some examples, sleeve 610 may be part of a kit and deployed on site. Other configurations are within the scope of embodiments of the invention.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to. The term "or" is used herein to mean, and is used interchangeably with, the term "and/or," unless context clearly indicates otherwise. The term "such as" is used herein to mean, and is used interchangeably, with the phrase "such as but not limited to".

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. A ballooned cleaning device for use with an ETT or tracheostomy ventilation tube 60, a ventilator machine 900, a source(s) 602 of pressurized liquid and a source(s) of suctioning 603, the cleaning device comprising:
   a. a tube-connector assembly 158 for connecting the ventilation tube 60 to the ventilator machine 900, in a substantially air-tight manner;
   b. an elongate, flexible, main body 210 that is insertable through the tube-connector assembly 158 into the ventilation tube 60 to form an interstitial region outside of the main body 210 within ventilation tube 60;
   c. a balloon 588 mounted to the main body 210 at a location in the distal half of the main body and inflatable into contact with an inner surface 201 of the ventilation tube 60;
   d. one or more liquid-delivery lumen(s) 520 arranged within or along the elongated main body, and operative to transport pressurized liquid received from pressurized liquid source(s) outside of the ventilation tube 60, into a proximal portion 774 of the interstitial region that is proximal of the balloon 588 so that the transported liquid enters the proximal portion 774 via liquid delivery orifice(s) 525 located on or mechanically coupled to the main body 210;
   e. suction lumen(s) 530 arranged within or along the main body 210, and operative to convey negative pressure from suction source(s) 603 predominantly into the proximal portion 774 of interstitial region via suction orifice(s) 440 when balloon 588 is inflated into contact, suction orifice(s) 440 being open to the proximal portion 774 and mechanically coupled to the main body 210;
   f. a suction port 830 connectable to the suction source(s) 603 for mediating a connection between the suction source and the suction lumen(s); and
   g. a pliable sleeve 610 around at least a portion of the main body 210 in locations proximal to the tube-connector assembly 158 and distal to the suction port 830 to inhibit contamination wherein at least one of the fluid delivery orifice(s) 525 is a void in a surface of the balloon 588 so that the balloon 588 is leaky, wherein a ratio between an area of all voids in a surface of the leaky balloon and the total area of a surface of the leaky balloon is at most 0.1.

2. The device of claim 1 wherein inflatable balloon is operative to be inflated by pressurized fluid source via fluid delivery lumen(s) 520.

3. The system of claim 1 wherein:
   i. inflatable balloon 588 is a leaky balloon having one or more surface-located leak holes; and
   ii. one or more of the fluid delivery orifice(s) 525 are leak holes that face in a direction having a proximal component; and
   iii. inflatable balloon is operative to be inflated by pressurized fluid source via fluid delivery lumen(s) 520.

4. The device of claim 1 wherein:
   i. balloon 588 is a boundary-forming balloon which divides an interior of the ventilation tube into more proximate 774 and more distal 778 portions;
   ii. at least one of the at least one of the fluid delivery orifice(s) 525 is a void in the boundary-forming balloon 588 so that the boundary-forming balloon 588 is leaky;
   iii. forcing of pressurized liquid into the boundary-forming balloon 588 is operative both:
      A. to inflate boundary-forming balloon 588;
      B. to cause the pressurized liquid to enter the proximal portion 774 via liquid delivery orifice(s) 525 located on or mechanically coupled to the main body 210.

5. The device of claim 4 wherein the boundary-forming balloon 588 forms a seal between the proximate 774 and distal 778 portions of the interstitial region.

6. The device of claim 4 wherein the boundary-forming balloon 588 does not form a seal between the into proximate 774 and distal 778 portions of the interstitial region.

7. The device of claim 4 wherein the balloon 588 hinders and/or at least partially obstructs fluid communications between the more proximal and more distal portions.

8. The device of claim 1 wherein a ratio between an area of all voids in a surface of the leaky balloon and the total area of a surface of the leaky balloon is at most 0.05.

9. A method of using the device of claim 1 comprising:
   a. providing the device of claim 1;
   b. introducing pressurized fluid into an interior of the leaky balloon at a sufficient rate to maintain inflation of the leaky balloon, thereby maintaining contact between the balloon and the inner surface of the ventilation tube.

10. The device of claim 9 wherein a ratio between an area of all voids in a surface of the leaky balloon and the total area of a surface of the leaky balloon is at most 0.05.

11. The method of claim 9 wherein:
   i. the fluid delivery lumen is a spanning lumen that spans a length of the main body between the proximal end of main body and the balloon 588;
   ii. the pressurized fluid is forced into the interior of the leaky balloon via the spanning lumen.

12. The method of claim 9 wherein introduced fluid is pressurized sufficiently so that it exits via the void(s) of the leaky balloon as a jet of fluid.

* * * * *